United States Patent
Zhang

(10) Patent No.: US 10,526,255 B2
(45) Date of Patent: Jan. 7, 2020

(54) COMPOSITIONS AND METHODS THEREOF INCREASING PLANT GROWTH AND RESISTANCE TO ENVIRONMENTAL STRESS

(71) Applicant: RUTGERS, THE STATE UNIVERSITY OF NEW JERSEY, New Brunswick, NJ (US)

(72) Inventor: Ning Zhang, East Brunswick, NJ (US)

(73) Assignee: Rutgers, The State University of New Jersey, New Brunswick, NJ (US)

(*) Notice: Subject to any disclaimer, the term of this patent is extended or adjusted under 35 U.S.C. 154(b) by 162 days.

(21) Appl. No.: 15/509,355

(22) PCT Filed: Sep. 8, 2015

(86) PCT No.: PCT/US2015/048889
§ 371 (c)(1),
(2) Date: Mar. 7, 2017

(87) PCT Pub. No.: WO2016/040285
PCT Pub. Date: Mar. 17, 2016

(65) Prior Publication Data
US 2018/0037517 A1 Feb. 8, 2018

Related U.S. Application Data

(60) Provisional application No. 62/047,226, filed on Sep. 8, 2014.

(51) Int. Cl.
*C05F 11/08* (2006.01)
*C12N 1/14* (2006.01)
*C12N 1/20* (2006.01)
*C05B 17/00* (2006.01)
*C05G 3/00* (2006.01)

(52) U.S. Cl.
CPC ............ *C05F 11/08* (2013.01); *C05B 17/00* (2013.01); *C05G 3/0029* (2013.01); *C12N 1/14* (2013.01); *C12N 1/20* (2013.01)

(58) Field of Classification Search
CPC ....... C05F 11/08; C05G 3/0029; C05B 17/00; C12N 1/14; C12N 1/20
See application file for complete search history.

(56) References Cited

U.S. PATENT DOCUMENTS

2014/0342905 A1* 11/2014 Bullis ................. A01N 63/00
504/100

FOREIGN PATENT DOCUMENTS

WO WO 2013/090628 6/2013
WO WO 2013/098829 7/2013

OTHER PUBLICATIONS

Walsh, Emily & Luo, Jing & Zhang, Ning. (2014). Acidomelania panicola gen. et. sp. nov. from switchgrass roots in acidic New Jersey Pine Barrens.. Mycologia. 106. 10.3852/13-377.*
Walsh, Emily, Jing Luo, and Ning Zhang. "Acidonnelania panicicola gen. et sp. nov. from switchgrass roots in acidic New Jersey pine barrens." Mycologia 106.4 (2014): 856-864.*

(Continued)

*Primary Examiner* — Jennifer A Smith
(74) *Attorney, Agent, or Firm* — Kathleen D. Rigaut; Howson & Howson LLP

(57) ABSTRACT

Compositions and methods for enhancing plant growth and resistance to adverse abiotic conditions are disclosed.

27 Claims, 28 Drawing Sheets
Specification includes a Sequence Listing.

(56) References Cited

OTHER PUBLICATIONS

Nailwal, Shweta, et al. "Burkholderia sp. from rhizosphere of Rhododendron arboretum: isolation, identification and plant growth promotory (PGP) activities." Journal of Applied and Natural Science 6.2 (2014): 473-479.*
Walsh, Emily, et al. "Barrenia, a new genus associated with roots of switchgrass and pine in the oligotrophic pine barrens." Fungal biology 119.12 (2015): 1216-1225.*
Blackwell M. 2011. The Fungi: 1, 2, 3 . . . 5.1 Million Species? Am J. Bot. 98:426-438.
Delaux PM, Sejalon-Delmas N, Becard G, Ane JM, 2013. Evolution of the plant-microbe symbiotic 'toolkit'. Trends in Plant Science 18:298-304.
Digby S, Goos R, 1987. Morphology, development and taxonomy of Loramyces. Mycologia 79:821-831.
Dighton J, Tuininga AR, Gray DM, Huskins RE, Belton T, 2004. Impacts of atmospheric deposition on New Jersey pine barrens forest soils and communities of ectomycorrhizae. Forest Ecology and Management 201:131-144.
Edgar RC, 2004. MUSCLE: multiple sequence alignment with high accuracy and high throughput. Nucleic Acids Research 32:1792-1797.
Gensel, P.G., Kotyk, M.E., Basinger, J.F. 2001. Morphology of Above and Below Ground Structures in Earl Devonian (Pragian-Emsian) Plants, in: PG G D E (Eds), Plants Invade the Land: Evolutionary and Environmental Perspectives. Columbia University Press, New York, pp. 83-102.
Grunig CR, Duo A, Sieber T, Holdenrieder O, 2008a. Assignment of species rank to six reproductively isolated cryptic species of the Phialocephala fortinii s.l.-Acephala applanata species complex. Mycologia 100:47-67.
Grunig CR, Queloz V, Sieber TN, Holdenrieder O, 2008b. Dark septate endophytes (DSE) of the Phialocephala fortinii s.l.—Acephala applanata species complex in tree roots: classification, population biology, and ecology. Botany 86:1355-1369.
Hall BD, Stiller JW, 1997. The origin of red algae: Implications for plastid evolution. Proceedings of the National Academy of Sciences of the USA 94:4520-4525.
Knapp DG, Pintye A, Kovacs GM, 2012. The dark side is not fastidious—dark septate endophytic fungi of native and invasive plants of semiarid sandy areas. PLoS ONE 7:e32570.
Luo J, Walsh E, Naik A, Zhuang W, Zhang K, Cai L, Zhang N, 2014a. Temperate pine barrens and tropical rain forests are both rich in undescribed fungi. PLoS ONE 9:e103753.
Luo J, Walsh E, Zhang N, 2014b. Four new species in Magnaporthaceae from grass roots in New Jersey Pine Barrens. Mycologia 106: 580-588.
Mandyam K, Fox C, Jumpponen A, 2012. Septate endophyte colonization and host responses of grasses and forbs native to a tallgrass prairie. Mycorrhiza 22:109-119.
Mandyam K, Jumpponen A, 2005. Seeking the elusive function of the root-colonising dark septate endophytic fungi. Studies in Mycology 53:173-189.
Mandyam K, Loughin T, Jumpponen A, 2010. Isolation and morphological and metabolic characterization of common endophytes in annually burned tallgrass prairie. Mycologia 102:813-821.
Matheny PL, Liu YJ, Ammirati JF, Hall, BD, 2002. Using Rpb1 Sequences to Improve Phylogenetic Inference Among Mushrooms (Inocybe, Agaricales). American Journal of Botany 89:688-698.
Mathew and Malathy RM, 2008, The evidence of mycorrhizal fungi and dark septate endophytes in roots of Chlorophytum borivilianum. Acta Botanica Croatica 67(1):91-96.
Menkis A, Allmer J, Vasiliauskas R, Lygis V, Stenlid J, Finlay R, 2004. Ecology and molecular characterization of dark septate fungi from roots, living stems, coarse and fine woody debris. Mycological Research 108:965-973.
Otgonsuren B, Lee MJ, 2013. Ectomycorrhiza Enhanced the Cold-Acclimation Growth and Freeze Tolerance of Scots Pine (*Pinus sylvestris* L.). Taiwan Journal of Forest Science 28:97-111.
Rehner SA, Samuels GJ, 1995. "Molecular systematics of the Hypocreales—a teleomorph gene phylogeny and the status of their anamorphs." Canadian Journal of Botany 73:S816-S823.
Stoyke, G, Currah, R.S.. 1991. Endophytic Fungi from the Mycorrhizae of Alpine Ericoid Plants. Can J. Bot. 69: 347-352.
Tamura K, Stecher G, Peterson D, Filipski A, Kumar S, 2013. MEGA6: Molecular Evolutionary Genetics Analysis version 6.0. Molecular Biology and Evolution 30:2725-2729.
Taylor JW, Jacobson DJ, Kroken S, Kasuga T, Geiser DM, Hibbett DS, Fisher MC, 2000. Phylogenetic species recognition and species concepts in fungi. Fungal Genetics and Biology 31:21-32.
Tedrow JCF, 1952. Soil Conditions in the Pine Barrens of New Jersey. Bartonia 26: 28-35.
Tuininga, A.R., Dighton, J. 2004. Changes in Ectomycorrhizal Communities and Nutrient Availability Following Prescribed Burns in Two Upland Pine-Oak Forests in the New Jersey Pine Barrens. Can. J. Forest Res. 34: 1755-1765.
Walsh E, Luo J, Zhang N, 2014. Acidomelania panicicola gen. et sp. nov. from switchgrass roots in acidic New Jersey pine barrens. Mycologia 106:856-864.
Wang Z, Johnston PR, Takamatsu S, Spatafora JW, Hibbett DS, 2006. Toward a phylogenetic classification of the Leotiomycetes based on rDNA data. Mycologia 98:1065-1075.
Weston WH, 1929. Observations on Loramyces, an undescribed aquatic ascomycete. Mycologia 21:55-76.
White TJ, Bruns T, Lee S, Taylor J, 1990. Amplification and direct sequencing of fungal ribosomal RNA genes for phylogenetics. In: Innis M, Gelfand D, Sninsky J, White T (eds) PCR Protocols: A Guide to Methods and Applications. New York: Academic Press.
Yu T, Nassuth A, Peterson RL, 2001. Characterization of the interaction between the dark septate fungus Phialocephala fortinii and Asparagus officinalis roots. Canadian Journal of Microbiology 47:741-753.
Zijlstra J, Van't Hof P, Baar J, Verkley G, Summerbell R, Paradi I, Braakhekke W, Berendse F, 2005. Diversity of symbiotic root endophytes of the Helotiales in ericaceous plants and the grass, Dechampsia flexuosa. Studies in Mycology 53:147-162.
International Search Report and Written Opinion issued in PCT/US2015/048889, dated Dec. 14, 2015.

\* cited by examiner

Acephala_applanata_AY078151

```
GTGTTTA---------------------------------------------------
----------------------------------------------------------
------CATACTATTGT-TGCTTTGGCGGGCCGTGA-CCT-CCAC--TGC----GGGCTC
TGCTCGT-----GTGTGCCCGCCAGAGGACC---AAACTCTGAATGTTAGTGATGTCTGA
GTACTATCTAATAGTTAAAACTTTCAACAACGGATCTCTTGGTTCTGGCATCGATGAAGA
ACGCAGCGAAATGCGATAAGTAATGTGAATTGCAGAATTCAGTGAATCATCGAATCTTTG
AACGCACATTGCGCCCTGTGGTATTCCGCAGGGCATGCCTGTTCGAGCGTCATT-TAACC
ACTCACGCCTGGCGTGGTATTGGGGT-ACGCGGT--CTCGCGGCCCTCAAAATCAGTGGC
GGTGCCGGTG-GGCTCTAAGCGTAGTAC-ATACTCCCGCTATAGAGTTC----------
-----------------CC--------------------------CCGGTGGCTCGC--
-----------------------ACCCGCTGAACTTAAGCATATCAATAAGCGGAGGAA
AAGAAACCAACAGGGATTACCTCAGTAACGGCGAGTGAAGCGGTAACAGCTCAAATTTGA
AAGCTGCC-----AACAGGCCGCGTTGTAATTTGTAGARGCTGCTTTGGGTGTCGGCCCG
GTCTAAGTTCCTTGGAACAGGACGTCATAGAGGGTGAGAATCCCGTATGTGATCGG-TGC
CGTTGCCCGTGTAAAGCGCTTTCGACGAGTCGAGTTGTTTGGGAATGCAGCTCAAAATGG
GTGGTAAATTTCATCTAAAGCTAAATATTGGCCAGAGACCGATAGCGCACAAGTAGAGTG
ATCGAAAGATGAAAAGCACTTTGGAAAGAGAGTTAAACAGTACGTGAAATTGTTGAAAGG
GAAGCGCTTGCAACCAGACTTGCGGGCGGTCGATCATCCGAGGTTC-TCCCGGTGCACT
CGATCGTTC-TCAGGCCAGCATCGGTTTCCGGGGTGGGATAAAGGCGGTGGGAATGTGGC
TC--TTC------GGAGTGTTATAGCCCACCGTGCAATGCCGCCACCGGGGACCGAGGAC
CGCGCTTC-GGCTAGGATGCTGGCGTAATGGTTGTAAGCGACCCGTCTTGAAACACGGAC
CAAGGAGTCTAACATCTATGCGAGTGTTTGGGTGTCAAACCCATACGCGTAATGAAAGTG
AACGGAGGTAAGAGCCCTTTAGGGTGCATTATCGACCGATCCTGATGTCTTCGGATGGAT
TTGAGTAAGAGCATAGCTGTTGGGACCCGAAAGATGGTGAACTATGCGTGAATAGGGTGA
AGCCAGAGGAAACTCTGGTGGAGGCTCGCAGCGGTTCTGACGTGCAAATCGATCGTC-AA
ATTTGCGTATAGGGGC-GAAAGACTAATCGGCTAGACAGAGTCAGTTCG---CCCGATGA
GGGTGGCAGATCTACT--TGTTC--TYGTGCTGACATGAGT-ATCTCAGAGTAATCCGGC
CTTCAAAGCAGCTGTTTCCATTCGAGACCCGAAGCGTAGGTTCGATACGATTTGGCGACT
TTGCAAGCCCAAGATGATCTGCGATAGCGACGTTTCTGCGGACGATCAAGAATTCGGTGG
CGATCCAAAGGAAGCCGTGAAG---CGCTCTCATGGAGGCTGTGGAAATACTCAGCCCGA
GGTGCGCCAGCAGGCTCTGCAGCTTTGGGTACATGGAAGATGCCTAAGGACGAGGAGAA
CGAGGG------AAGCCAATCCGAGAAGAGACAAATCACTCCAGAGATGGCTCTGAACGT
CTTCCGAAGCATGTCTACTGCTGAGATTCGCGACCTTGGGTTGAGCAACGATTATGCCCG
ACCCGACTGGCTGATCATCACAGTCCTTCCAGTTCCTCCTCCGCCGGTTCGACCAAGTAT
CTCAATGGATGGCACAAGCACAGGCATGCGTGGAGARGATGATTTGACGTACAAGCTCGG
TGATATCATCCGTGCGAACGGCAATGTCAAGC-AGGCACAACAGGAAGG
```

Figure 4A

```
Acidomelania_panicicola_KF874620
GTGTCTA-----------------------------------------------------
------------------------------------------------------------
------CATACTCTTGT-TGCTTTGGCAGGCCGTGG-CCTCCCAC--TGT----GGGCTC
AGCCTGC-----ATGTGCCTGCCAGAGGACC---AAACTCTGAATGTTACTGATGTCTGA
GTACTATATAATAGTTAAAACTTTCAACAACGGATCTCTTGGTTCTGGCATCGATGAAGA
ACGCAGCGAAATGCGATAAGTAATGTGAATTGCAGAATTCAGTGAATCATCGAATCTTTG
AACGCACATTGCACCCGGTGGTATTCCGCCGGGTATGCCTGTTCGAGCGTCATTACAACC
ACTCAAGCCTGTCTTGGTGTTGGGGA-TTGCGAAT-CTCGCAGCCCTAGAGTCCAGTAGC
GTCACCTTTA-GGTCCTAAGCGTAGTAATTTCTCCTCGCTACAGAACCT-----------
------------------GCCGGTGGATAGTATAAATCCAGTTAAGTCTGGTATCCCGC-G
GTTGACCTCGGATCAAGTAGGGATACCCGCTGAACTTAAGCATATCAATAAGCGGAGGAA
AAGAAACCAACAGGGATTACTTTAGTAACGGCGAGTGAAGCGGTAACTGCTCAAATTTGA
AAGCTGCC-----AACAGGCCGCGTTGTAATTTGTAGAAGATGCTTTGGGTGTCGGCCCA
GTCTAAGTTCCTTGGAACAGGACGTCATAGAGGGTGAGAATCCCGTATGTGATTGG-TGC
CGTCCCCCGTGTAAAGCTCTTTCGACGAGTCGAGTTGTTTGGGAATGCAGCTCAAAATGG
GTGGTAAATTTCATCTAAAGCTAAATATTGGCCAGAGACCGATAGCGCACAAGTAGAGTG
ATCGAAAGATGAAAAGCACTTTGGAAAGAGAGTTAAACAGTACGTGAAATTGTTGAAAGG
GAAGCGCTTGCAATCAGACTTGCAGGCGGTTGATCATCCGAGGTTC-TCCCCGGTGCACT
CGATCGTCT-TCAGGCCAGCATCGGTTTCAGTGGTGGGATAAAGGCTGTGAGAACGTGGC
TC--TTC------GGAGTGTTATAGCTCACGGTGCAATGCCGCCTACTGGGACCGAGGAC
CGCGCTTC-GGCTAGGATGCTGGCGTAATGGTTGTAAGCGACCCGTCTTGAAACACGGAC
CAAGGAGTCTAACATCTATGCGAGTGTTTGGGTGTCAAACCCATACGCGTAATGAAAGTG
AACGGAGGTGAGACCCCATTAGGGCGCATCATCGACCGATCCTGATGTCTTCGGATGGAT
TTGAGTAAGAGCATAGCTGTTGGGACCCGAAAGATGGTGAACTATGCGTGAATAGGGTGA
AGCCAGAGGAAACTCTGGTGGAGGCTCGCAGCGGTTCTGACGTGCAAATCGATCGTC-AA
ATTTGCGTATAGGGGC-GAAAGACTAATCGGTTAGACAGGGTCAGTTCA---CCCGTATA
GGGTGGTGGCATCTCT--TGCAT-CTTGTGCTGACATGAAT-ATCTCAGAGTAACCCGCA
ATACAAGGCAGCTGTTTCTATTCGGGACCCAAAGCGTAGATTCGACACCATTTGGCGACT
TTGCAAGCCCAAGATGATCTGCGACAGTGATGTTCCTAATGACGAC---GAATTCGGAGG
TGATCCAAAGGAGGCTGTGAAG---CGTTCGCATGGAGGATGTGGAAATACGCAACCTGA
GGTGCGCCAGCAAGCTTTGCAGCTTTGGGGAACATGGAAGATGCCAAAAGATGAAGAGAA
TGAGGGTGG--CAACACT----GAGAAGCGACAAATTACTCCAGAGATGGCTCTCAATGT
CTTCCGGTCCATGTCTTCCGATGAGATTCGCGATCTCGGTTTGAGCAACGACTATGCGCG
TCCTGACTGGTTGATCATCACTGTTCTTCCAGTTCCACCTCCTCCCGTTCGCCCCAGTAT
TTCTATGGATGGTACAAGCACAGGAATGCGCGGAGAGGATGATTTGACCTACAAGCTAGG
TGATATCATTCGTGCCAACGGCAATGTCAAGC-AGGCACAGCAAGAAGG
```

Figure 4B

Acidomelania_panicicola_KF874619
GTGTCTA-----------------------------------------------------
------------------------------------------------------------
------CATACTCTTGT-TGCTTTGGCAGGCCGTGG-CCTCCCAC--TGT----GGGCTC
AGCCTGC-----ATGTGCCTGCCAGAGGACC---AAACTCTGAATGTTAGTGATGTCTGA
GTACTATATAATAGTTAAAACTTTCAACAACGGATCTCTTGGTTCTGGCATCGATGAAGA
ACGCAGCGAAATGCGATAAGTAATGTGAATTGCAGAATTCAGTGAATCATCGAATCTTTG
AACGCACATTGCACCCGGTGGCATTCCGCCGGGTATGCCTGTTCGAGCGTCATTATAACC
ACTCAAGCCTGTCTTGGTGTTGGGGA-TTGCGAAT-CTCGCAGCCCTAGAGTCCAGTAGC
GTCACCTGTG-GGTCCTAAGCGTAGTAATTTCTCCTCGCTACAGAGCCT-----------
-----------------GCTCGTGGATAGTGTAAATCCAGTTCGGTCTGGTATCCCGC-G
GTTGACCTCGGATCAAGTAGGGATACCCGCTGAACTTAAGCATATCAATAAGCGGAGGAA
AAGAAACCAACAGGGATTAC--TAGTAACGGCGAGTGAAGCGGTAACTGCTCAAATTTGA
AAGCTGCC-----AACAGGCCGCGTTGTAATTTGTAGAAGATGCTTTGGGTGTCGGCCCA
GTCTAAGTTCCTTGGAACAGGACGTCATAGAGGGTGAGAATCCCGTATGTGATTGG-TGC
CGTCCCCCGTGTAAAGCTCTTTCGACGAGTCGAGTTGTTTGGGAATGCAGCTCAAAATGG
GTGGTAAATTTCATCTAAAGCTAAATATTGGCCAGAGACCGATAGCGCACAAGTAGAGTG
ATCGAAAGATGAAAAGCACTTTGGAAAGAGAGTTAAACAGTACGTGAAATTGTTGAAAGG
GAAGCGCTTGCAATCAGACTTGCAGGCGGTTGATCATCCGAGGTTC-TCCCCGGTGCACT
CGATCGTCT-TCAGGCCAGCATCGGTTTCAGTGGTGGGATAAAGGCTGTGAGAACGTGGC
TC--TTC------GGAGTGTTATAGCTCACGGTGCAATGCCGCCTACTGGGACCGAGGAC
CGCGCTTC-GGCTAGGATGCTGGCGTAATGGTTGTAAGCGACCCGTCTTGAAACACGGAC
CAAGGAGTCTAACATCTATGCGAGTGTTTGGGTGTCAAACCCATACGCGTAATGAAAGTG
AACGGAGGTGAGACCCCATTAGGGCGCATCATCGACCGATCCTGATGTCTTCGGATGGAT
TTGAGTAAGAGCATAGCTGTTGGGACCCGAAAGATGGTGAACTATGCGTGAATAGGGTGA
AGCCAGAGGAAACTCTGGTGGAGGCTCGCAGCGGTTCTGACGTGCAAATCGATCGTC-AA
ATTTGCGTATAGGGGC-GAAAGACTAATCGGTTAGACAGGGTCAGTTCA---CCCGTATA
GGGTGGTGGCATCTCT--TGCAT-CTTGTGCTGACATGAGT-ATCTCAGAGTAACCCGCA
ATACAAGGCAGCTGTTTCTATTCGGGATCCAAAGCGTAGATTCGACACCATTTGGCGACT
TTGCAAGCCCAAGATGATCTGCGACAGTGATGTTCCTAATGACGAC---GAATTCGGAGG
TGATCCAAAGGAGGCTGTGAAG---CGTTCCCATGGAGGATGTGGAAATACGCAACCTGA
GGTGCGCCAGCAAGCCTTGCAGCTTTGGGGAACATGGAAAATGCCAAAGGATGAAGAGAA
TGAGAGTGG--CAACACT----GAGAAGCGACAAATTACTCCAGAGATGGCTCTCAATGT
CTTCCGGTCCATGTCTTCCGATGAGATTCGCGATCTCGGTTTGAGCAACGACTATGCGCG
TCCTGACTGGTTGATCATCACTGTTCTTCCAGTTCCACCTCCTCCTGTTCGCCCCAGTAT
TTCTATGGATGGTACAAGCACAGGAATGCGCGGAGAGGATGATTTGACCTACAAGCTGGG
TGATATCATTCGCGCCAACGGCAATGTCAAGC-AGGCACAGCAAGAAGG

Figure 4C

```
Acidoradicia_panicicola_AL5m2-2
GTGTCTA---------------------------------------------------------
----------------------------------------------------------------
------TCTACTCTTGT-TGCTTTGGCAGGCCGTGG-CCT-CCAC--CGC----GGGCTC
TGCCTGC-----GTGTGCCTGCCAGAGGACC---AAACTCTGAATTTTAGTGATGTCTGA
GTACTATATAATAGTTAAAACTTTCAACAACGGATCTCTTGGTTCTGGCATCGATGAAGA
ACGCAGCGAAATGCGATAAGTAATGTGAATTGCAGAATTCAGTGAATCATCGAATCTTTG
AACGCACATTGCGCCCGGTGGTATTCCGCCGGGCATGCCTGTTCGAGCGTCATTATAACC
ACTCAAGCCTAGCTTGGTATTGGGGT-TCGCGGT--CCCGCGGCCCCTAAAATCAGTGGC
GGTGCCGGTG-GGCTCTAAGCGTAGTAA-ATCTCCTCGCTATAGGGTCC-----------
-----------------CC-------------------------CCGGTTGCCCGC-G
GTTGACCTCGGATCAGGTAGGGATACCCGCTGAACTTAAGCATATCAATAAGCGGAGGAA
AAGAAACCAACAGGGATTAC-TCAGTAACGGCGAGTGAAGCGGTAACAGCTCAAATT-GA
AAGCTGCC-----AACAGGCCGCGTTGTAATTTGTAGAAGATGCTTTGGGGGTAGGCCTA
GTCTAAGTTCCTTGGAACAGGACGTCATAGAGGGTGAGAATCCCGTATGTGATTAG-TGC
CTGCTCCCGTGTAAAGCTCTTTCGACGAGTCGAGTTGTTTGGGAATGCAGCTCAAAATGG
GTGGTATATTTCATCTAAAGCTAAATATTGGCCAGAGACCGATAGCGCACAAGTAGAGTG
ATCGAAAGATGAAAAGCACTTTGGAAAGAGAGTTAAACAGTACGTGAAATTGTTGAAAGG
GAAGCGCTTGCAACCAGACTTGCAGGCGGTCGATCATCCGAGGTTC-TCCCCGGTGCACT
CGATCGTCT-TCAGGCCAGCATCGGTTTTGGTGGCGGGATAAAGGCTCTAGGAATGTGGC
TC--TTC------GGAGTGTTATAGCCTAGGGTGCAATGCCGCCTACCGGGACCGAGGAC
CGCGCTTC-GGCTAGGATGCTGGCGTAATGGTTGTAAGCGGCCCGTCTTGAAACACGGAC
CAAGGAGTCTAACATCTATGCGAGTGTTTGGGTGTCAAACCCATACGCGTAATGAAAGTG
AACGGAGGTGAGAGCCCTTTAGGGCGCATCATCGACCGATCCTGATGTCTTCGGATGGAT
TTGAGTAAGAGCATAGCTGTTGGGACCCGAAAGATGGTGAACTATGCGTGAATAGGGTGA
AGCCAGAGGAAACTCTGGTGGAGGCTCGCAGCGGTTCTGACGTGCAAATCGATCGTC-AA
ATTTGCGTATAGGGGC-GAAAGACTAATCGGCTAGACAGGGTCAGTTCG---CCCGAAAA
GGGTGGCGGATCTACT--TGTTC-TTTGTGCTGACATGAGT-TTCTCAGAGTAATCCGGC
ATACAAGGCAGCCGTTTCGATTCGAGACCCGAAGCGTAAGTTCGATACCATATGGCGACT
TTGCAAGCCCAAGATGATCTGCGACAGCGATGTCCCTAACGACGAT---GAATTTGGTGG
TGATCCAAAGGAAGCTGTTAAA---CGTTCTCATGGAGGTTGTGGCAATACTCAACCCGA
GGTTCGCCAACAAGCTTTACAGCTCTGGGGAACATGGAAGATGCCCAAGGATGAAGAAAA
CGAGGGTG---CGACTCAA---GAAAAGAGACAGATTACTCCAAAGATGGCTCTGAATGT
CTTCCGCAGCATGTCCTCGGCTGAGATTCGCGATTTGGGCTTGAGCAATGACTATGCACG
CCCTGACTGGCTTATCATTACTGTCCTTCCTGTTCCTCCCCGCCTGTTCGACCGAGTAT
CTCCATGGATGGTACAAGCACAGGAATGCGCGGAGAGGATGATTTGACATACAAGCTTGG
TGATATTATTCGTGCAAACGGAAACGTTAAGC-AAGCCCAACAAGAGGG
```

Figure 4D

```
Acidoradicia_panicicola_CM11M2
GTGTCTA---------------------------------------------------------
-----------------------------------------------------------------
------TCTACTCTTGT-TGCTTTGGCAGGCCGTGG-CCT-CCAC--CGC----GGGCTC
TGCCTGC-----GTGTGCCTGCCAGAGGACC---AAACTCTGAATTTTAGTGATGTCTGA
GTACTATATAATAGTTAAAACTTTCAACAACGGATCTCTTGGTTCTGGCATCGATGAAGA
ACGCAGCGAAATGCGATAAGTAATGTGAATTGCAGAATTCAGTGAATCATCGAATCTTTG
AACGCACATTGCGCCCGGTGGTATTCCGCCGGGCATGCCTGTTCGAGCGTCATTATAACC
ACTCAAGCCTAGCTTGGTATTGGGGT-TCGCGGT--CCCGCGGCCCCTAAAATCAGTGGC
GGTGCCGGTG-GGCTCTAAGCGTAGTAA-ATCTCCTCGCTATAGGGTCC-----------
-----------------CC--------------------------CCGGTTGCCCGC-G
GTTGACCTCGGATCAGGTAGGGATACCCGCTGAACTTAAGCATATCAATAAGCGGAGGAA
AAGAAACCAACAGGGATTACCTCAGTAACGGCGAGTGAAGCGGTAACAGCTCAAATTTGA
AAGCTGCC-----AACAGGCCGCGTTGTAATTTGTAGAAGATGCTTTGGGGGTCGGCCTA
GTCTAAGTTCCTTGGAACAGGACGTCATAGAGGGTGAGAATCCCGTATGTGATTAG-TGC
CGGCTCCCGTGTAAAGCTCTTTCGACGAGTCGAGTTGTTTGGGAATGCAGCTCAAAATGG
GTGGTATATTTCATCTAAAGCTAAATATTGGCCAGAGACCGATAGCGCACAAGTAGAGTG
ATCGAAAGATGAAAAGCACTTTGGAAAGAGAGTTAAACAGTACGTGAAATTGTTGAAAGG
GAAGCGCTTGCAACCAGACTTGCAGGCGGTCGATCATCCGAGGTTC-TCCCCGGTGCACT
CGATCGTCT-TCAGGCCAGCATCGGTTTTGGTGGCGGGATAAAGGCTCTAGGAATGTGGC
TC--TTC------GGAGTGTTATAGCCTAGGGTGCAATGCCGCCTACCGGGACCGAGGAC
CGCGCTTC-GGCTAGGATGCTGGCGTAATGGTTGTAAGCGGCCCGTCTTGAAACACGGAC
CAAGGAGTCTAACATCTATGCGAGTGTTTGGGTGTCAAACCCATACGCGTAATGAAAGTG
AACGGAGGTGAGAGCCCTTTAGGGCGCATCATCGACCGATCCTGATGTCTTCGGATGGAT
TTGAGTAAGAGCATAGCTGTTGGGACCCGAAAGATGGTGAACTATGCGTGAATAGGGTGA
AGCCAGAGGAAACTCTGGTGGAGGCTCGCAGCGGTTCTGACGTGCAAATCGATCGTC-AA
ATTTGCGTATAGGGGC-GAAAGACTAATCG-------------------------------
------------------------------GACATGAGT-TTCTCAGAGCAATCCGGC
ATACAAGGCAGCCGTTTCAATTCGAGACCCGAAGCGTAGGTTCGATACGATATGGCGACT
TTGCAAGCCCAAGATGATCTGCGACAGCGATGTCCCTAATGATGAT---GAATTTGGTGG
TGATCCAAAAGAAGCTGTTAAA---CGTTCTCATGGAGGTTGTGGCAATACTCAACCCGA
GGTTCGCCAGCAAGCTTTACAGCTCTGGGGAACATGGAAGATGCCCAAGGATGAAGAAAA
CGAGGGTG---CGACTCAA---GAAAAGAGACAGATTACTCCAGAGATGGCTCTGAACGT
CTTCCGCAGCATGTCCTCGGCTGAGATTCGCGATTTGGGCTTGAGCAATGACTATGCACG
CCCTGACTGGCTTATCATTACTGTCCTTCCCGTTCCTCCCCACCTGTTCGACCAAGTAT
TTCCATGGATGGTACAAGCACAGGAATGCGCGGAGAGGATGATTTGACATACAAGCTTGG
TGATATTATCCGTGCAAATGGTTTCATTAAGC-AAGCCCAACAAGAGGG
```

Figure 4E

```
Acidoradicia_panicicola_WSF1-R37
GTGTCTA-----------------------------------------------------
------------------------------------------------------------
------TCTACTCTTGT-TGCTTTGGCAGGCCGTGG-CCT-CCAC--CGC----GGGCTC
TGCCTGC-----GTGTGCCTGCCAGAGGACC---AAACTCTGAATTTTAGTGATGTCTGA
GTACTATATAATAGTTAAAACTTTCAACAACGGATCTCTTGGTTCTGGCATCGATGAAGA
ACGCAGCGAAATGCGATAAGTAATGTGAATTGCAGAATTCAGTGAATCATCGAATCTTTG
AACGCACATTGCGCCCGGTGGTATTCCGCCGGGCATGCCTGTTCGAGCGTCATTATAACC
ACTCAAGCCTGGCTTGGTATTGGGAC-TCGCGGT--TCCGCGGCCCCTAAAATCAGTGGC
GGTGCCGGTG-GGCTCTAAGCGTAGTAA-ATCTCCTCGCTATAGGGTCC-----------
----------------CT------------------------CCGGTTGCCTGC--
------------------------------------------------------------
------------------------------------------------------------
------------------------------------------------------------
------------------------------------------------------------
---------TGTAAAGCTCTTTCGACGAGTCGAGTTGTTTGGGAATGCAGCTCAAAATGG
GTGGTATATTTCATCTAAAGCTAAATATTGGCCAGAGACCGATAGCGCACAAGTAGAGTG
ATCGAAAGATGAAAAGCACTTTGGAAAGAGAGTTAAACAGTACGTGAAATTGTTGAAAGG
GAAGCGCTTGCAACCAGACTTGCAGGCGGTCGATCATCCGAGGTTC-TCCCCGGTGCACT
CGATCGTCT-TCAGGCCAGCATCGGTTTTGGTGGCGGGATAAAGGCTCTAGGAATGTGGC
TC--TTC------GGAGTGTTATAGCCTAGGGTGCAATGCCGCCTACCGGGACCGAGGAC
CGCGCTTC-GGCTAGGATGCTGGCGTAATGGTTGTAAGCGGCCCGTCTTGAAACACGGAC
CAAGGAGTCTAACATCTATGCGAGTGTTTGGGTGTCAAACCCATACGCGTAATGAAAGTG
AACGGAGGTGAGAGCCCTTTAGGGCGCATCATCGACCGATCCTGATGTCTTCGGATGGAT
TTGAGTAAGAGCATAGCTGTTGGGACCCGAAAGATGGTGAACTATGCGTGAATAGGGTGA
AGCCAGAGGAAACTCTGGTGGAGGCTCGCAGCGGTTCTGACGTGCAAATCGATCGTC-AA
ATTTGCGTATAGGGGC-GAAAGACTAATCGGCTAGACAGGGTCAGTTCG---CCCGAAAA
GGGTGGCGGATCTACT--TGTTC-TTTGTGCTGACATGAGT-TTCTCAGAGCAATCCGGC
ATACAAGGCAGCCGTTTCAATTCGAGACCCGAAGCGTAGGTTCGATACGATATGGCGACT
TTGCAAGCCCAAGATGATCTGCGACAGCGATGTCCCTAATGATGAT---GAATTTGGTGG
TGATCCAAAGGAAGCTGTTAAA---CGTTCTCATGGAGGTTGTGGCAATACTCAACCCGA
GGTTCGCCAGCAAGCTTTACAGCTCTGGGGAACATGGAAGATGCCCAAGGATGAAGAAAA
CGAGGGTG---CGACTCAA---GAAAAGAGACAGATTACTCCAGAGATGGCTTTGAATGT
CTTCCGCAGCATGTCCTCGGCTGAGATTCGCGATTTGGGCTTGAGCAATGACTATGCACG
CCCTGATTGGCTTATCATTACTGTCCTTCCCGTTCCTCCCCCACCTGTTCGACCAAGTAT
TTCCATGGATGGTACAAGCACAGGAATGCGCGGAGAGGATGATTTGACATACAAGCTTGG
TGATATTATCCGTGCAAACGGCAACGTTAAGC-AAGCCCAACAAGAGGG
```

Figure 4F

Acidoradicia_taeda_CM14-P64
GTGTCTA-------------------------------------------------------
---------------------------------------------------------------
------TTTACTCTTGT-TGCTTTGGCAGGCCGTGG-CCT-CCAC--CGT----GGGCTC
TGTCTAC-----GCGTGTCTGCCAGAGGACC---AAACTCTGAATTTTAGTGATGTCTGA
GTACTATACAATAGTTAAAACTTTCAACAACGGATCTCTTGGTTCTGGCATCGATGAAGA
ACGCAGCGAAATGCGATAAGTAATGTGAATTGCAGAATTCAGTGAATCATCGAATCTTTG
AACGCACATTGCGCCCGGTGGTATTCCGCCGGGCATGCCTGTTCGAGCGTCATTATAACC
ACTCAAGCCTGGCTTGGTATTGGGGT-ACGCGGC--TTCGCGGCTCCTAAAATCAGTGGC
GGTGCCGGTG-GGCTCTAAGCGTAGTAA-ATCTCCTCGCTATAGGGTTC-----------
-----------------CT---------------------------CTGGTTGCTTGC--
---------------------------------------------------------------
---------------------------------------------------------------
---------------------------------------------------------------
---------------------------------------------------------------
---------------------------------------------------------------
---------------------------------------------------------------
---------------------------------------------------------------
-----------------------------------------------------GGTGCACT
CGATCGTCT-TCAGGCCAGCATCGGTTTCGGTGGCGGGATAAAGGCTCTAGGAATGTGGC
TC--TTC------GGAGTGTTATAGCCTAGGGTGCAATGCCGCCTACCGGGACCGAGGAC
CGCGCTTC-GGCTAGGATGCTGGCGTAATGGTTGTAAGCGGCCCGTCTTGAAACACGGAC
CAAGGAGTCTAACATCTATGCGAGTGTTTGGGTGTCAAACCCATACGCGTAATGAAAGTG
AACGGAGGTGAGAGCCCTTTAGGGCGCATCATCGACCGATCCTGATGTCTTCGGATGGAT
TTGAGTAAGAGCATAGCTGTTGGGACCCGAAAGATGGTGAACTATGCGTGAATAGGGTGA
AGCCAGAGGAAACTCTGGTGGAGGCTCGCAGCGGTTCTGACGTGCAAATCGATCGTC-AA
ATTTGCGTATAGGGGC-GAAAGACTAATCGGCTAGACAGGGTCAGTTCG---CCCGAATA
GGGTGGCAGATCTACT--TGTTC-TTTGTGCTGACATGAGT-ATCTCAGAGTAATCCGGC
GTACAAGGCAGCTGTTTCGATTCGGGACCCGAAGCGTAGGTTCGATACGATATGGCGACT
TTGCAAGCCCAAGATGATCTGCGACAGCGATGTCCCTAACGACGAT---GAATTTGGTGG
TGATCCAAAGGAAGCTGTCAAG---CGTTCTCATGGAGGTTGTGGTAATACTCAGCCCGA
GGTTCGTCAGCAGGCTCTACAGCTCTGGGGTACATGGAAGATGCCAAAGGATGAAGAAAA
TGAGGGGT---CAAGTCAA---GAAAAGAGACAAATCACTCCAGAGATGGCTTTAAATGT
CTTCCGAAGCATGTCCTCGGCTGAGATTCGCGACCTGGGCCTGAGCAACGACTACGCTCG
TCCCGACTGGCTCATCATTACAGTCCTTCCTGTTCCTCCTCCGCCCGTTCGCCCTAGTAT
TTCTATGGATGGCACAAGCACGGGAATGCGTGGAGAAGATGATTTGACCTACAAGCTTGG
TGATATAATTCGTGCCTACGGCAACGTTATGCAAAGCACAACAAGAATG

Figure 4G

Acidoradicia_taeda_WSF14-P22
GTGTCTA-----------------------------------------------------
------------------------------------------------------------
------TTTACTCTTGT-TGCTTTGGCAGGCCGTGG-CCT-CCAC--CGT----GGGCTC
TGTCTAC-----GCGTGTCTGCCAGAGGACC---AAACTCTGAATTTTAGTGATGTCTGA
GTACTATACAATAGTTAAAACTTTCAACAACGGATCTCTTGGTTCTGGCATCGATGAAGA
ACGCAGCGAAATGCGATAAGTAATGTGAATTGCAGAATTCAGTGAATCATCGAATCTTTG
AACGCACATTGCGCCCGGTGGTATTCCGCCGGGCATGCCTGTTCGAGCGTCATTATAACC
ACTCAAGCCTGGCTTGGTATTGGGGT-ACGCGGC--TTCGCGGCTCCTAAAATCAGTGGC
GGTGCCGGTG-GGCTCTAAGCGTAGTAA-ATCTCCTCGCTATAGGGTTC-----------
-----------------CT--------------------------CTGGTTGCTTGC--
------------------------------------------------------------
------------------------------------------------------------
------------------------------------------------------------
------------------------------------------------------------
------------------------------------------------------------
------------------------------------------------------------
-----GCTTGCAACCAGACTTGCAGGCGGTCGATCATCCGAGGTTC-TCCCCGGTGCACT
CGATCGTCT-TCAGGCCAGCATCGGTTTCGGTGGCGGGATAAAGGCTCTAGGAATGTGGC
TC--TTC------GGAGTGTTATAGCCTAGGGTGCAATGCCGCCTACCGGGACCGAGGAC
CGCGCTTC-GGCTAGGATGCTGGCGTAATGGTTGTAAGCGGCCCGTCTTGAAACACGGAC
CAAGGAGTCTAACATCTATGCGAGTGTTTGGGTGTCAAACCCATACGCGTAATGAAAGTG
AACGGAGGTGAGAGCCCTTTAGGGCGCATCATCGACCGATCCTGATGTCTTCGGATGGAT
TTGAGTAAGAGCATAGCTGTTGGGACCCGAAAGATGGTGAACTATGCGTGAATAGGGTGA
AGCCAGAGGAAACTCTGGTGGAGGCTCGCAGCGGTTCTGACGTGCAAATCGATCGTC-AA
ATTTGCGTATAGGGGC-GAAAGACTAATCGGCTAGACAGGGTCAGTTCG---CCCGAATA
GGGTGGCAGATCTACT--TGTTC-TTTGTGCTGACATGAGT-ATCTCAGAGTAATCCGGC
GTACAAGGCAGCTGTTTCGATTCGGGACCCGAAGCGTAGGTTCGATACGATATGGCGACT
TTGCAAGCCCAAGATGATCTGCGACAGCGATGTCCCTAACGACGAT---GAATTTGGTGG
TGATCCAAAGGAAGCTGTCAAG---CGTTCTCATGGAGGTTGTGGTAATACTCAGCCCGA
GGTTCGTCAGCAGGCTCTACAGCTCTGGGGTACATGGAAGATGCCAAAGGATGAAGAAAA
TGAGGGGT---CAAGTCAA---GAAAAGAGACAAATCACTCCAGAGATGGCTCTAAATGT
CTTCCGAAGCATGTCCTCGGCTGAGATTCGCGACCTGGGCCTGAGCAACGACTACGCTCG
TCCCGACTGGCTCATCATTACAGTCCTTCCTGTTCCTCCTCCGCCCGTTCGCCCTAGTAT
TTCTATGGATGGCACAAGCACGGGAATGCGTGGAGAAGATGATTTGACCTACAAGCTTGG
TGATATAATTCGTGCAAACGGCAACGTTAAGC-AAGCACAACAAGAAGG

Figure 4H

Acidoradicia_taeda_WSF14-P13
GTGTCTA-----------------------------------------------------
------------------------------------------------------------
------TTTACTCTTGT-TGCTTTGGCAGGCCGTGG-CCT-CCAC--CGT----GGGCTC
TGTCTAC-----GCGTGTCTGCCAGAGGACC---AAACTCTGAATTTTAGTGATGTCTGA
GTACTATACAATAGTTAAAACTTTCAACAACGGATCTCTTGGTTCTGGCATCGATGAAGA
ACGCAGCGAAATGCGATAAGTAATGTGAATTGCAGAATTCAGTGAATCATCGAATCTTTG
AACGCACATTGCGCCCGGTGGTATTCCGCCGGGCATGCCTGTTCGAGCGTCATTATAACC
ACTCAAGCCTGGCTTGGTATTGGGGT-ACGCGGC--TTCGCGGCTCCTAAAATCAGTGGC
GGTGCCGGTG-GGCTCTAAGCGTAGTAA-ATCTCCTCGCTATAGGGTTC-----------
-----------------CT-----------------------CTGGTTGCTTGC--
------------------------------------------------------------
------------------------------------------------------------
------------------------------------------------------------
------------------------------------------------------------
------------------------------------------------------------
------------------------------------------------------------
-----------
-----GCTTGCAACCAGACTTGCAGGCGGTCGATCATCCGAGGTTC-TCCCCGGTGCACT
CGATCGTCT-TCAGGCCAGCATCGGTTTCGGTGGCGGGATAAAGGCTCTAGGAATGTGGC
TC--TTC------GGAGTGTTATAGCCTAGGGTGCAATGCCGCCTACCGGGACCGAGGAC
CGCGCTTC-GGCTAGGATGCTGGCGTAATGGTTGTAAGCGGCCCGTCTTGAAACACGGAC
CAAGGAGTCTAACATCTATGCGAGTGTTTGGGTGTCAAACCCATACGCGTAATGAAAGTG
AACGGAGGTGAGAGCCCTTTAGGGCGCATCATCGACCGATCCTGATGTCTTCGGATGGAT
TTGAGTAAGAGCATAGCTGTTGGGACCCGAAAGATGGTGAACTATGCGTGAATAGGGTGA
AGCCAGAGGAAACTCTGGTGGAGGCTCGCAGCGGTTCTGACGTGCAAATCGATCGTC-AA
ATTTGCGTATAGGGGC-GAAAGACTAATCGGCTAGACAGGGTCAGTTCG---CCCGAATA
GGGTGGCAGATCTACT--TGTTC-TTTGTGCTGACATGAGT-ATCTCAGAGTAATCCGGC
GTACAAGGCAGCTGTTTCGATTCGGGACCCGAAGCGTAGGTTCGATACGATATGGCGACT
TTGCAAGCCCAAGATGATCTGCGACAGCGATGTCCCTAACGACGAT---GAATTTGGTGG
TGATCCAAAGGAAGCTGTCAAG---CGTTCTCATGGAGGTTGTGGTAATACTCAGCCCGA
GGTTCGTCAGCAGGCTCTACAGCTCTGGGGTACATGGAAGATGCCAAAGGATGAAGAAAA
TGAGGGGT---CAAGTCAA---GAAAAGAGACAAATCACTCCAGAGATGGCTCTAAATGT
CTTCCGAAGCATGTCCTCGGCTGAGATTCGCGACCTGGGCCTGAGCAACGACTACGCTCG
TCCCGACTGGCTCATCATTACAGTCCTTCCTGTTCCTCCTCCGCCCGTTCGCCCTAGTAT
TTCTATGGATGGCACAAGCACGGGAATGCGTGGAGAAGATGATTTGACCTACAAGCTTGG
TGATATAATTCGTGCAAACGGCAACGTTAAGC-AAGCACAACAAGAAGG

Figure 4I

```
Cudoniella_clavus_DQ491502
-------------------------------------AAAAGTCGTAACAAGGTTTCCGTAG
GTGAACCTGCGGAAGGATCATTACAGTGTTCCCTGCCCTCACGGGTAGAAACGCCACCCT
TGTATATATTATCTTGT-TGCTTTGGCGGGCCGCCT-TTAGGCAC----T----GGCTTC
GGCTGGC-----TCGCGCCCGCCAGAGAACCCC-AAACTCTAAATGTTAGTGTCGTCTGA
GTACTATCTAATAGTTAAAACTTTCAACAACGGATCTCTTGGTTCTGGCATCGATGAAGA
ACGCAGCGAAATGCGATAAGTAATGTGAATTGCAGAATTCAGTGAATCATCGAATCTTTG
AACGCACATTGCGCCCCTTGGTATTCCGGGGGGCATGCCTGTTCGAGCGTCATTTAAACC
AATCCAGCAT-GCTGGGTCTTGGGCCTTCGCCTC--TGGGCGGGCCTCAAAATTAGTGGC
GGTGCCACCT-GGCTCTACGCGTAGTAA-TTCTTCTCGCGATGGAGTCCCAGGTGGAAGC
TTGCCAACAACCCCAAATTCTTTTAAAGGTTGACCTCGGATCAGGTAGGGATACCCGC--
-----------------------------------CTAAGCATATCAATAAGCGGAGGAA
AAGAA?CCAACAGGGATTACCTCAGTAACGGCGAGTGAAGCGGTAACAGCTCAAATTTGA
AATCTGGCTCTTTCAGGGTCCGAGTTGTAATTTGTAGAAGATGCTTCGGGTGTGGCTCCG
GTCTAAGTTCCTTGGAACAGGACGTCATAGAGGGTGAGAATCCCGTATGTGACTGGTTGC
CTTCGCCCATGTGAAGCTCTTTCGACGAGTCGAGTTGTTTGGGAATGCAGCTCTAAATGG
GTGGTAAATTTCATCTAAAGCTAAATATTGGCCAGAGACCGATAGCGCACAAGTAGAGTG
ATCGAAAGATGAAAAGCACTTTGGAAAGAGAGTTAAACAGTACGTGAAATTGTTGAAAGG
GAAGCGCTTGCAACCAGACTTGCACGTCGTCGATCATCCTCAGTTC-TCTGGGGTGCACT
CGGCGGTGT-TCAGGCCAGCATCGGTTTCGGTGGTGGGATAAAGGCCTTGGGAATGTGGC
TCCTCTC----GGGGAGTGTTATAGCCCTCGGTGCAATGCCGCCTACTGGGACCGAGGAC
CGCGCTTC-GGCTAGGATGCTGGCGTAATGGTTGTAAGCGACCCGTCTTGAAACACGGAC
CAAGGAGTCTAACATCTATGCGAGTGTTTGGGTGTTAAACCCATACGCGTAATGAAAGTG
AACGGAGGTGAGAACCCTTTAGGGTGCATCATCGACCGATCCTGATGTCTTCGGATGGAT
TTGAGTAAGAGCATAGCTGTTGGGACCCGAAAGATGGTGAACTATGCCTAAATAGGGTGA
AGCCAGAGGAAACTCTGGTGGAGGCTCGCAGCGGTTCTGACGTGCAAATCGATCGTC-AA
ATTTGGGTATAGGGGC-GAAAGACTAATCGACTAGACAGGGTCAGTTGG---CCCGCATA
GCGTGGCATGTCT-TT--TGTGCCTTTGTGCTAACA-GAATGATTTCAGAGCAATCCAGC
GTACAAGGCAGCTGTTTCTATCCGAGATCCAAAGCGTAGATTTGATACAATATGGCGACT
GTGCAAGCCGAAGATGATTTGCGAGGGTGATGTGCAGGCGAATGAGGAAGAATTTGATCC
CAACCAAAAGAACC---GAAG---CCGTCGCACGGAGGGTGTGGTAATTCTCAGCCTGA
AGTGCGTCAGACTGCTTTGCAACTATGGGGAACATGGAAAGTGCCTAAGGACGAAGATAA
CGAGAGTCAGTCGCCG------GAAAAGAGGCAGATTACTCCCGAAATGGCTCTGGCTGT
CTTCCGAAGCATTTCCACGGAAGAAATCTTC?ACCTTGGCCTGAGTAATGATTATGCGCG
TCCCGAATGGATGATCATAACGGTTCTCCCAGTTCCTCCACCACCTGTTCGACCCAGTAT
TTCAATGGATGGCACTGGTCAGGGCATGCGCGGAGAGGACGATTTGACATATAAGTTGGG
AGATATCATCCGGGCAAACGGCAATGTGCGGC-AAGCTCAGCAGGAAGG
```

Figure 4J

Dermea_acerina_AF141164
GTGTCGT-----------------------------------------------------
------------------------------------------------------------
------TATACCTTCGT-TGCTTTGGTGGGCCGCTGGGCTTCGGCCTGGCTCCTGGCTCC
GGCTAGG-----GAGTGCCCGCCAGAGGACC-TTAAAACCTGAA-GTTAGTGTCGTCTGA
GTACTATACAATAGTTAAAACTTTCAACAACGGATCTCTTGGTTCTGGCATCGATGAAGA
ACGCAGCGAAATGCGATAAGTAATGTGAATTGCAGAATTCAGTGAATCATCGAATCTTTG
AACGCACATTGCGCCCCTTGGTATTCCGGGGGGCATGCCTGTTCGAGCGTCATTACAACC
-CTCAAGCTCTGCTTGGTATTGGGCG-TCACCGGGTTCGGTGTGCCTTAAAATCAGTGGC
GGCGCCGTCT-GGCTCTAAGCGTAGTAC-ATACTCTCGCTATGGACGCC-----------
-----------------TG------------------------GCGGATGCTTGC--
------------------------------------------------------------
----------------------------------------------------------GA
AATCTGGGTCTTTTAGGCTCCGAGTTGTAAT?TGTAGAAGATGCTTCGGGTGCGGCTCCG
GTCTAAGTTCCTTGGAACAGGACGTCATAGAGGGTGAGAATCCCGTATGTGATCGGGGGC
TTGCGCCCATGTGAAGCTCTTTCGACGAGTCGAGTTGTTTGGGAATGCAGCTCAAAATGG
GTGGTATATTTCATCTAAAGCTAAATATTGGCCAGAGACCGATAGCGCACAAGTAGAGTG
ATCGAAAGATGAAAAGCACTTTGGAAAGAGAGTTAAACAGTACGTGAAATTGTTGAAAGG
GAAGCGCTTGCAACCAGACTTGGGCGGGGTTGATCATCTAGGGTTC-TCCCTAGTGCACT
CGACCTCGC-ACAGGCCAGCATCGGTTCCGGTGGTTGGATAAAGGCCTTGGGAATGTAGC
TTCTTTC----GGGGAGTGTTATAGCCCTCGGTGCAATGCAGCCTACTGGGACCGAGGAC
CGCGCTTC-GGCTAGGATGCTGGCGTAATGGTTGTAAGCGACCCGTCTTGAAACACGGAC
CAAGGAGTCTAACATCTATGCGAGTGTTTGGGTGTCAAACCCATACGCGTAATGAAAGTG
AACGGAGGTGAGAACCCTTAAGGGTGCATCATCGACCGATCCTGATGTCTTCGGATGGAT
TTGAGTAAGAGCATAGCTGTTGGGACCCGAAAGATGGTGAACTATGCCTGAATAGGGTGA
AGCCAGAGGAAACTCTGGTGGAGGCTCGCAGCGGTTCTGACGTGCAAATCGATCGTC-AA
ATTTGGGTATAGGGGC-GAAAGACTAATCGGCTAGACAGGGTCAGTTCT---CCCACGTA
GCGTGGGGAGCATGAT--TGTTTCTGTGTGCTAACGTCAAT-ATCTCAGAGTAATCCAGC
GTACAAAGCAGCCGTTTCGATTCGAGACCCGAAGCGTAGGTTCGATACGATCTGGCGACT
TTGCAAGCCCAAGATGATCTGTGATAGCGATTTGACTGCCGCCGATGATGATTTCAATGC
AGACCCGAAGGAAGCCGCAAAG---CGCTCGCACGGTGGATGTGGAAATACTCAGCCTGA
GGTGCGCCAGTCGGCCTTGCAGCTGTGGGTACATGGAAGGTTCCAAAGGATGAAGACAA
TGATGGTGCTACTGCC------GAAAAGAAGCAGATCACTGCAGAGATGGCCCTGAATGT
CTTCCGAAGCATTTCCACTTCTGAGATCCAAGACCTTGGCTTGAGTACTGACTATGCGCG
ACCTGAATGGATGATCATTACGGTTCTTCCAGTTCCTCCTCCACCTGTTCGACCGAGTAT
TTCGATGGACGGCACTGGGCAAGGCATGCGAGGAGAGGATGATTTGACATACAAGCTTGG
CGATATCATTCGTGCGAATGGCAACGTTCGAC-AGGCCCAGCAAGAAGG

Figure 4K

Hyaloscypha_aureliella_JN943611
GTGCCTGGTCTAAGATATAGTCGGTCCCGGCCCGAAAGGGCCGGGGAACAGCGTCCGTAG
GTGAACCTGCGGAAGGATCATTACAGAGTTCATGCCCTCACGGGTAGATCTCCCACCCTT
GAATACCTTACCTTTGTCTGCTTTGGCGGGCCACGT-----CCGCG-TGC----CGGCTC
CGGCTGG-----TTGCGCCCGCCAGAGGACC--CAAACTCTTTTGTTTAGTGATGTCTGA
GTACTATATAATAGTTAAAACTTTCAACAACGGATCTCTTGGTTCTGGCATCGATGAAGA
ACGCAGCGAAATGCGATAAGTAATGTGAATTGCAGAATTCAGTGAATCATCGAATCTTTG
AACGCACATTGCGCCCCTTGGTATTCCGAGGGGCATGCCTGTTCGAGCGTCATTATGACC
ACTCAAGCCTGGCTTGGTGTTGGGGT-CCGCGGT--CCCGCGGCCCTTAAAATCAGTGGC
GGCGCCATCT-GGCTCTCAGCGTAGTAA-TACTCCTCGCTACAGGGTCC----------
------------------------------------------------------------C--
-------------------------------ACGGCGAGTGAAGCGGCAACAGCTCAAATTTGA
AATCTGGCTCCTGCGGGGCCCGAGTTGTAATTTGTAGAAGATGCTTTGAGCGTGGCTCCG
GTCTAAGTTCCTTGGAACAGGACGTCATAGAGGGTGAGAATCCCGTATGTGACTGGGTGC
CTCCGTTCGTGTAAAGCTCTTTCGACGAGTCGAGTTGTTTGGGAATGCAGCTCAAAATGG
GTGGTAAATTTCATCTAAAGCTAAATATTGGCCAGAGACCGATAGCGCACAAGTAGAGTG
ATCGAAAGATGAAAAGCACTTTGGAAAGAGAGTTAAACAGTACGTGAAATTGTTGAAAGG
GAAGCGCTTGCAACCAGACTTGCCCGCTGCTGATCATCCGAGGTTC-TCCCCGGTGCACT
CGGCAGCGA-TCAGGCCAGCATCGGTTCTGGTGGGCGGATAAAGGCCTTGGGAATGTAGC
TTCCTTC----GGGGAGTGTTATAGCCCTCGGTGCAATGCGCCCTACCGGGACCGAGGAC
CGCGCTTC-GGCTAGGATGCTGGCGTAATGGTTGTAAGCGACCCGTCTTGAAACACGGAC
CAAGGAGTCTAACATCTATGCGAGTGTTTGGGTGTTAAACCCATACGCGTAATGAAAGTG
AACGGAGGTGAGAACCCTTAAGGGTGCATCATCGACCGATCCTGATGTCTTCGGATGGAT
TTGAGTAAGAGCATAGCTGTTGGGACCCGAAAGATGGTGAACTATGCCTGAATAGGGTGA
AGCCAGAGGAAACTCTGGTGGAGGCTCGCAGCGGTTCTGACGTGCAAATCGATCGTC-AA
ATTTGGGTATAGGGGC-GAAAGACTAATCGACTTGACAGAGTCAGTGTG---CCTGAACT
TGAGGGCCGAGTTTCTTGTGTGCCTTTATGCTAACTTCATG-ATTGCAGAACAATCCGGC
GTACAAAGCTGCTGTGAGCATTCGAGACCCGAAACGTCGGTTCGATGCGATATGGCGACT
TTGCAAACCGAAATTGATCTGCGACAGTGATTTGAGTGCAGGGGACGAGGGCTTCGACGC
TGACCCAAAGGAACTTGCGAAA---CGCTCGCATGGAGGATGTGGAAATAAACAACCAGA
AGTGCGCCAGAGCGCCCTTCAGCTCACCGGCACTTTTAAGCCTTCGAAGGAAGAACTCAG
CGAGGGC------ATGCAGCCAGAAAAGAAGTTAATCACCCCAGAGGCAGCTCTGCACAT
CTTCCGAAGCATTTCCTCCGACGAGATTCGCGACTTAGGCCTGAGCAATGATTATGCGCG
CCCGGAATGGATGATCATCACAGTCCTTCCCGTGCCTCCTCCTCCTGTTCGGCCCAGTAT
TTCTATGGATGGCACTGGTCAAGGTATGCGAGGAGAGGATGATTTGACATACAAACTTGG
TGACATCATCCGTGCGAATGGAAACGTTCGAC-AGGCGCATCAAGAGGG

Figure 4L

Lachnum_virgineum_DQ491485
GTATCAT-----------------------------------------------------
------------------------------------------------------------
------TATAGAAT-GT-TGCTTTGGCGGGCTGCGTGCCTAGCAC----------GCCTC
GATTCGCGTCGAGCGCGCCCGCCAGAGGACCCCTAAACTSTGAATGTTAGTGTCGTCTGA
GTACTATTAAATAGTTAAAACTTTCAACAACGGATCTCTTGGTTCTGGCATCGATGAAGA
ACGCAGCGAAATGCGATAAGTAATGTGAATTGCAGAATTCAGTGAATCATCGAATCTTTG
AACGCACATTGCGCCCCTTGGTATTCCGGGGGGCATGCCTGTTCGAGCGTCATTTATACC
AATCTARCCTGGCTAGGTGTTGGGCC-TCGCCAG--TTGGCGGGCCTTAAAACTAGTGGC
GGTGCTCTTC-AGCTCTACGCGTAGTAA--TTTTCTCGCTATAGGGTCT-----------
----------------------------------------GGGGAGATGCTTGC--
------------------------------------------------------------
-------CCACAGGGATTACCTCAGTAACGGCGAGTGAAGCGGTAACAGCTCAAATTTGA
AATCTGGCTCTTTTAGGGTCCGAGTTGTAATTTGTAGAAGATGCTTTGGGTGTGGCCCTG
GTCTAAGTTCCTTGGAACAGGACGTCATAGAGGGTGAGAATCCCGTATGTGACTAGGTGC
CTTCGCCCGTGTAAAGCTCTTTCGACGAGTCGAGTTGTTTGGGAATGCAGCTCAAAATGG
GTGGTAAATTTCATCTAAAGCTAAATATTGGCCAGAGACCGATAGCGCACAAGTAGAGTG
ATCGAAAGATGAAAAGCACTTTGGAAAGAGAGTTAAACAGTACGTGAAATTGTTGAAAGG
GAAGCGCTTGCAACCAGACTTAGTTGCTGCCGATCATCCAGGGTTC-TCCCTGGTGCACT
CGGTAGTAT-CTAGGCCAGCATCGGTTTGGGTGGTGGGATAAAGGCCTTGGGAATGTAGC
TTCTTTC----GGGGAGTGTTATAGCCCTCGGTGCAATGCCGCCTACCCGGACCGAGGAC
CGCGCTTC-GGCTAGGATGCTGGCGTAATGGTTGTAAGCCACCCGTCTTGAAACACAGAC
CAAGGAGTCTAACATCTATGCGAGTATTTGGGTGTTAAACCCATATGCGTAATGAAAGTG
AACGGAGGTGAGAACCCTTAAGGGTGCATCATCGACCGATCCTGATGTCTTCGGATGGAT
TTGAGTAAGAGCATAGCTGTTGGGACCCGAAAGATGGTGAACTATGCCTAAATAGGGTGA
AGCCAGAGGAAACTCTGGTGGAGGCTCGCAGCGGTTCTGACGTGCAAATCGATCGTC-AA
ATTTGGGTATAGGGC-GAAAGACTAATCGGCTTGACAGGGTCAGTTCA----CCGTAAA
AGGTGTTGGCTTCGCT--TGTTC-TTTTTGCTGACA-GAAT-ATCTCAGGGTAATCCCCA
GTACAAGGCAGCTGTTTCTATTCGTGATCCAAAGCGTAGATTCGATACAATCTGGCGACT
TTGCAAGCCCAAGATGATCTGCGATAGCGATGTCCCTAATGAAGAT---GAATTCGGTGG
TGATCCAAAGGAAGCTGTGAAG---CGTTCGCATGGAGGATGTGGAAATACACAACCTGA
GGTCCGCCAACAGGCATTGCAGCTCTGGGGAACATGGAAGATGCCAAAGGATGAGGAGAA
CGAGGGTGG--CAACTCG----GAGAAGAGACAAATTACACCAGAGATGGCTCTCAATGT
CTTCAGATCCATGTCTTCTGAAGAAATTCGCGACCTCGGTCTCAGCAACGATTATGCACG
TCCTGACTGGTTGATTATTACAGTTCTTCCAGTTCCGCCTCCTCCTGTTCGACCCAGTAT
TTCCGTGGACGGCACGAGCACAGGTATGCGCGGAGAGGATGATTTGACATACAAGCTTGG
TGATATCATTCGTGCCAACGGCAATGTGAAGC-AGGCTCAACAAGAAGG

Figure 4M

Loramyces_macrosporus_DQ471005
GTGTCTA---------------------------------------------------
----------------------------------------------------------
------TATACTCTTGT-TGCTTTGGCAGGCCGTGG-TCT-CGACCCTGT----GGGCTT
TGCCTGC-----ATGTGCCTGCCAGAGGACC---AAACTCTGAATTTTAGTGATGTCTGA
GTACTATATAATAGTTAAAACTTTCAACAACGGATCTCTTGGTTCTGGCATCGATGAAGA
ACGCAGCGAAATGCGATAAGTAATGTGAATTGCAGAATTCAGTGAATCATCGAATCTTTG
AACGCACATTGCGCCCGGTGGTATTCCGCCGGGCATGCCTGTTCGAGCGTCTCTATCAAC
CTACACGCTCCGCGTGGAATTGGGGC-CTGCGGTCACCTGCAGCCCTAGAACCCAACAGC
GATACCGAGT-GGTCCTCAGCGTAGTAC--ATACCCCGCTACAGGCCTC-----------
-----------------CT------------------------CTGGTGTTCTGC--
----------------------------------------------------------
----------------------------------------------------------
----------------------------------------------------------
----------
-TGGTCTATATCATCTAAAGCTACATATTGGCCAGAGGCCGATAGCGCACAAGTAGAGTG
ATCGAAAGATG?AAAGCACTTTGGAAAGAGAGTTAAACAGTACGTGAAATTGTTGAAAGG
GAAGCGCTTGCAATCAGACTTGCAGGCGGTTGATCATCCGGGGTTT-TCCCCGGTGCACT
CGATCGTCT-TCAG??CAGCATCAGTTCTCGTGGTGGGATAAAGGCTGTGAGAATGTGGC
TC--TTC------GGAGTGTTATAGCTCACGGTGCAATGCTGCCTACGGGGACTGAGGAC
CGCGCTTC-GGCTAGGATGCTGGCGTAATGGTTGTAAGCGACCCGTCTTGAAACACGGAC
CAAGGAGTCTAACATCTATGCGAGTGTTTGGGTGTCAAACCCATACGCGTAATGAAAGTG
AACGGAGGTGAGAACCCTTTAGGGCGCATCATCGACCGATCCTGATGTCTTCGGATGGAT
TTGAGTAAGAGCATAGCTGTTGGGACCCGAAAGATGGTGAACTATGCGTGAATAGGGTGA
AGCCAGAGGAAACTCTGGTGGAGGCTCGCAGCGGTTCTGACGTGCAAATCGATCGTC-AA
ATTTGCGTATAGGGGC-GAAAGACTAATCGCCTTGACAGAGTTAGTCAG---CCCAGAAG
GCGTGACGTTTCTTGT--TCCTCATTTATGCTAACGTAATGGCCATCAGACCAATCCTCA
GTATAAGGCGGCTCTTTCTATTCGTGATCCAAAGCGTAGATTCGATACGATCTGGCGGCT
CTGCAAACCTAAGATGATTTGCGAGATTGATAGCACACCGGAAGATCTAGATTTCGAAGG
AAAGCCAACGGATGCCGGGAAAGTCCGAAGTCATGGTGGATGCGGAAATATTCAACCGGA
AGTTCGCCAGACCGCGCTTCAACTTTGGGGCACTTGGAAGGTACCAAAGGATGAGGATAA
TGAGG------CACAACAACCTGAGAAGAAGCAGATCTCACCTGAGATGGCATTGCAGGT
CTTCCGTAGCATCTCAAATGAGGAGATTCACGATCTTGGTCTGAACAATGATTATGCTCG
GCCAGAGTGGATGATTATCACCGTTCTTCCCGTACCTCCACCACCTGTCCGACCAAGTAT
TTCGATGGACGGCACTGGACAGGGCATGCGAGGAGAGGATGATTTGACTTATAAGCTTGG
CGATATCATCCGCGCGAATGGTAACGTCCGTC-AAGCACAGCAGGAAGG

Figure 4N

Mollisia_cinerea_DQ491498
GTGTCTA-------------------------------------------------------
--------------------------------------------------------------
------CATACTCTTGT-TGCTTTGGCAGGCCGTGG-TCT-CCAC--TGT----GGGCTC
TGCCTAC-----ATGTGCCTGCCAGAGGACC---AAAATCTGAATTTTAGTGATGTCTGA
GTACTATATAATAGTTAAAACTTTCAACAACGGATCTCTTGGTTCTGGCATCGATGAAGA
ACGCAGCGAAATGCGATAAGTAATGTGAATTGCAGAATTCAGTGAATCATCGAATCTTTG
AACGCACATTGCGCCCTGTGGTATTCCGCAGGGCATGCCTGTTCGAGCGTCATTATAACC
ACTCAAGCCTGGCTTGGTATTGGAGT-TTGCGGT--TCCGCAGCTCCTAAAATCAGTGGC
GGTGCCGGTGTGGCTCTACGCGTAGTAA-TTCTTCTCGCGATGGAGTTC-----------
----------------CC-------------------------CTGGTTGCTTGC--
--------------------------------------------------------------
-------------------------TAACGGCGAGTGAAGCGGTAACAGCTCAAATTTGA
AAGCTACC-----AACAGGTCGCATTGTAATTTGTAGAAGATGCTTTGGGTGTTGACCTA
GTCTAAGTTCCTTGGAACAGGACGTCATAGAGGGTGAGAATCCCGTATGTGATTAG-TGT
CAGCCCCCGTGTAAAGCTCTTTCGACGAGTCGAGTTGTTTGGGAATGCAGCTCAAAATGG
GTGGTAAATTTCATCTAAAGCTAAATATTGGCCAGAGACCGATAGCGCACAAGTAGAGTG
ATCGAAAGATGAAAAGCACTTTGGAAAGAGAGTTAAACAGTACGTGAAATTGTTGAAAGG
GAAGCGCTTGCAATCAGACTTGCAGGCAGTCGATCATCCGAGGTTC-TCCCCGGTGCACT
CGATTGTCT-TCAGGCCAGCATCGGTTTCGGTGGTGGGATAAAGGCTGTGGGAATGTGGC
TC--TTC------GGAGTGTTATAGCCCACGGTGCAATGCCGCCTACCGGGACCGAGGAC
CGCGCTTC-GGCTAGGATGCTGGCGTAATGGTTGTAAGCGACCCGTCTTGAAACACGGAC
CAAGGAGTCTAACATCTATGCGAGTGTTTGGGTGTCAAACCCATACGCGTAATGAAAGTG
AACGGAGGTGAGAACCCTTTAGGGTGCATCATCGACCGATCCTGATGTCTTCGGATGGAT
TTGAGTAAGAGCATAGCTGTTGGGACCCGAAAGATGGTGAACTATGCGTGAATAGGGTGA
AGCCAGAGGAAACTCTGGTGGAGGCTCGCAGCGGTTCTGACGTGCAAATCGATCGTC-AA
ATTTGCGTATAGGGGC-GAAAGACTAATCGGCTAGACAGGGTCAGTTCG---CCCGAAGA
GGGTGGCAGATCTACT--TGTTC-TTTGTGCTGACATGAGT-ATCTCAGAGTAATCCGGC
ATATGCAGCAGCTACAAGTATTCGCGACCCAAAGCGTAGGTTCGATACGATATGGCGACT
CTGCAAACCAAAAATGATCTGCGATAGCGATGTCCCAAATGAAGAT---GAATTCGGAGG
TGATCCTAAGGAAGCTGTCAAG---CGCTCACATGGAGGTTGTGGAAACACTCAGCCCGA
AGTGCGTCAACAATCTCTCCAACTTTGGGGTACATGGAAGATGCCAAAGGATGAGGAGAA
CGAGGGCGGTGCAACGCAG---GAGAAGAAACAAATTACTCCAGAGATGGCTCTCAATGT
CTTCAAAAGCATGTCCACCAAGGAGATCTACGATCTTGGCTTGAACAACGACTACGCTCG
TCCTGACTGGTTGATTATCACTGTTCTTCCAGTTCCACCTCCCCCAGTCCGACCAAGTAT
CTCCATGGATGGCACAAGTACCGGCATGCGTGGAGAGGATGATTTGACATACAAGCTTGG
TGATATCATTCGTGCAAATGGAAACGTTAAGC-AGGCACAACAGGAAGG

Figure 40

Monilinia_laxa_EF153017
GTGGAAGT--------------------------AAAAGTCGTAACAAGGTTTCCGTAG
GTGAACCTGCGGAAGGATCATTACAGAGTTCATGCCCGAAAGGGTAGACCTCCCACCCTT
GTGTATTATTACTTTGT-TGCTTTGGCGAGCTG----CC--------TTC----GGGCCT
TG-----------TATGCTCGCCAGAGAATAATCAAACTCTTTTATTAATGTCGTCTGA
GTACTATATAATAGTTAAAACTTTCAACAACGGATCTCTTGGTTCTGGCATCGATGAAGA
ACGCAGCGAAATGCGATAAGTAATGTGAATTGCAGAATTCAGTGAATCATCGAATCTTTG
AACGCACATTGCGCCCCTTGGTATTCCGGGGGGCATGCCTGTTCGAGCGTCATTTCAACC
-CTCAAGCACAGCTTGGTATTGAGTCTATGTCAGCAATGGCAGGCTCTAAAATCAGTGGC
GGCGCCGCTG-GGTCCTGAA----------------------------------------
------------------------------------------------------------
------------------------------------------------------------
------------GGGATTACCTCAGTAACGGCGAGTGAAGCGGTAAAAGCTCAAATTTGA
AATCTGGCTCTTTTAGAGTCCGAGTTGTAATTTGTAGAAGATGCTTCGGGTGTGGTTCCG
GTCTAAGTTCCTTGGAACAGGACGTCATAGAGGGTGAGAATCCCGTATGTGACTGGATAC
CTATGCTCATGTGAAGCTCTTTCGACGAGTCGAGTTGTTTGGGAATGCAGCTCAAAATGG
GTGGTATATTTCATCTAAAGCTAAATATTGGCCAGAGACCGATAGCGCACAAGTAGAGTG
ATCGAAAGATGAAAAGCACTTTGGAAAGAGAGTTAAACAGTACGTGAAATTGTTGAAAGG
GAAGCGCTTGCAATCAGACTTGCACTTGGT-GTTCATCGGGGTTTC-TACCCCGTGTACT
TCATCAAGT-TCAGGCCAGCATCAGTTTGGGTGGTTAGATAAAGGCTTAGAGAATGTGGC
CCTCTTC----GGGGGGTGTTATAGCTCTAGGTGCAATGTAGCCTACCTGG??TGAGG?C
CGCGCTTC-GGCTA?GATGCTGGCGTAATGGTTGTAAGCGACCCGTCTTGAAACACGGAC
CAAGGAGTGTACCTAATATGCGAGTGTTTGGGTGTT-AACCCATACGCGTAATGAAAGTG
AACGGAGGTGAGAGCCCTTAAGGGTGCATCATCGACCGATCCTGATGTCTTCGGATGGAT
TTGAGTAAGAGCATATTGGGTGCGACCCGAAAGATGGTGATCTATACGTGAATAGGGTGA
AGCCAGAGGAAACTCTGGTGGAGGCTCGCAGCGGTTCTGACGTGCAAATCGATCGTC-AA
ATTTGCGTATAGGGGC-GAAAGACTAATCGACTAGACAGGGTTAGTTTGCAACCAACTTG
AGGTGGTTTGTTT-CA--TGTGCCTTGATGCTAACACCAAA-GTATCAGAGTAATCCAGC
TTACAAGGCAGCCGTTTCCATCCGTGATCCTAAGCGCAGATTCGAAGCAATATGGAAACT
CTGCAAGTCCAAGATGATTTGTGATAGTGACGTCCAGGCGAACGAGGAGGAATTCAATGG
AGATCCAAAGGAAGCTGCAAAG---CGATCGCATGGAGGATGCGGCAATACTCAACCTGA
AGTCCGTCAAACTGCTCTGGCCCTCTGGGGTACGTGGAAGCCGCCCAAGGATGAAGACGG
AGAGGCTGT------GCAACCTGACAAGAGACAAATCACTCCGGAGATGGCTCTTAACGT
CTTTCGCAGCATGACCACTGCAGAAATCCAGGATGTTGGATTGAACGCAGATTATGCTCG
CCCAGAATGGATGATTATTACCGTTCTACCAGTACCACCGCCTCCCGTTCGACCAAGTAT
TTCCATGGATGGTACTGGTCAGGGTATGCGAGGAGAGGATGATTTGACATACAAGTTGGG
TGATATCATTCGTGCCAATGGTAACGTTCGTC-AAGCACAACAAGAAGG

Figure 4P

```
Phialocephala_fortinii_AB671499
GTGTTTA-----------------------------------------------------
------------------------------------------------------------
------CATACTATTGT-TGCTTTGGCGGGCCGTGG-CCT-CCAC--TGC----GGGCTC
TGCTCGT-----GTGTGCCCGCCAGAGAACC---AAACTCTGAATGTTAGTGATGTCTGA
GTACTATCTAATAGTTAAAACTTTCAACAACGGATCTCTTGGTTCTGGCATCGATGAAGA
ACGCAGCGAAATGCGATAAGTAATGTGAATTGCAGAATTCAGTGAATCATCGAATCTTTG
AACGCACATTGCGCCCTGTGGTATTCCGCAGGGCATGCCTGTTCGAGCGTCATT-TAACC
ACTCACGCCTAGCGTGGTATTGGGGC-ACGCGGTC-TCCGCGGCCCTCAAAATGAGTGGC
GGCGCCGGTG-GGCTCTAAGCGTAGTAC-ATACTCCGCTATAGAGTTC-----------
----------------CC-------------------------CCGGTGGCTCGC--
------------------------------------------------------------
-----------------------GTAACGGCGAGTGAAGCGGTAACAGCTCAAATTTGA
AAGCTGCC-----AACAGGCCGCGTTGTAATTTGTAGAAGCTGCTTTGGGTGTCGGCCCG
GTCTAAGTTCCTTGGAACAGGACGTCATAGAGGGTGAGAATCCCGTATGTGATCGG-TGC
CGTTGCCCGTGTAAAGCGCTTTCGACGAGTCGAGTTGTTTGGGAATGCAGCTCAAAATGG
GTGGTAAATTTCATCTAAAGCTAAATATTGGCCAGAGACCGATAGCGCACAAGTAGAGTG
ATCGAAAGATGAAAAGCACTTTGGAAAGAGAGTTAAACAGTACGTGAAATTGTTGAAAGG
GAAGCGCTTGCAACCAGACTTGCGGGCGGTCGATCATCCGAGGTTC-TCCCGGTGCACT
CGATCGTTC-TCAGGCCAGCATCGGTTTCCGGGGTGGGATAAAGGCGGTGGGAATGTGGC
TC--TTC------GGAGTGTTATAGCCCACCGTGCAATGCCGCCACTGGGGACCGAGGAC
CGCGCTTC-GGCTAGGATGCTGGCGTAATGGTTGTAAGCGACCCGTCTTGAAACACGGAC
CAAGGAGTCTAACATCTATGCGAGTGTTTGGGTGTCAAACCCATACGCGTAATGAAAGTG
AACGGAGGTAAGAGCCCTTTAGGGTGCATTATCGACCGATCCTGATGTCTTCGGATGGAT
TTGAGTAAGAGCATAGCTGTTGGGACCCGAAAGATGGTGAACTATGCGTGAATAGGGTGA
AGCCAGAGGAAACTCTGGTGGAGGCTCGCAGCGGTTCTGACGTGCAAATCGATCGTC-AA
ATTTGCGTATAGGGGC-GAAAGACTAATCGGCTAGACAGAGTCAGTTCG---CCCGATGA
GGGTGGCAGATCTACT--TGTTC--TTGTGCTGACATGAGT-ATCTCAGAGTAATCCGGC
CTTCAAAGCAGCTGTTTCCATTCGAGACCCGAAGCGTAGGTTCGATACGATTTGGCGACT
TTGCAAGCCCAAGATGATCTGCGATAGCGACGTTTCTGCGGACGATCAGGAATTCGGTGG
CGATCCAAGGGAAGCTGTGAAG---CGCTCTCATGGAGGTTGTGGAAATACTCAGCCCGA
GGTGCGCCAGCAGGCTCTGCAGCTTTGGGGTACATGGAAGATGCCTAAGGACGAGGAGAA
CGAGGG------AAACCAATCCGAGAAGAGACAAATCACTCCAGAGATGGCTCTGAACGT
CTTCCGAAGCATGTCTACTGCTGAGATTCGCGACCTTGGGTTGAGCAACGATTATGCCCG
TCCCGACTGGCTGATCATCACAGTCCTTCCAGTTCCTCCTCCGCCGGTTCGACCAAGTAT
TTCTATGGATGGCACAAGCACTGGAATGCGTGGAGAAGATGATTTGACATACAAGCTCGG
TGATATCATTCGTGCGAATGGAAATGTCAAGC-AGGCACAACAGGAAGG
```

Figure 4Q

Vibrissea_truncorum_EU434855
GTGTTTA-----------------------------------------------------
------------------------------------------------------------
------CATACTCTTGT-TGCTTTGGCAGGCCGTGG-CCT-CCAC--TGC----GGGCTC
TGCTCGT-----ACGTGCCCGCCAGAGGACC---AAACTCTGAATGTTAGTGATGTCTGA
GTACTATATAATAGTTAAAACTTTCAACAACGGATCTCTTGGTTCTGGCATCGATGAAGA
ACGCAGCGAAATGCGATAAGTAATGTGAATTGCAGAATTCAGTGAATCATCGAATCTTTG
AACGCACATTGCGCCCGGTGGTATTCCGCCGGGCATGCCTGTTCGAGCGTCATTATAACC
AATCACGCCTGGCGTGGTGTTGGGGC-ACACGGC--TCCGTGGCCCTCAAAATCAGTGGC
GATGCCGGTT-GGCTCTAAGCGTAGTAA-CTTCTCTCGCTATAGATGTC-----------
----------------------------------------TGCTGGTTGCTCGC--
------------------------------------------------------------
------------------CCTCAGTAACGGCGAGTGAAGCGGTAACAGCTCAAATTTGA
AAGCTGCC-----AACAGGCCGCATTGTAATTTGTAGAGGATGCTTTGGGGGTTGGCCCG
GTCTAAGTTCCTTGGAACAGGACGTCATAGAGGGTGAGAATCCCGTATGTGCCCGG-TGC
CCGCCCCGTGTAAAGCTCCTTCAACGAGTCGAGTTGTTTGGGAATGCAGCTCAAAATGG
GTGGTATATTTCATCTAAAGCTAAATATTGGCCAGAGACCGATAGCGCACAAGTAGAGTG
ATCGAAAGATGAAAAGCACTTTGGAAAGAGAGTTAAACAGTACGTGAAATTGTTGAAAGG
GAAGCGCTTGCAATCAGACTTGCAGGCGGTCGATCATCCGGGGTTC-TCCTCGGTGCACT
CGGCCGTCT-TCAGGCCAGCATCAGTTTCGGTGGTGGGATAAAGGCCTTGGGAATGTAGC
TT--CTT----CGGGAGTGTTATAGCCCTCGGTGCAATGCCGCCTACCGGGACTGAGGAC
CGCGCTTC-GGCTAGGATGCTGGCGTAATGGTTGTAAGCGACCCGTCTTGAAACACGGAC
CAAGGAGTCTAACATCTATGCGAGTGTTTGGGTGTCAAACCCATACGCGGAATGAAAGTG
AACGGAGGTAAGAACCCTTTAGGGCGCATTATCGACCGATCCTGATGTCTTCGGATGGAT
TTGAGTAAGAGCATAGCTGTTGGGACCCGAAAGATGGTGAACTATGCGTGAATAGGGTGA
AGCCAGAGGAAACTCTGGTGGAGGCTCGCAGCGGTTCTGACGTGCAAATCGATCGTC-AA
ATTTGCGTATAGGGGC-GAAAGACTAATCGATTAGACAGGGTTTGTTTG---CCTGTTGA
AATGGG--AATCTAAC--AGTTCATTTGTGCTGACACGGATGAAAATAGAATAATCCTGC
ATTCAAGGCCGCTGTTAATATTCGAGACCCAAAGCGAAAATTCGATACGATATGGCGACT
CTGCAAGCCGAAGCTTGTTTGCGACAGTGACATCAATCCCGACGATCCAGAGTTCAACAG
CGATCCCAAGGAAGCAGCAAAG---CGTTCTCATGGTGGATGTGGCAATACTCAACCCGA
GGTGCGCCAACAGGCTTTACAACTTTGGGGTACCTGGAAGATGCCGAAGGATGAGGAGAA
CGATGGTGG---------ATCTGAGAAGAGACAAATCACTCCAGAGATGGCTCTGAACGT
TCTTCGAAGCATGTCTACTTCTGACATTCGGGATCTGGGACTCAGCGTCGATTATGCTCG
TCCTGAGTGGTTGATCATCACAGTTCTGCCAGTTCCTCCACCACCCGTCCGACCCAGTAT
TTCCATGGATGGCACAAGCACTGGTATGCGCGGAGAGGATGATTTGACCTATAAGCTTGG
TGATATTATCCGTGCAAATGGCAATGTGAAGC-AGGCACAACAGGAAGG

Figure 4R

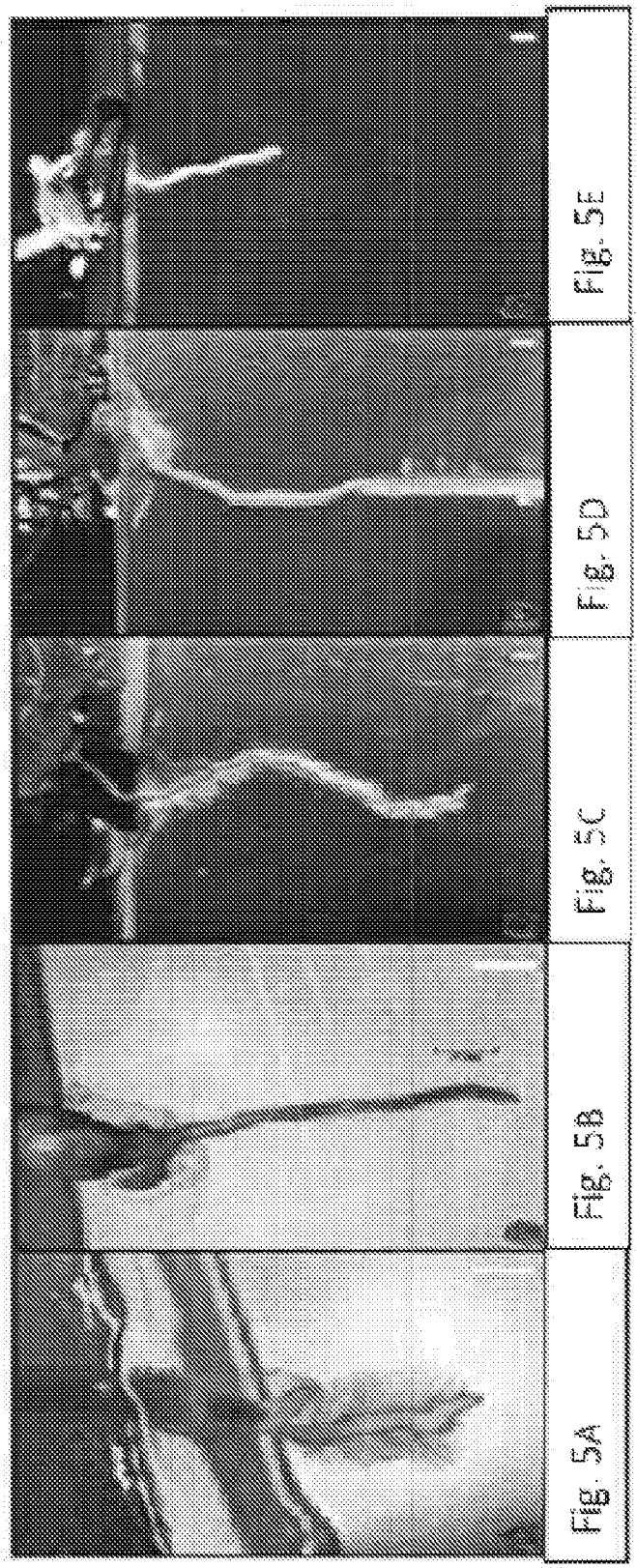

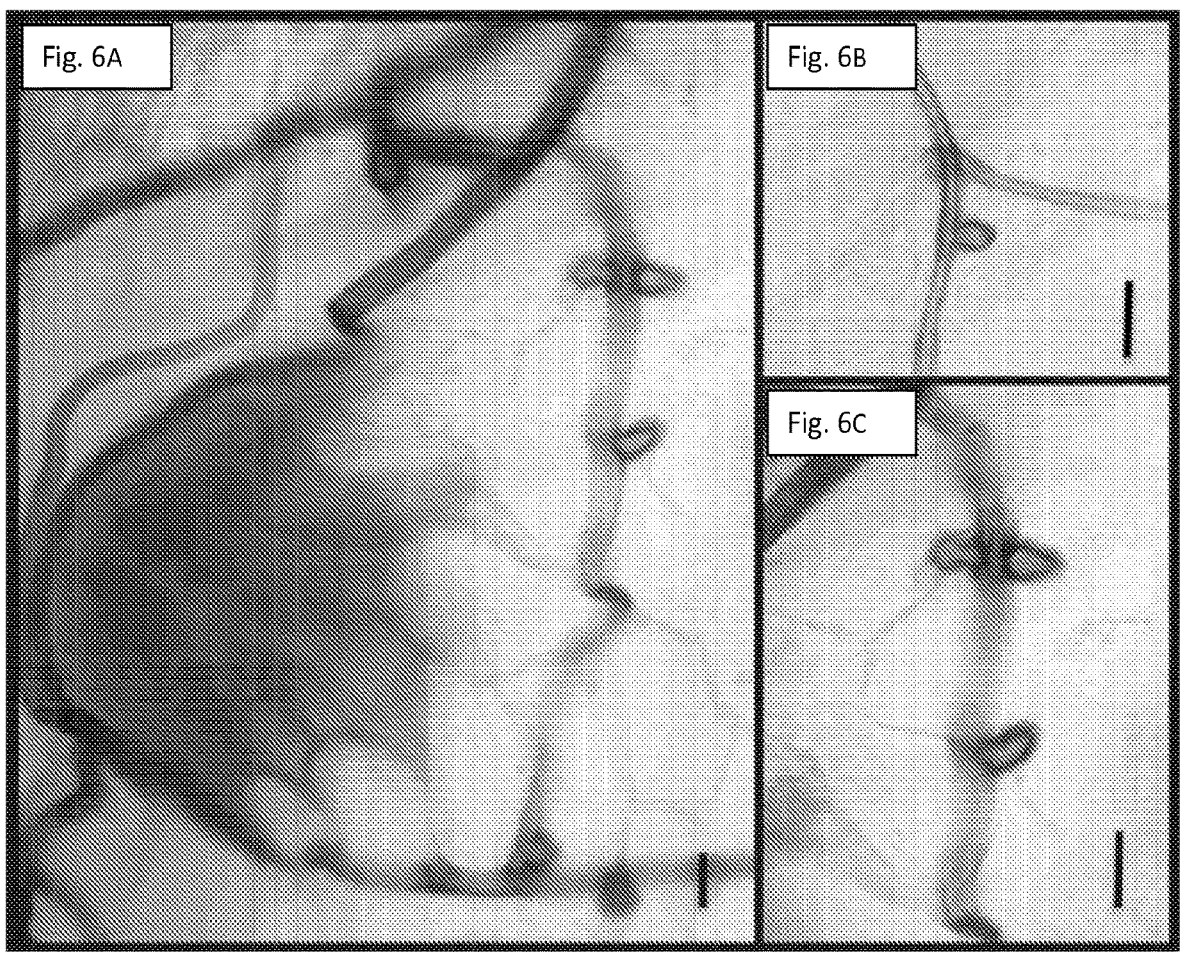

COMPOSITIONS AND METHODS THEREOF INCREASING PLANT GROWTH AND RESISTANCE TO ENVIRONMENTAL STRESS

CROSS-REFERENCE TO RELATED APPLICATIONS

This application is a § 371 of International Application No. PCT/US2015/048889, filed Sep. 8, 2015, which claims the benefit to U.S. Provisional Application No. 62/047,226, filed Sep. 8, 2014. The entire disclosure of each of the aforesaid applications is incorporated by reference in the present application.

FIELD OF THE INVENTION

This invention relates to the fields of agriculture and propagation of plants under abiotic stress conditions. More specifically, the invention provides methods and microbial based compositions which facilitate improved plant growth and stress tolerance.

BACKGROUND OF THE INVENTION

Several publications and patent documents are referenced throughout this application in order to more fully describe the state of the art to which this invention pertains. The disclosure of each of these publications and patent documents is incorporated by reference herein.

Pine barrens (pinelands) comprise a unique type of ecosystem that is oligotrophic, and both drought- and fire-prone. Pine barrens occur throughout northeastern USA from New Jersey to Maine (Forman et al. 1998). Pines and oaks are the most common trees in pine barrens, while the understory is composed of grasses (Poaceae), sedges (Cyperaceae), blueberries and other members of heath family (Ericaceae). The largest and most uniform area of pine barrens in the United States is the 1.4 million acre pine barrens of New Jersey, where the soil is highly acidic, sandy and nutrient poor.

Dark septate endophytes (DSE) refer to a group of heterogeneous plant root-colonizing ascomycetes that produce melanized, septate hyphae. They have been isolated from over 110 plant families that grow in various environments (Knapp et al. 2012). The best studied DSE are the *Phialocephala fortinii-Acephala applanata* complex (PAC), a group of asexual fungi in *Helotiales* of *Leotiomycetes* (Wang et al. 2006). Fungi in PAC are characterized by darkly pigmented hyphae, and typically produce branched conidiophores, hyaline phialides with collarettes, and intracellular microsclerotia (Grünig et al. 2008a, 2008b; Yu et al. 2001). PAC are the common root associates of many tree species, specifically conifers in forests of the northern hemisphere (Grünig et al. 2008a, 2008b; Menkis 2004). Despite the global pervasiveness of DSE, their ecological roles, phylogenetic relationships and taxonomy remain poorly understood (Knapp et al. 2012; Mandyam and Jumpponen 2005). DSE fungal-plant interaction studies have yielded variable results, likely due to the use of differing experimental design strategies (Grünig et al. 2008b).

It is estimated that 30% of the world's total land area consists of acid soils, and 50% of the world's potential arable lands are acidic (Tuininga et al. 2004). In view of these adverse environmental conditions, improved methods to enhance growth of both edible and non-edible plants are needed.

SUMMARY OF INVENTION

In accordance with the present invention, a method for enhancing overall plant growth and resistance to adverse abiotic conditions comprising contacting a plant or seed therefrom with a composition comprising a biofertilizer comprising at least one endophytic fungi and optionally bacteria. In one aspect, the fungi is *Acidomelania panicicola* and the optional bacteria is from the *Burkholderia* genus. The method can include inoculating the seeds with the fungi and, or bacteria in agar or growth medium and placing seeds/agar composition in the soil. In another approach, after mixing the cultures, the seeds and cultures are subjected to drying to form a coating thereon. Vermiculite and rock phosphate may also be included in the composition to enhance plant growth and resistance to abiotic stress. The method can be applied to both monocots and dicots and can be used on plants which include without limitation, lettuce, corn, rice, soybeans, potatoes, barley, wheat, and carrots. In a particularly preferred embodiment, the plant is a turfgrass plant selected from a Ryegrass, Kentucky Bluegrass, Tall Fescue, Bermuda, St. Augustine or Zoysia plant or any other turfgrass plant.

In another aspect of the invention, a biofertilizer composition is provided. An exemplary biofertilizer includes an effective amount of *A. panicicola* and at least one agent or microorganism for promoting plant growth and resistance to abiotic stresses for use in the method described above. In a preferred embodiment, the composition contains *A. panicicola* and at least one *Burkholderia* species in equal concentrations. The composition may also contain a sun protecting product and a polysaccharide solution. The fungal strains may also be encapsulated in allignate beads.

In yet another aspect of the invention the fungus for use in the method is selected from the *Barrenia* genus. In a preferred embodiment, the fungi is *Barrenia panicia*. This composition may also comprise a bacteria selected from the *Burkholderia* genus.

The biofertilizer composition comprising at least *A. panicicola* and, or *Barrenia* and, optionally, other agents or microbial or fungal species are effective to enhance plant resistance to environmental stresses. Such agents may include gel formulations, agar, vermiculite, sun protectorants, rock phosphate, alginate, which when combined form an efficacious biofertilizer.

BRIEF DESCRIPTION OF THE DRAWINGS

FIG. 4. DNA sequence for *A. applanata* AY078151; SEQ ID NO: 1 (FIG. 4A), *A. panicicola* KF874620; SEQ ID NO: 2 (FIG. 4B), *A. panicicola* KF874619; SEQ ID NO: 3 (FIG. 4C), *A. panicicola* AL5m2-2; SEQ ID NO: 4 (FIG. 4D), *A. panicicola* CM11M2; SEQ ID NO: 5 (FIG. 4E), *A. panicicola* WSF1-R37; SEQ ID NO: 6 (FIG. 4F), *A. taeda* CM14-P64; SEQ ID NO: 7 (FIG. 4G), *A. taeda* WSF14-P22; SEQ ID NO: 8 (FIG. 4H), *A. taeda* WSF14-P13; SEQ ID NO: 9 (FIG. 4I), *C. clavus* DQ491502; SEQ ID NO: 10 (FIG. 4J), *D. acerina* AF141164; SEQ ID NO: 11 (FIG. 4K),

*H. aureliella* JN943611; SEQ ID NO: 12 (FIG. 4L), *L. virgineum* DQ491485; SEQ ID NO: 13 (FIG. 4M), *L. macrospores* DQ471005; SEQ ID NO: 14 (FIG. 4N), *M. cinerea* DQ491498; SEQ ID NO: 15 (FIG. 4O), *M. laxa* EF153017; SEQ ID NO: 16 (FIG. 4P), *P. fortinii* AB671499; SEQ ID NO: 17 (FIG. 4Q), and *V. truncorum* EU434855; SEQ ID NO: 18 (FIG. 4R).

FIGS. 5A-5E. Switchgrass seedling two days after inoculation with *Acidomelania panicicola* holotype isolate 61R8 (FIG. 5A); Control (FIG. 5B); three days after inoculation with *Barrenia panicia* holotype isolate WSF1R37 (FIG. 5C); Control (FIG. 5D), *Barrenia taeda* holotype isolate WSF14P22 (FIG. 5E). Bar=1 mm FIGS. 6A-6C. Representative image of morphological characters of *Barrenia panicia* holotype isolate WSF1R37 (FIG. 6A); Representative image of morphological characters of *Barrenia panicia* holotype isolate WSF1R37 (FIG. 6B); Representative image of morphological characters of *Barrenia panicia* holotype isolate WSF1R37 (FIG. 6C). A-Bar=10 μm FIG. 7. Micrographs of control and *Acidomelania panicicola* inoculated switchgrass seedling roots 2 days post inoculation.

Figure 8:
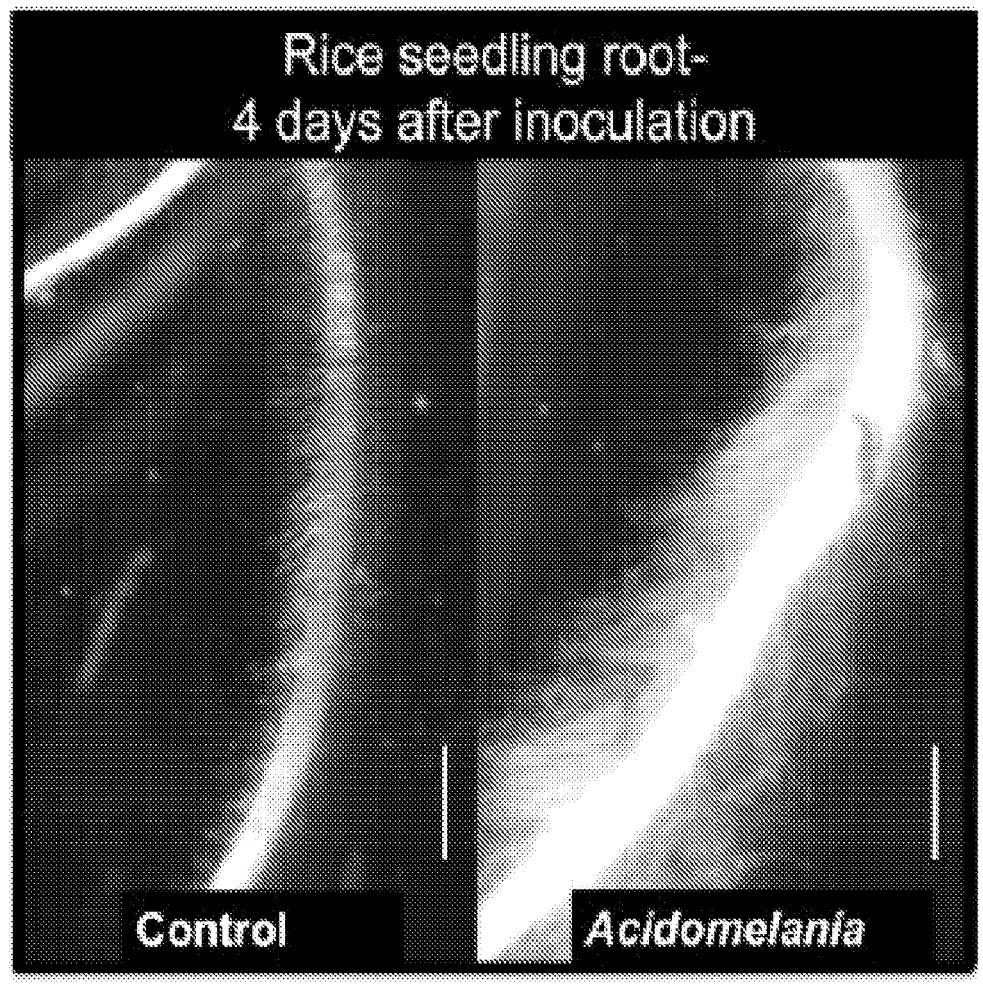

FIG. 8. Micrographs of control and *Acidomelania panicicola* inoculated rice seedling roots 4 days post inoculation.

Figure 9:
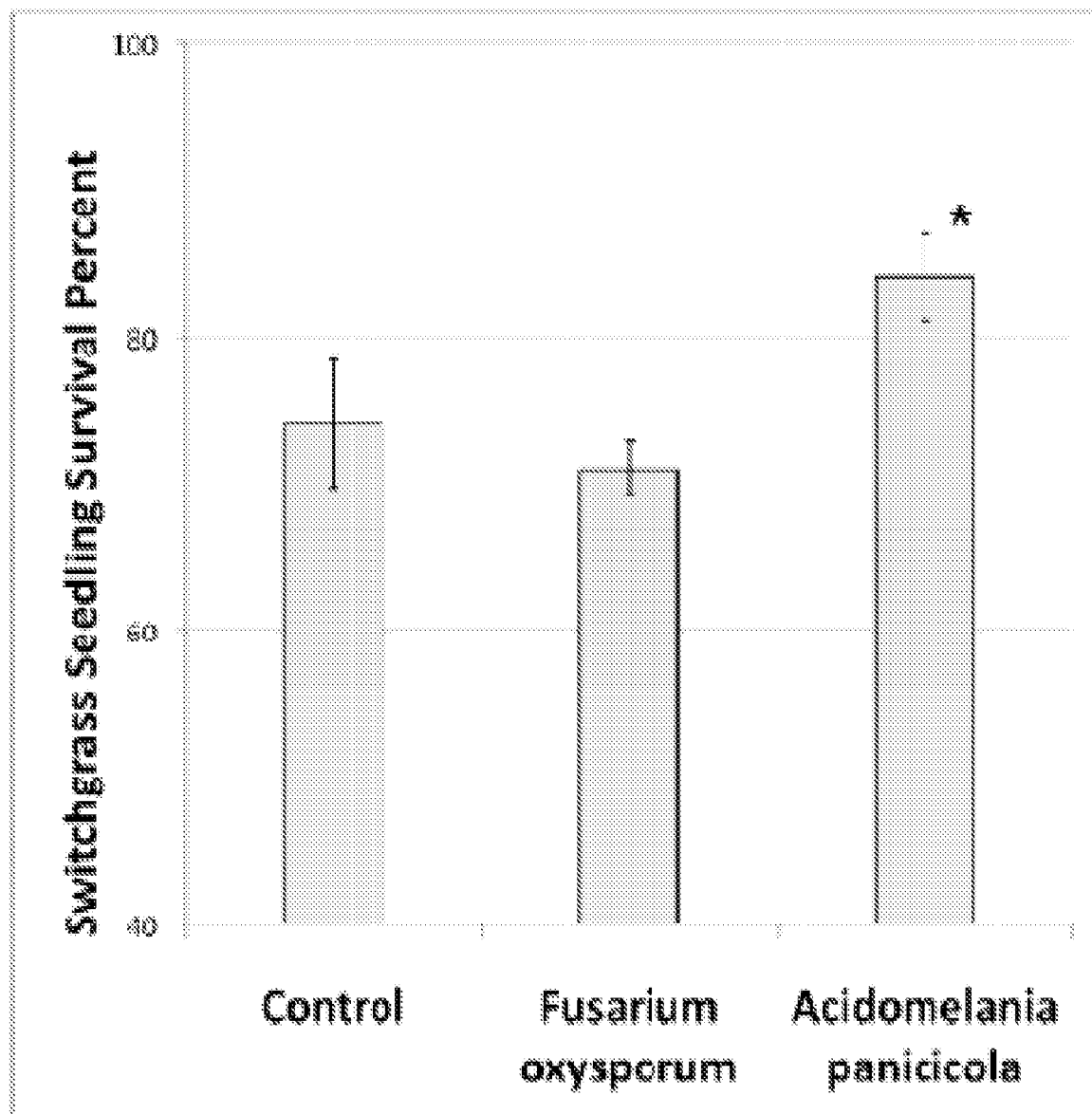

FIG. 9. Micrographs showing control, *Fusarium oxysporum* inoculated and *Acidomelania panicicola* inoculated switchgrass seedling survival percentage.

Figure 10:
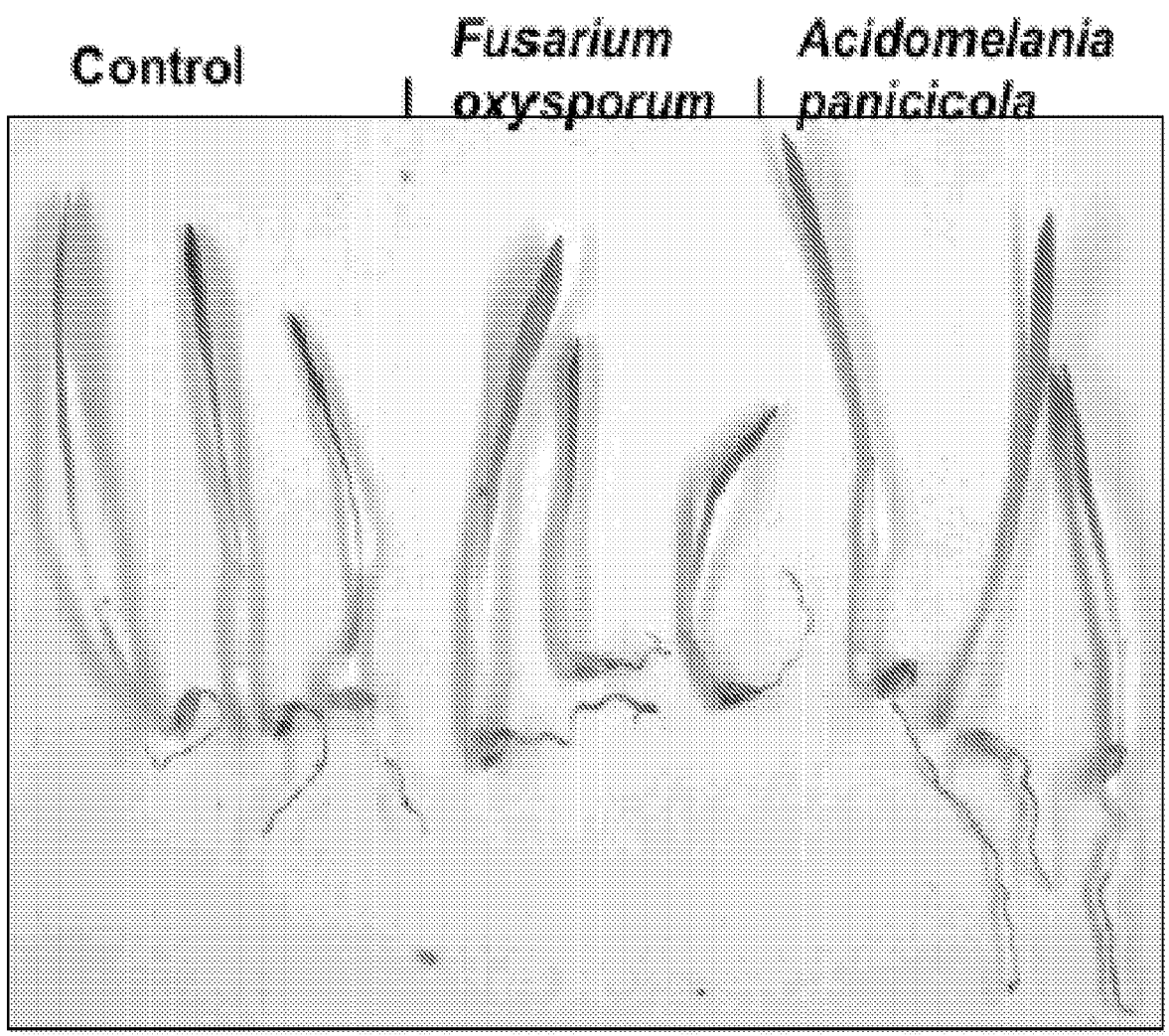

FIG. 10. Micrographs showing control, *Fusarium oxysporum* inoculated and *Acidomelania panicicola* inoculated switchgrass roots.

Figure 11:
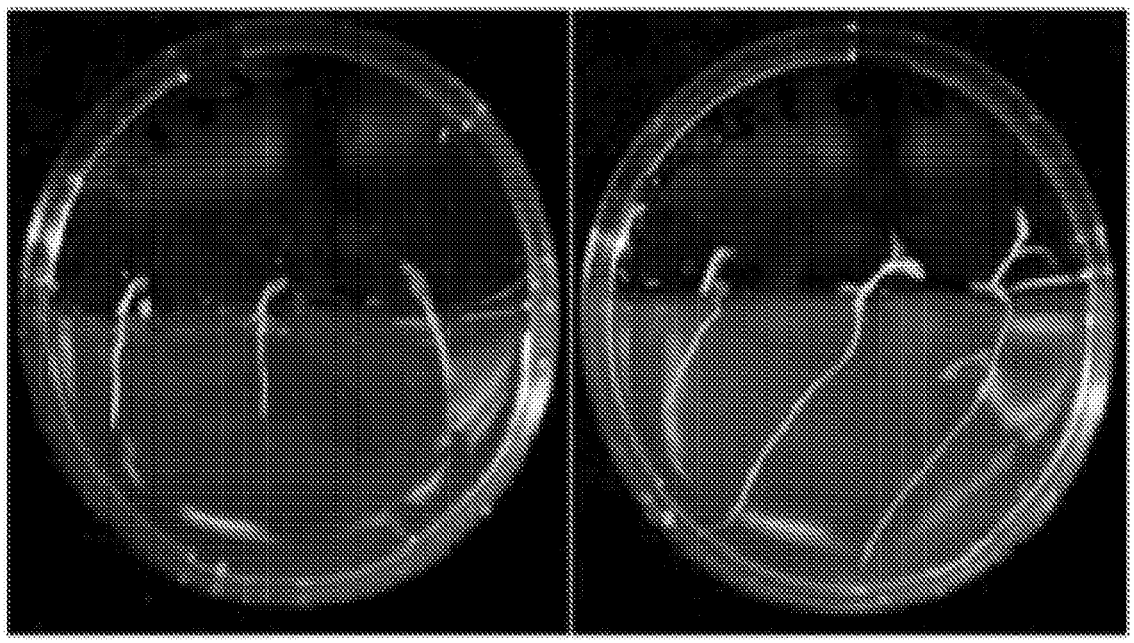

FIG. 11. Micrographs showing control and *Acidomelania panicicola* inoculated lettuce roots 4 days post inoculation.

DETAILED DESCRIPTION OF THE INVENTION

Drought and low nutrient stress typified early terrestrial environments when plant colonization of land occurred and was facilitated by root-symbiotic fungi (Stoyke et al. 1991). Beneficial endophytes encompass bacteria and fungi that have the ability to alleviate abiotic stresses in combination with plant growth promotion. Endophytes have been reported to enhance early root differentiation, improve drought and salinity tolerance and increased survival rate. These endophytes play critical roles in litter decomposition, nutrient absorption and cycling (Forman et al. 1998; Blackwell et al. 2011).

A group of new fungal species were discovered from switchgrass and other grass roots in the New Jersey Pine Barrens, which is a dry, highly acidic environment, low in nutrients (P, K, organic matter etc.), with high aluminum toxicity (von Uexkull et al. 1995). Herein we describe two new genuses, *Acidomelania* and *Barrenia*, discovered in pine barren switchgrass roots.

*Barrenia* was classified using multi-gene phylogenetic analyses, along with phenotypic and ecological characteristics. While the new species was isolated from roots of switchgrass and pitch pine in the acidic and oligotrophic New Jersey Pine Barrens, *Barrenia* likely has a wide distribution as its internal transcribed spacer (ITS) sequence has high similarity with a number of GenBank sequences obtained in various ecological studies. The majority of these similar ITS sequences were obtained from roots in plants growing in acidic, nutrient-poor environments, as well as from managed sugarcane plantations. Phylogenetic analyses of ITS, LSU and RPB1 sequence data strongly support that *Barrenia* is a monophyletic Clade in *Helotiales*, distinct from any known taxa. *Barrenia* is phylogenetically close to *Acidomelania, Loramyces, Mollisia*, and *Phialocephala fortinii-Acephala applanata* species complex (PAC), the dark septate endophytes. *Barrenia* can be distinguished from *Loramyces* and *Mollisia* by its association with living plant roots. While taxa in PAC also are root endophytes, they have complex phialid arrangements that appear to be lacking in *Barrenia*.

The present inventors have performed functional studies which demonstrate that application of biofertilizers comprising *Acidomelania panicicola* and *Barrenia panicia* significantly enhanced dense root hair growth in switchgrass. *Acidomelania panicicola* plant-fungal interactions with rice and lettuce seedlings under acidic and poor nutrient conditions also resulted in a significant promotion of root and shoot length.

In one aspect of the invention, a biofertilizer composition is prepared by inoculating seeds with fungi (e.g. *Acidomelania panicicola* or any fungus selected from the genus *Barrenia*) on agar or growth medium and placing seeds and agar in the soil. In another aspect of the invention, a biofertilizer composition is prepared by mixing fungi and bacterial cultures with seeds prior to placing seeds in the soil, the cultures optionally forming a coating around the seeds. In a third aspect of the invention, seeds are mixed with fungi and bacterial cultures and dried. In a fourth aspect of the invention, seeds are grown in fungal inoculated soil formulated with vermiculite and rock phosphate.

DEFINITIONS

An endophyte is an endosymbiont, often a bacterium or fungus, that lives within a plant without causing apparent disease. Endophytes may enhance a plant's growth and improve the plant's ability to tolerate abiotic stresses such as drought or harsh soil conditions. In one embodiment an endophyte useful herein comprises the fungus, *Acidomelania panicicola*. In another embodiment, an endophyte comprises *Barrenia panicia*. Endophytes useful herein include the fungus *Acidomelania panicicola* in combination with certain bacteria selected from the bacterial species, *Burkholderia*. In yet another approach, the fungi *Acidomelania panicicola* and the fungi *Barrenia panicia* are used in combination to enhance plant growth under abiotic stress conditions.

The term "abiotic" includes non-living chemical and physical parts of the environment that affect ecosystems. An ecosystem's abiotic factors may be classified via "SWATS" (Soil, Water, Air, Temperature, Sunlight).

The term "biofertilizer" comprises at least one substance containing living microorganisms which, when applied to seed, plant surfaces, and/or soil, colonizes the rhizosphere or the interior of the plant and promotes growth by increasing the supply or availability of primary nutrients to the host plant. Biofertilizers can also comprise other agents which enhance the growth of the microorganisms present. Such agents include, without limitation, agar, gel, and minerals.

The term "crop" herein refers to any plant grown to be harvested or used for any economic purpose, including for example human foods, livestock fodder, fuel or pharmaceutical production.

The following materials and methods provided to facilitate the practice of the present invention.

Fungal Isolation

Poaceae grass roots were collected from three locations (N 40 12.00, W 74 30.00; N40 04.084, W74 26.696; and N 39 46.136, W 74 40.885) in New Jersey Pine Barrens in 2012 and 2013. Native pitch pine (*Pinus rigida*) roots were collected from two locations (N40 04.084, W74 26.696; and N 39 46.136, W 74 40.885) in New Jersey Pine Barrens in 2014 (Tables 1 and 2). Soil pH of the sampling locations ranged from 4.7 to 5.2. Root samples were rinsed thoroughly to remove soil from the surface, cut into 10-20 mm pieces then surface disinfected with sequential washes of 95% ethanol for 30 s, 0.5% NaOCl for 2 min and 70% ethanol for 2 min. After several rinses with sterile water and drying, the root samples were cut into 5 mm pieces and plated on acidified malt extract agar (AMEA, 1.5 ml 85% lactic acid per liter of 2% malt extract agar). Plates were incubated at room temperature with 12 h light and 12 h dark cycles. Fungal cultures were transferred to fresh AMEA and purified by sub-culturing from emergent hyphal tips.

TABLE 1

| Species | MycoBank # | Etymology | Morphological description | Type species | Habitat | Known distribution |
|---|---|---|---|---|---|---|
| Barrenia E. Walsh & N. Zhang, gen. nov. | MB811715 | "Barren" refers to the pine barrens ecosystem where the fungi were discovered | Colonies on MEA darkly pigmented, surface fluffy, aerial hyphae thick and light brown. Colonies on WA light brown; sparse aerial hyphae. Sporulation not observed | *Barrenia panicia* | Endophytic in roots of Poaceae grasses | New Jersey Pine Barrens, United States |

TABLE 2

| Species | MycoBank # | Etymology | Morphological Description | Holotype | Other materials examined |
|---|---|---|---|---|---|
| *Barrenia panicia* E. Walsh & N. Zhang, sp. nov. | MB811716 | "panici" refers to the host | Colonies on MEA 55 mm diam after 20 d in the dark at 25 C., Cinnamon Brown, surface fluffy, aerial hyphae thick and light brown, reverse pigmented, Warm Sepia. Colonies on WA reaching 51 mm diam after 20 d in the dark at 25 C., Ochraceous Tawny, aerial hyphae sparse, reverse pigmented, Cinnamon Brown. Warm Sepia, paddle-shaped hyphopodium-like structures formed in inoculated switchgrass root tissue | United States: New Jersey: Wharton State Forest, N 39 45.346, W 074 41.684, 3 m alt., from roots of *Panicum virgatum*, 5 Jun. 2013, E. Walsh & N. Zhang, WSF1R37 (RUTPP-WSF1R37) | United States: New Jersey: Assunpink Lake, N 40 12.00, W 74 30.00, 3 m alt., from roots of *Digitaria* sp., 30 Aug. 2012, E. Walsh & N. Zhang AL5m2; Colliers Mills, N40 04.084 W74 26.696, 5 m alt., from roots of *Coix lacryma - jobi*, 30 Aug. 2012, E. Walsh & N. Zhang CM11m2 |
| *Barrenia taeda* E. Walsh & N. Zhang, sp. nov. | MB811717 | "taeda" means pine wood and refers to the host | Colonies on MEA 28 mm diam after 20 d in the dark at 25 C., Cinnamon Brown, surface fluffy, aerial hyphae thick and light brown, reverse pigmented, Mummy Brown. Colonies on WA reaching 31 mm diam after 20 d in the dark at 25 C., Buckthorn Brown, sparse aerial hyphae, reverse pigmented, Buckthorn Brown. Sporulation not observed | United States: New Jersey: Wharton State Forest N 39 45.346, W 074 41.684, 3 m alt., from roots of *Pinus rigida*, 26 Jun. 2014, E. Walsh & N. Zhang WSF14P22 (RUTPP-WSF14P22) | United States: New Jersey: Wharton State Forest, N 39 45.346, W 074 41.684, 3 m alt., from roots of *Pinus rigida*, 26 Jun. 2014, E. Walsh & N. Zhang WFS14P13; Colliers Mills, N40 04.084 W74 26.696, 5 m alt., from roots of *Pinus rigida*, 4 Jun. 2014, E. Walsh & N. Zhang CM14P64 |

Morphological Study and Growth Rate

Purified fungal isolates were grown on cellophane overlaid with 2% MEA (BD Difco, Maryland) and 2% water agar (WA). Cultures were incubated at 20° C. in the dark with three replicates. Colony diameter was measured after 20 days. The color names of colonies followed Ridgway (1912).

DNA Extraction, Amplification and Sequencing

Genomic DNA was extracted from fungal mycelium using the UltraClean Soil DNA isolation kit (MoBio, California) following the manufacturer's instructions. PCR was performed with Taq 2X Master Mix (New England BioLabs, Maine), following the manufacturer's instructions. PCR cycling conditions for the internal transcribed spacer (ITS) and the large subunit of ribosomal RNA genes (LSU) consisted of an initial denaturation step at 95° C. for 2 min, 35 cycles of 95° C. for 45 s, 54° C. for 45 s, 72° C. for 1.5 min, and a final extension at 72° C. for 5 min. For the largest subunit of RNA polymerase II (RPB1), the cycling conditions included an initial denaturation step at 95° C. for 2 min, 35° cycles of 95° C. for 60 s, 55° C. for 1.5 min, 72° C. for 2 min, and a final extension at 72° C. for 10 min. Primers used in this study are as follows: ITS1 and ITS4 for the ITS region (White et al. 1990), ITS1 and LR5 for the LSU locus (Rehner and Samuels 1995), and RPB1 Af (Hall and Stiller 1997) and RPB1 CrRev (Matheny et al. 2002) for the RPB1 gene. PCR products were purified with ExoSAP-IT (Affymetrix, California) and sequenced with the PCR primers by Genscript Inc. (Piscataway, N.J.).

Sequence Alignment and Phylogenetic Analyses

Six representative isolates of the new taxon (CM11m2, CM14P64, AL5m2, WSF1R37, WSF14P13, and WSF14P22) as well as other reference *Leotiomycetes* species (Table 3) were included in the phylogenetic analyses. The ITS dataset included sequences of the six new isolates from this study and 15 reference sequences of *Helotiales*. The LSU dataset included the six new sequences and 28 reference sequences of *Helotiales* and *Rhytismatales*. The three-gene (ITS, LSU and RPB1) alignment included the six new sequences and 12 reference sequences of. Sequences were aligned with MUSCLE (Edgar 2004). Maximum likelihood (ML) tree was generated with MEGA 6 (Tamura et al. 2013). Models with the lowest BIC scores (Bayesian Information Criterion) were considered to describe the substitution pattern the best. The best models for LSU, ITS and three-gene datasets were Tamura-3 parameter, Kimura 2-parameter, Kimura 2-parameter, respectively. Initial tree(s) for the heuristic search were obtained automatically by applying Neighbor-Join and BioNJ algorithms to a matrix of pairwise distances estimated using the Maximum Composite Likelihood approach, and then selecting the topology with superior log likelihood value. A discrete Gamma distribution was used to model evolutionary rate differences among sites. Bootstrap was computed for 500 replications. All positions containing gaps and missing data were excluded from the analyses.

TABLE 3

Species name, isolate number, host, location and GenBank accession numbers of the fungi used in this study.

| Species | Isolate number [a] | Host | Location | ITS | LSU | RPB1 |
|---|---|---|---|---|---|---|
| Acephala applanata | CBS109321 | Picea abies, root | Büdmerenwald, Switzerland | AY078145 | KF951051 | AFTOL 3613 |
| Acephala macrosclerotium | CBS123555 | Pinus sylvestris, root | Hubertusstock, Germany | HM189719 | | |
| Acidomelania panicola | CBS137156 | Panicum virgatum, root | New Jersey Pine Barrens, USA | KF874619 | KF874622 | — |
| Acidomelania panicola | CM16s1 | Schizachyrium scoparium, root | New Jersey Pine Barrens, USA | KF874620 | KF874621 | — |
| Barrenia panicia | AL5m2 | Digitaria sp., root | New Jersey Pine Barrens, USA | — | — | — |
| Barrenia panicia | CM11M2 | Coix lacrymajobi, root | New Jersey Pine Barrens, USA | — | — | — |
| Barrenia panicia | WSF1R37 | Panicum virgatum, root | New Jersey Pine Barrens, USA | — | — | — |
| Barrenia taeda | CM14P64 | Pinus rigida, root | New Jersey Pine Barrens, USA | — | — | — |
| Barrenia taeda | WSF14P13 | Pinus rigida, root | New Jersey Pine Barrens, USA | — | — | — |
| Barrenia taeda | WSF14P22 | Pinus rigida, root | New Jersey Pine Barrens, USA | — | — | — |
| Botryotinia fuckeliana | | | Oregon, USA | | AY544651 | |
| Bulgaria inquinas | CBS118.31 | | Germany | | DQ470960 | AFTOL916 |
| Chloroscypha chloromela | | | Oregon, USA | U92311 | | |
| Chlorovibressea sp. | | | New Zealand | | DQ257352 | |
| Collembolispora aristata | | foam in stream | Nova Ves, Czech Republic | | KC005811 | |

TABLE 3-continued

Species name, isolate number, host, location and GenBank accession numbers of the fungi used in this study.

| Species | Isolate number [a] | Host | Location | ITS | LSU | RPB1 |
|---|---|---|---|---|---|---|
| Cudoniella clavus | AFTOL166 | Hemlock cones and small sticks | Benton County, Oregon, USA | | DQ470944 | DQ471128 |
| Dermea acerina | CBS161.38 | Acer rubrum | Bear Island, Ontario, Canada | AF141164 | DQ247801 | DQ471164 |
| Fabrella tsugae | | | | | AF356694 | |
| Hyaloscypha aureliella | | | Scotland | JN943611 | EU940152 | JN985241 |
| Hyaloscypha vitreola | | | Kaarina, Finland | FJ477059 | FJ477058 | |
| Lachnum virgineum | AFTOL49 | Alnus sp., cones | Oregon, USA | DQ491485 | AY544646 | DQ842030 |
| Lambertella subsubrenispora | CBS811.85 | Aster ageratoides var. ovata | Honshu, Japan | | DQ470978 | |
| Leotia lubrica | AFTOL1 | Chrysolepis chrysophyla | Oregon, USA | | AY544644 | |
| Loramyces macrosporus | CBS235.53 | Equisetum limosum | UK | DQ471005 | DQ470957 | DQ471149 |
| Microglossum rufum | AFTOL1292 | | Tennessee, USA | | DQ470981 | DQ471179 |
| Mollista cinerea | CBS122029 | fallen log | Alsea Falls, Oregon, USA | DQ491498 | DQ470942 | DQ471122 |
| Mollisia dextrinospora | ICMP18083 | Actinidia deliciosa cv. Hayward | New Zealand | | HM116757 | |
| Monilinia laxa | CBS122031 | | | | AY544670 | FJ238425 |
| Neobulgaria lilacina | | | Finland | | EU940141 | |
| Neobulgaria pura | CBS477.97 | log with moss | New York, USA | | FJ176865 | |
| Neofabrea malicorticis | CBS122030 | Malus sp. | Oregon, USA | | AY544662 | |
| Phialocephala dimorphospora | CBS300.62 | slime in pulp mill | | AF486121 | AB671465 | |
| Phialocephala fortinii | CBS443.86 | Pinus sylvestris, root | Suonenjoki, Finland | AB671499 | AB671466 | |
| Phialocephala scopiformis | CBS468.94 | Picea abies, bark | Regensburg, Germany | AF486126 | | |
| Spathularia velutipes | | Tsuga Canadensis | Tennessee, USA | | FJ99786 | |
| Varicosporium elodeae | | | Svalbard, Norway | | JN941371 | |
| Vibressea truncorum | CBS258.91 | Populus, submerged root | Ontario, Canada | EU434854 | FJ176874 | FJ238438 |
| Acephala sp.[c] | | Cymbidium insigne | China | HQ889709 | | |
| Acephala sp.[c] | | Sugarcane, root | Brazil | GU973749 | | |
| Phialocephala sp.[c] | | Rhododendron, root | Smoky Mountain National Park, USA | JQ272328 | | |

[a] AFTOL = Assembling the Fungal Tree of Life project; ATCC = American Type Culture Collection, Manassas, Virginia, USA; CBS = Centraalbureau voor Schimmelcultures, Utrecht, The Netherlands; ICMP = International Collection of Micro-organisms from Plants, Lincoln, New Zealand.
[b] Numbers in boldface indicating new sequences from this study.
[c] Taxon name was copied from GenBank. Phylogenetic analysis in this study indicated that they belong to Barrenia.

Plant-fungal Interaction Experiment

Fungal isolates WSF1R37, WSF14P22, and *A. panicicola* isolate 61R8 were used in the seedling inoculation experiment. Switchgrass ('Kanlow') seeds were surface disinfected as follows: 95% ethanol for 30 s, 0.5% NaOCl for 1 min, 70% ethanol for 1 min, rinsed with sterile distilled $H_2O$ and allowed to germinate in the dark at 25° C. for 3 days. Agargel (Sigma-Aldrich, USA) plates were made following manufacturer's instructions, and were cut in half, with one side removed. On the cut surface of an Agargel plate, three 10 mm×10 mm×5 mm plugs from a one-week old fungal culture grown on MEA were placed equidistance from one another. Germinated switchgrass seeds with visible radicle were then placed on the plugs. Sterile MEA plugs were used as negative control. Cultures were incubated at 25° C. under 12 hr light and dark cycle with nine replicates. Root length was measured 7 days after inoculation.

The following examples are provided to illustrate certain embodiments of the invention. They are not intended to limit the invention in any way.

EXAMPLE I

*Barrenia*, a New Genus Associated with Roots of Switchgrass and Pine in the Oligotrophic Pine Barrens, Promotes Root Hair Growth A. Culture Morphology and Growth Rate Isolate WSF1R37 produced dense Cinnamon Brown mycelium on MEA, and Ochraceous Tawny mycelium on WA. Colony diameter measurements for isolate WSF1R37 after 20 days were 75 mm on average on MEA with standard deviation (SD) of 2.6, and 47 mm on average on WA with SD of 2.6. Isolate WSF14P22 produced dense Cinnamon Brown mycelium on MEA, and Buckthorn Brown mycelium on WA. Colony diameter measurements for isolate WSF14P22 after 20 days were 28 mm on average on MEA with SD of 0.6, and 26 mm on average on WA with SD of 1.0.

B. Sequence Data and Phylogeny

Figure 1:
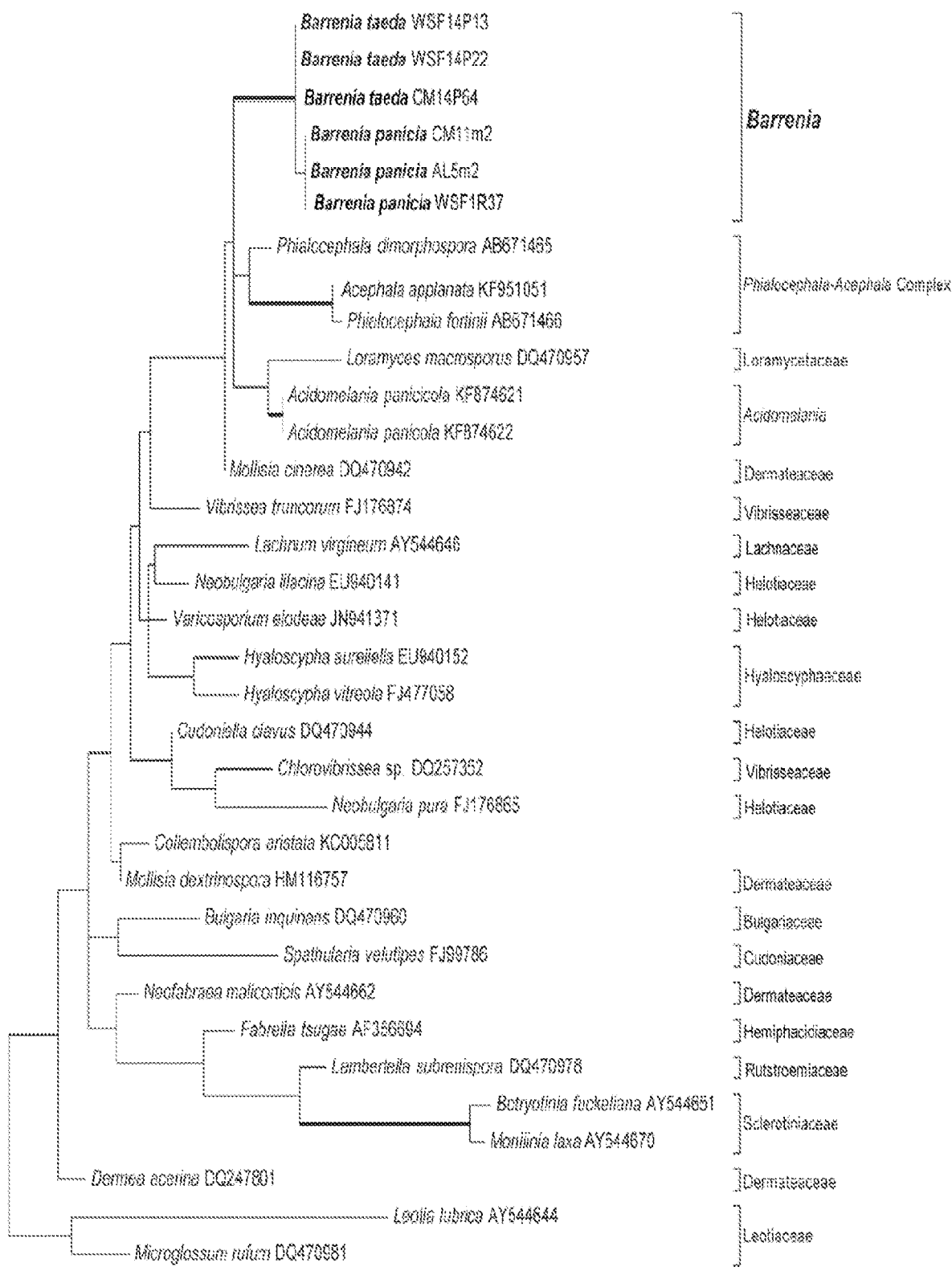
FIG. 1. Maximum likelihood phylogenetic tree inferred from the large subunit of rRNA gene sequence. Bootstraps higher than 70 have thickened branches.
Figure 2:
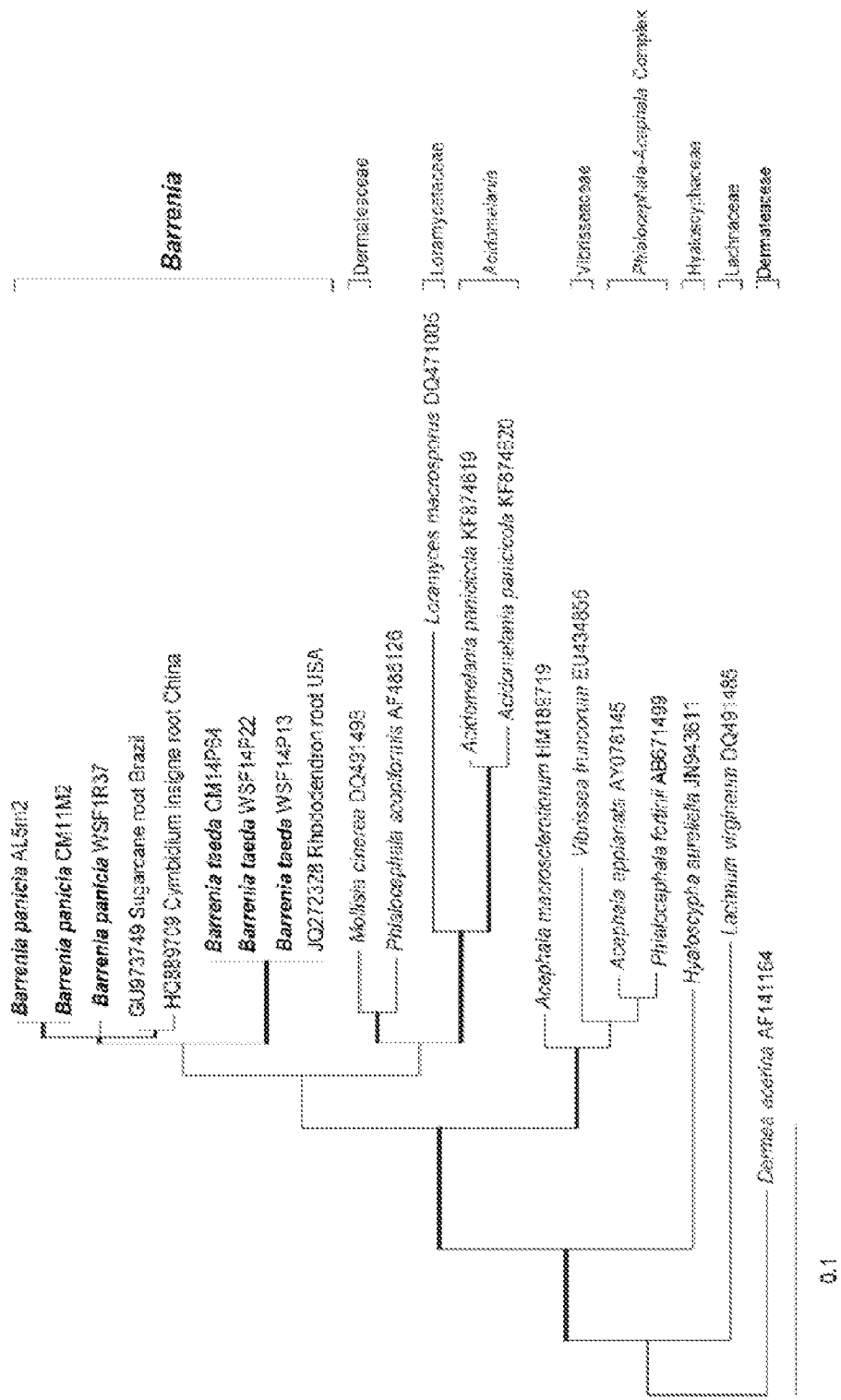
FIG. 2. Maximum likelihood phylogenetic tree inferred from the internal transcribed spacer sequences of rRNA gene. Bootstraps higher than 70 have thickened branches.
Figure 3:
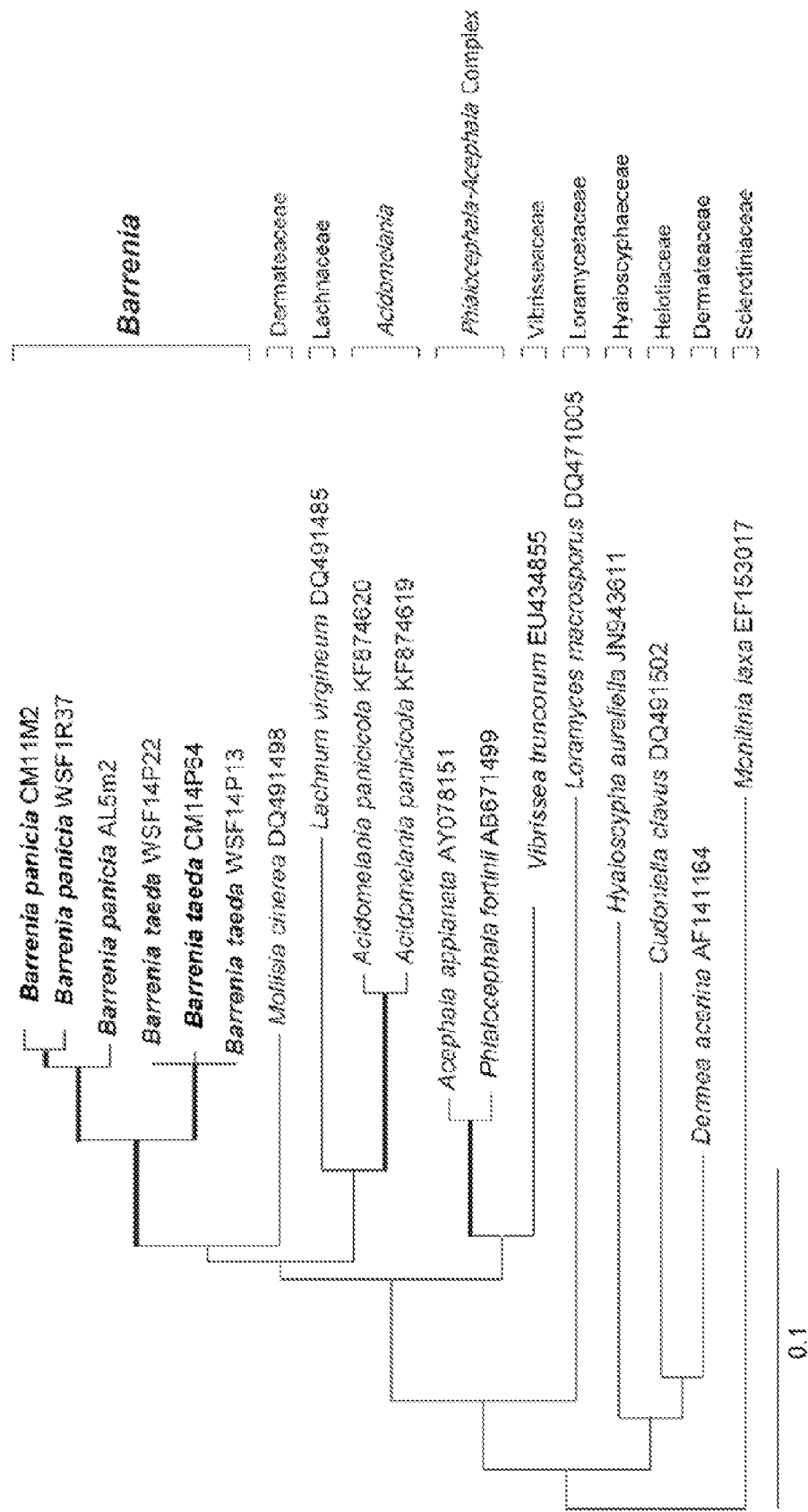
FIG. 3. Maximum likelihood phylogenetic tree inferred from combined ITS, LSU, and RPB1 gene sequence datasets. Bootstraps higher than 70 have thickened branches.

There were 173 characters in the LSU alignment, 377 in ITS and 1291 in the three-gene alignment. Maximum likelihood trees based on LSU, ITS and three gene sequences are shown in FIGS. 1-3. All three phylogenies supported that the new isolates formed a monophyletic clade in *Helotiales* separated from any known taxa. The LSU tree indicated that they were close to *Acidomelania panicicola*, *Loramyces macrosporus*, *Mollisia cinerea* and PAC. The ITS tree showed that these new isolates were closely related to *A. panicicola*, *M. cinerea*, *Phialocephala scopiformis* and *L. macrosporus*. In the ITS tree, isolates WSF1R37, AL5m2, and CM11m2 formed a well-supported group, while isolates WSF14P22, WSF14P13, and CM14P64 formed another. The two groups were also recognized and supported by the LSU and RPB1 trees, and variation in the phylogenetic relationships of these isolates only occurred within the groups. DNA sequence information for the different fungal species is displayed in FIGS. 4A-4R.

Based on the molecular phylogenetic analyses, morphological characters and their ecological features, a new genus and two new species have been identified. *Barrenia* differs from *Loramyces* by its association with living plant roots while *Loramyces* species are associated with submerged dead plants (Digby and Goos 1987; Ingold and Chapman 1952; Weston 1929). Taxa in the PAC are also root endophytes, but they exhibit complex phialid arrangements that appear to be lacking in *Barrenia*. *Barrenia* also differs from *Mollisia* because of its lack of phialide producing conidia. Moreover, *Barrenia* has 93% or less ITS sequence similarity to the above-mentioned close relatives or any other described species with accessible ITS sequences. The two *Barrenia* species differ from each other on host and growth rate. The pine associated *B. taeda* exhibited slower growth than the grass associated *B. panicia* on both WA and MEA. There is a 96% similarity in ITS sequences between *B. panicia* and *B. taeda*.

C. Plant-Fungal Interaction Experiment

Switchgrass seedlings inoculated with *A. panicicola* isolate 61R8 and *B. panicia* WSF1R37 produced dense root hairs all the way to the root apical meristem area, while the control seedlings only produced dense root hairs at the region of maturation of the root (FIGS. 5A and 5C). In addition, the roots inoculated with *A. panicicola* isolate 61R8 and *panicia* WSF1R37 had a serpentine growth pattern, while the control roots were straight. Hyphopodia-like strutures were observed on the switchgrass seedling roots inoculated with *B. panicia* WSF1R37 (FIG. 6A-6C). Root length for seedlings inoculated with *B. panicia* WSF1R37 after 7 days were 17.4 mm on average with SD of 1.8, not significantly different from the control, which was 19 mm on average with SD of 5.1. Seedlings inoculated with *B. taeda* WSF14P22 showed no difference in root hair production with the control. Root length for *B. taeda* WSF14P22 after 7 days was 8.1 mm on average with SD of 1.6, which was significantly shorter than the control (FIG. 5E).

Discussion

Our recent survey on fungi associated with grass roots uncovered a number of novel DSE in *Leotiomycetes* from the pine barrens ecosystem (Luo et al. 2014a, 2014b; Walsh et al. 2014). *Leotiomycetes* are morphologically and ecologically diverse and the phylogenetic relationships within this class are not well resolved due to lack of molecular data (Wang et al. 2006). Based on the multi-locus phylogenetic analyses, the new genus *Barrenia* described here belongs to *Helotiales*, which encompasses plant pathogens, saprobes and endophytes. The dark, septate hyphal morphology of *Barrenia* spp., their root-colonizing habit and phylogenetic closeness to PAC indicate that they likely are also DSE.

The best studied DSE is the PAC, specifically *P. fortinii*. However, the ecological functions of PAC and other DSE remain elusive. Host-fungal interaction experiments often yielded inconsistent results under various experimental conditions in different laboratories (Mandyam and Jumpponen 2005). This prompted us to examine the interaction between *B. panicia*, *B. taeda*, *A. panicicola* and switchgrass, which is the host of *B. panicia* and *A. panicicola*. Our inoculation results indicated that *A. panicicola* and *B. panicia* remarkably promoted the root hair growth in switchgrass. In switchgrass roots, *B. panicia* produced hyphopodium-like structures, which may perform penetration and nutrient exchange function between the fungus and the host plant (Delaux et al. 2013; Walker 1980). *Barrenia taeda*, originally isolated from pine roots, had negative effect on root elongation in switchgrass seedlings. These results corroborate Mandyam et al. (2010; 2012) that while DSE fungi have a broad host range, their effects and characteristics can be considered host specific.

The phylogenetic analysis in this study indicated that *Barrenia* is close to *Acidomelania*, *Loramyces*, *Mollisia*, and PAC. The phylogenetic proximity of *Mollisia*, *Loramyces* and PAC was also supported by Zijlstra et al. (2005) and Wang et al. (2006). *Barrenia* can be distinguished from *Loramyces* and *Mollisia* by its association with living plant roots. While taxa in PAC also are root endophytes, morphologically they can be distinguished from *Barrenia*. In addition, *Barrenia* has 93% or less ITS sequence similarities to the above-mentioned close relatives or any other described species with accessible ITS sequences. The family placement of *Barrenia* is not determined here because the *Leotiomycetes* phylogeny is poorly resolved and several families in this class likely are polyphyletic (Wang et al. 2006).

The six *Barrenia* isolates from New Jersey Pine Barrens were grouped into two well-supported clades. We delimited the two species based on the genealogical concordance phylogenetic species recognition (Taylor et al. 2000). The BLAST results in GenBank indicated that *Barrenia* might have a wide distribution. Sixteen ITS sequences in GenBank had 97-99% identity with that of *B. panicia* isolate WSF1R37, for example, GU973749 from sugarcane root in Brazil, HQ889709 from *Cymbidium insigne* root in China, and AY599235 from grass root in The Netherlands. Twelve ITS sequences in GenBank had 97-99% identities with that of *B. taeda* isolate WSF14P22, for example, JQ272328 from

*Rhododendron* root in USA and KJ817299 from *Vaccinium vitis-idaea* in Inner Mongolia. The host plants of the matched sequences in GenBank are largely Ericaceae, terrestrial orchids, grasses and conifers, usually found in acidic and infertile soils (Keddy 2007). This distribution pattern was also found in *Acidomelania panicicola*, the other root associated fungus frequently isolated from the pine barrens (Walsh et al. 2014).

Additional experiments to uncover fungal-plant interactions included the inoculation of switchgrass seedlings with *A. panicicola* isolate 61R8 and *B. panicia* WSF1R37 produced dense root hairs all the way to the root apical meristem area, while the control seedlings only produced dense root hairs at the region of maturation of the root. In addition, the roots inoculated with *A. panicicola* isolate 61R8 and *B. panicia* WSF1R37 had a serpentine growth pattern, while the control roots were straight. The plant growth promotion effect of *A. panicicola* and *B. panicia* discovered in this study coupled with their distribution pattern indicate that these species may play a role in plant adaptation to acid, low nutrient soils.

In conclusion, we discovered a new genus and two species of root-colonizing fungi associated with plants living in an acidic, nutrient poor environment. The phylogenetic and taxonomic work and the plant-fungal interaction results reported here will aid future ecological and evolutionary studies on root-associated fungi.

EXAMPLE II

Endophytic Fungi from Pine Barrens Grasses Promote Plant Growth in Acidic, High Aluminum Toxicity and Low Nutrient Conditions A. Fungal Inoculation of Seeds on Agar In this study, we performed functional studies that demonstrated that *Acidomelania panicocola* inoculation of seeds significantly increased root hair growth in switchgrass, rice and lettuce seedlings compared to the control.

Figure 7:
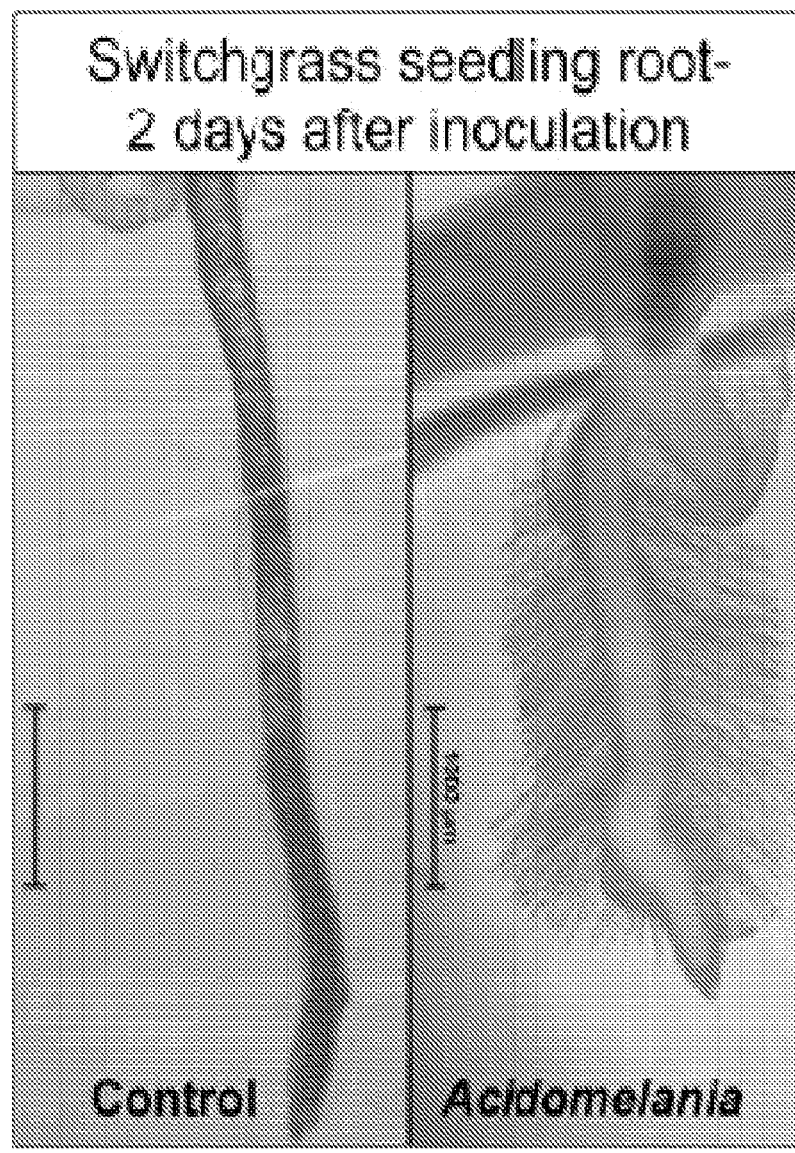

To assess the effects of *Acidomelania panicicola* inoculation of switchgrass and rice seedlings on root hair abundance, fungus was grown on water agar under room temperature for 7 days. Seeds were germinated in sterile distilled water in a petri dish under room temperature in the dark for 7 days. Seedlings (roots down) were inserted in the 7 day-old fungal agar culture. Control seedlings were uninoculated but grown under the same conditions. Significant differences in root hair abundance were observed in inoculated seedlings when compared to negative, untreated controls (FIGS. 7 and 8). These findings indicate that *Acidomelania panicicola* inoculation enhances root hair abundance.

To evaluate switchgrass seedling survival percent and root and shoot length, switchgrass seeds were next inoculated with *Acidomelania panicicola* or *Fusarium oxysporum* or uninoculated using the method described above and agar and seedlings were covered with top soil. 6 days post-inoculation, *Acidomelania panicicola* inoculated seedlings exhibited a significant increase in survival (FIG. 9). Root and shoot length of switchgrass seedlings were visualized 8 days after inoculation when enhanced root and shoot length were observed (FIG. 10). These results demonstrate that colonization of switchgrass seedlings with *Acidomelania panicicola* enhances switchgrass growth and survival.

To assess the effects of *Acidomelania panicicola* inoculation on lettuce seed growth, seeds were inoculated and germinated as described above. Root length was assessed 4 days after inoculation. Increased root growth was observed for the inoculated lettuce seedlings (FIG. 11). These findings indicate that *Acidomelania panicicola* can enhance growth of edible plants.

B. Bacterial and Fungal Mixing and Inoculation of Seeds

Fungus (e.g. *Acidomelania panicicola*) is grown on water agar or other growth media under room temperature for 7 days. Bacterium (e.g. *Burkholderia* sp.) is cultured in Luria-Bertani broth (LB) overnight at 28° C. Seeds are mixed with the bacterial culture and the fungal cultures (ratio: 500 seeds: 10 mL overnight bacterial culture: 1 Petri dish 7 day old fungal culture) and placed on soil (e.g. Pine Barrens soil or other nutrient-poor soils). Seeds are then covered with top soil and grown under sufficient light.

C. Bacterial and Fungal Mixing, Inoculation and Drying of Seeds

Fungus (e.g. *Acidomelania panicicola*) is grown on water agar or other growth media under room temperature for 7 days. Bacteria (e.g. *Burkholderia* sp.) are grown in Luria-Bertani broth (LB) overnight at 28° C. Seeds are mixed with the bacterial culture and the fungal cultures (ratio: 500 seeds: 10 mL overnight bacterial culture: 1 Petri dish 7 day old fungal culture) and dried. Seeds are placed on soil (e.g. Pine Barrens soil or other nutrient-poor soils). Seeds are then covered with top soil and grown under sufficient light.

D. Bacterial and Fungal Mixing, Inoculation of Soil Formulated with Vermiculite and Rock Phosphate Fungus (e.g. *Acidomelania panicicola*) is grown on water agar or other growth media under room temperature for 7 days. Bacterium (e.g. *Burkholderia* sp.) are grown in Luria-Bertani broth (LB) overnight at 28° C. Soil formulated with vermiculite and rock phosphate is inoculated with the fungal and bacterial cultures.

Discussion

Roots were an early development in plant life evolving on land during the Devonian Period (416 to 360 million years ago; (von Uexkull et al. 1995)). The fossil record and molecular phylogenetic analysis suggest that from the outset, mycorrhizal fungi played a crucial role in facilitating plant invasion of land, which was dry and poor in nutrients at the time of colonization (Gensel et al. 2001). Such drought and low nutrient stress continue to challenge plants living in many extant habitats.

We describe herein a novel endophytic fungi, *Acidomelania panicicola*, for use alone, and optionally in the presence bacteria, which enter the root-interior and colonize the tissues of the plant, thereby effectively promoting plant growth and survival. Given that there are limited techniques—both time consuming and cost-intensive—to prevent adverse effects of abiotic stressors on plant growth, the present studies demonstrating that application of a biofertilizer comprising *Acidomelania* to seeds or seedlings results in increased seedling survival rate, root hair abundance, and root and shoot length will have great utility for promoting plant growth under adverse environmental conditions.

EXAMPLE III

Liquid Formulation of the BioFertilizer for Seed Coating

This example provides a liquid formulation of biofertilizer, where the formulation consists of two separate solutions that are combined before use as a seed coating.

For the first solution, the fungi are grown in a 1 L flask using an adequate medium and are concentrated by centrifugation in order to separate the solid. This solid is then suspended in a minimum amount of media. A sun protecting product, such as Congo red or green colorant can also be added to the media at 1% (w/v).

According to one preferred embodiment, *A. panicicola* only is used for the first solution in similar initial concentrations. In a second embodiment, the first solution contains a fungus from the genus *Barrenia* only (e.g. *B. panicia*). In another embodiment, the first solution is comprised of *A. panicicola* and at least one fungus from the genus *Barrenia* (e.g. *B. panicia*). In another embodiment, the first solution contains a mixture of *A. panicicola* and at least one bacteria from the genus *Burkholderia*. In another embodiment, a mixture of *B. panicia* and at least one bacteria from the genus *Burkholderia* is contained within the first solution.

For the second solution, a 1% (w/v) solution of a polysaccharide, such as guar gum, gelan gum, pectin, carboxymetil cellulose, agar-agar, xantan gum (or other food hydrocolloid) is prepared to be used as sticker. The two solutions are then mixed together to treat plant seeds as a coating. The seed should be dried before planting and it is preferable to wait at least two hours after application prior to planting.

EXAMPLE IV

Solid State Formulation of the Biofertilizer of the Invention

This example provides a liquid formulation of a biofertilizer where the fungi and optionally bacteria are encapsulated and the fertilizer is in solid form. Alginate beads were prepared as follows: 1 ml of 30% glycerol was added to 1, 1.5 or 2% sodium alginate solution, depending on the alginate properties (M/G ratio) to obtain a final volume of 25 ml. Then, 250 ml of culture (obtained from a culture of *A. panicicola* only, a fungus from the genus *Barrenia* only (e.g. *B. panicia*), or a mixture of *A. panicicola* and *Burkholderia*, or a mixture of *A. panicicola* and *Barrenia* (e.g. *B. panicia*) was centrifuged, the cell pellet was washed with saline (0.85% NaCl, w/v) and suspended in 25 ml of alginate mixture and mixed thoroughly. This suspension was added drop wise into a pre-cooled sterile 1.5 or 2% (w/v) aqueous solution of $CaCl_2$ under mild agitation to obtain the fungal-alginate beads. These beads were allowed to harden for 2-4 h at room temperature. Beads were collected by sieving and were washed several times with sterile water and stored at 4° C. In order to preserve the formulation, the fresh wet beads were frozen at −80° C. prior to lyophilization at −45° C. for 15 h. The lyophilized dry beads were stored in sterile glass bottles.

REFERENCES

Blackwell M. 2011. The Fungi: 1, 2, 3 . . . 5.1 Million Species? Am J. Bot. 98:426-438.

Delaux P M, Sejalon-Delmas N, Becard G, Ane J M, 2013. Evolution of the plant-microbe symbiotic 'toolkit'. *Trends in Plant Science* 18:298-304.

Digby S, Goos R, 1987. Morphology, development and taxonomy of *Loramyces. Alycologia* 79:821-831

Dighton J, Tuininga A R, Gray D M, Huskins R E, Belton T, 2004. Impacts of atmospheric deposition on New Jersey pine barrens forest soils and communities of ectomycorrhizae. *Forest Ecology and Management* 201:131-144.

Edgar R C, 2004. MUSCLE: multiple sequence alignment with high accuracy and high throughput. *Nucleic Acids Research* 32:1792-1797.

Forman R T, 1998. *Pine Barrens: Ecosystem and Landscape*. Rutgers University Press, New Jersey.

Gensel, P. G., Kotyk, M. E., Basinger, J. F. 2001. Morphology of Above and Below Ground Structures in Earl Devonian (Pragian-Emsian) Plants, in: P G G D E (Eds), Plants Invade the Land: Evolutionary and Environmental Perspectives. Columbia University Press, New York, pp. 83-102.

Grünig C R, Duo A, Sieber T, Holdenrieder 0, 2008a. Assignment of species rank to six reproductively isolated cryptic species of the *Phialocephala fortinii* s.1.-*Acephala applanata* species complex. *Mycologia* 100:47-67.

Grünig C R, Queloz V, Sieber T N, Holdenrieder 0, 2008b. Dark septate endophytes (DSE) of the *Phialocephala fortinii* s.1.-*Acephala applanata* species complex in tree roots: classification, population biology, and ecology. *Botany* 86:1355-1369.

Hall B D, Stiller J W, 1997. The origin of red algae: Implications for plastid evolution. *Proceedings of the National Academy of Sciences of the USA* 94:4520-4525.

Ingold C T, Chapman B, 1952. Aquatic Ascomycetes: *Lorwnyces juncicola* Weston and *L. macrospora* n. sp. *Transactions of the British Mycological Society* 35:268-272

Keddy P A, 2007. Plants And Vegetation: Origins, Processes, Consequences. Cambridge University Press, U K.

Knapp D G, Pintye A, Kovacs G M, 2012. The dark side is not fastidious—dark septate endophytic fungi of native and invasive plants of semiarid sandy areas. PLoS ONE 7:e32570.

Luo J, Walsh E, Naik A, Zhuang W, Zhang K, Cai L, Zhang N, 2014a. Temperate pine barrens and tropical rain forests are both rich in undescribed fungi. PLoS ONE 9:e103753.

Luo J, Walsh E, Zhang N, 2014b. Four new species in Magnaporthaceae from grass roots in New Jersey Pine Barrens. *Mycologia* 106: 580-588.

Mandyam K, Fox C, Jumpponen A, 2012. Septate endophyte colonization and host responses of grasses and forbs native to a tallgrass prairie. *Mycorrhiza* 22:109-119.

Mandyam K, Jumpponen A, 2005. Seeking the elusive function of the root-colonising dark septate endophytic fungi. *Studies in Mycology* 53:173-189.

Mandyam K, Loughin T, Jumpponen A, 2010. Isolation and morphological and metabolic characterization of common endophytes in annually burned tallgrass prairie. *Mycologia* 102:813-821.

Matheny P L, Liu Y J, Ammirati J F, Hall, B D, 2002. Using Rpb1 Sequences To Improve Phylogenetic Inference Among Mushrooms (*Inocybe, Agaricales*). *American Journal of Botany* 89:688-698.

Menkis A, Allmer J, Vasiliauskas R, Lygis V, Stenlid J, Finlay R, 2004. Ecology and molecular characterization of dark septate fungi from roots, living stems, coarse and fine woody debris. Mycological Research 108:965-973.

Otgonsuren B, Lee M J, 2013. Ectomycorrhiza Enhanced the Cold-Acclimation Growth and Freeze Tolerance of Scots Pine (*Pinus sylvestris* L.). *Taiwan Journal of Forest Science* 28:97-111.

Rehner S A, Samuels G J, 1995. "Molecular systematics of the Hypocreales—a teleomorph gene phylogeny and the status of their anamorphs." *Canadian Journal of Botany* 73:S816-S823.

Ridgway R, 1912. *Color standards and color nomenclature*. The author, Washington D. C.

Stoyke, G, Currah, R. S. 1991. Endophytic Fungi from the Mycorrhizae of Alpine Ericoid Plants. Can. J. Bot. 69: 347-352.

Tamura K, Stecher G, Peterson D, Filipski A, Kumar S, 2013. MEGA6: Molecular Evolutionary Genetics Analysis version 6.0. Molecular Biology and Evolution 30:2725-2729.

Taylor J W, Jacobson D J, Kroken S, Kasuga T, Geiser D M, Hibbett D S, Fisher M C, 2000. Phylogenetic species recognition and species concepts in fungi. Fungal Genetics and Biology 31:21-32.

Tedrow J C F, 1952. Soil Conditions in the Pine Barrens of New Jersey. Bartonia 26: 28-35.

Tuininga, A. R., Dighton, J. 2004. Changes In Ectomycorrhizal Communities and Nutrient Availability Following Prescribed Burns in Two Upland Pine-Oak Forests In the New Jersey Pine Barrens. Can J. Forest Res. 34: 1755-1765.

von Uexkull, H. R., Mutert, E. 1995. Global Extent, Development and Economic-impact of Acid Soils. Plant Soil. 171:1-15.

Walker J, 1980. Gaeumannomyces, Linocarpon, Ophiobolus and several other genera of scolecospored ascomycetes and Phialophora conidial states, with a note on hyphopodia. Mycotaxon 11:1-129.

Walsh E, Luo J, Zhang N, 2014. Acidomelania panicicola gen. et sp. nov. from switchgrass roots in acidic New Jersey pine barrens. Mycologia 106:856-864.

Wang Z, Johnston P R, Takamatsu S, Spatafora J W, Hibbett D S, 2006. Toward a phylogenetic classification of the Leotiomycetes based on rDNA data. Mycologia 98:1065-1075.

Weston W H, 1929. Observations on Loramyces, an undescribed aquatic ascomycete. Mycologia 21:55-76.

White T J, Bruns T, Lee S, Taylor J, 1990. Amplification and direct sequencing of fungal ribosomal RNA genes for phylogenetics. In: Innis M, Gelfand D, Sninsky J, White T (eds) PCR Protocols: A Guide to Methods and Applications. New York: Academic Press.

Yu T, Nassuth A, Peterson R L, 2001. Characterization of the interaction between the dark septate fungus Phialocephala fortinii and Asparagus officinalis roots. Canadian Journal of Microbiology 47:741-753.

Zijlstra J, Van't Hof P, Baar J, Verkley G, Summerbell R, Paradi I, Braakhekke W, Berendse F, 2005. Diversity of symbiotic root endophytes of the Helotiales in ericaceous plants and the grass, Dechampsia flexuosa. Studies in Mycology 53:147-162.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A biofertilizer composition for application to seeds, plant surfaces, and/or soil, comprising an effective amount of *A. panicicola* and at least one agent or microorganism for promoting plant growth and resistance to abiotic stresses, wherein the composition comprises alginate and is optionally used as a seed coating.

2. The biofertilizer composition of claim 1, wherein the composition contains *A. panicicola* and at least one *Burkholderia* species in equal concentrations.

3. The biofertilizer composition of claim 2, comprising, a sun protecting product.

4. The biofertilizer composition, according to claim 1, wherein said at least one microorganism is of the genus *Barrenia*.

5. The biofertilizer of claim 4, wherein said at least one microorganism of the genus *Barrenia* is *Barrenia panicia*.

6. The biofertilizer composition of claim 1, wherein the composition contains *A. panicicola* and at least one *Barrenia* species in equal concentrations.

7. The biofertilizer composition of claim 4, further comprising a sun protecting product and a polysaccharide solution.

8. The biofertilizer composition of claim 7, wherein the polysaccharide is selected from the group consisting of guar gum, gelan gum, pectin, carboxymetil cellulose, agar, and xanthan gum and contains 1% w/v of a polysaccharide.

9. The biofertilizer composition of claim 8 applied to seeds as a coating.

10. The biofertilizer composition of claim 4, wherein said *A. panicicola*and said microorganism of the genus *Barrenia* are encapsulated in alginate beads.

11. The composition of claim 1, further comprising at least one of a gel formulation, agar, vermiculite, a sun protectant, rock phosphate, and a polysaccharide solution.

12. A biofertilizer composition comprising an effective amount of *A. panicicola*, at least one agent or microorganism for promoting plant growth and resistance to abiotic stresses, and 1% w/v of a polysaccharide selected from the group consisting of guar gum, gelan gum, pectin, carboxymetil cellulose, agar, and xanthan gum.

13. The composition of claim 12, wherein said at least one microorganism is a *Burkholderia* species.

14. The composition of claim 12, wherein said at least one microorganism is a fungus of the genus *Barrenia*.

15. The composition of claim 14, wherein the fungus is *Barrenia panicia*.

16. A biofertilizer composition comprising an effective amount of *A. panicicola* and at least one agent or microorganism for promoting plant growth and resistance to abiotic stresses, wherein the composition is applied as a seed coating and improves seed germination.

17. The composition of claim 16, wherein said at least one microorganism is a *Burkholderia* species.

18. The composition of claim 16, wherein said at least one microorganism is a fungus of the genus *Barrenia*.

19. The composition of claim 18, wherein the fungus is *Barrenia panicia*.

20. A method for enhancing overall plant growth and resistance to adverse abiotic conditions comprising contacting a plant or seed therefrom with the composition of claim 12.

21. The method of claim 20, wherein said composition contains bacteria selected from the *Burkholderia* genus.

22. The method of claim 20, wherein the crop plants are dicotyledonous plants or monocotyledonous plants.

23. The method of claim 22, wherein said plant is an edible plant selected from lettuce, corn, rice, soybeans, potatoes, barley, wheat, and carrots.

24. The method of claim 20 wherein said plant is a turfgrass plant selected from a Ryegrass, Kentucky Bluegrass, Tall Fescue, Bermuda, St. Augustine or Zoysia plant or any other turfgrass plant.

25. The method of claim 20, wherein said composition contains fungi selected from the *Barrenia* genus.

26. The method of claim 25, wherein the fungi is *Barrenia panicia.*

27. The method of claim 25, wherein said composition contains bacteria selected from the *Burkholderia* genus.

* * * * *

SEQUENCE LISTING

<160> NUMBER OF SEQ ID NOS: 18

<210> SEQ ID NO 1
<211> LENGTH: 1889
<212> TYPE: DNA
<213> ORGANISM: Acephala applanata

<400> SEQUENCE: 1

```
gtgtttacat actattgttg ctttggcggg ccgtgacctc cactgcgggc tctgctcgtg      60
tgtgcccgcc agaggaccaa actctgaatg ttagtgatgt ctgagtacta tctaatagtt     120
aaaactttca acaacggatc tcttggttct ggcatcgatg aagaacgcag cgaaatgcga     180
taagtaatgt gaattgcaga attcagtgaa tcatcgaatc tttgaacgca cattgcgccc     240
tgtggtattc cgcagggcat gcctgttcga gcgtcattta accactcacg cctggcgtgg     300
tattggggta cgcggtctcg cggccctcaa aatcagtggc ggtgccggtg ggctctaagc     360
gtagtacata ctcccgctat agagttcccc cggtggctcg cacccgctga acttaagcat     420
atcaataagc ggaggaaaag aaaccaacag ggattacctc agtaacggcg agtgaagcgg     480
taacagctca aatttgaaag ctgccaacag gccgcgttgt aatttgtaga rgctgctttg     540
ggtgtcggcc cggtctaagt tccttggaac aggacgtcat agagggtgag aatcccgtat     600
gtgatcggtg ccgttgcccg tgtaaagcgc tttcgacgag tcgagttgtt tgggaatgca     660
gctcaaaatg ggtggtaaat ttcatctaaa gctaaatatt ggccagagac cgatagcgca     720
caagtagagt gatcgaaaga tgaaaagcac tttggaaaga gagttaaaca gtacgtgaaa     780
ttgttgaaag ggaagcgctt gcaaccagac ttgcgggcg tcgatcatcc gaggttctcc     840
ccggtgcact cgatcgttct caggccagca tcggtttccg gggtgggata aaggcggtgg     900
gaatgtggct cttcggagtg ttatagccca ccgtgcaatg ccgccaccgg ggaccgagga     960
ccgcgcttcg gctaggatgc tggcgtaatg gttgtaagcg acccgtcttg aaacacggac    1020
```

```
caaggagtct aacatctatg cgagtgtttg ggtgtcaaac ccatacgcgt aatgaaagtg   1080 aacgaggta agagccctt agggtgcatt atcgaccgat cctgatgtct tcggatggat    1140
ttgagtaaga gcatagctgt tgggacccga aagatggtga actatgcgtg aatagggtga   1200
agccagagga aactctggtg gaggctcgca gcggttctga cgtgcaaatc gatcgtcaaa   1260
tttgcgtata ggggcgaaag actaatcggc tagacagagt cagttcgccc gatgagggtg   1320
gcagatctac ttgttctygt gctgacatga gtatctcaga gtaatccggc cttcaaagca   1380
gctgtttcca ttcgagaccc gaagcgtagg ttcgatacga tttggcgact ttgcaagccc   1440
aagatgatct gcgatagcga cgtttctgcg gacgatcaag aattcggtgg cgatccaaag   1500
gaagccgtga agcgctctca tggaggctgt ggaaatactc agcccgaggt gcgccagcag   1560
gctctgcagc tttggggtac atggaagatg cctaaggacg aggagaacga gggaagccaa   1620
tccgagaaga gacaaatcac tccagagatg gctctgaacg tcttccgaag catgtctact   1680
gctgagattc gcgaccttgg gttgagcaac gattatgccc gacccgactg gctgatcatc   1740
acagtccttc cagttcctcc tccgccggtt cgaccaagta tctcaatgga tggcacaagc   1800
acaggcatgc gtggagarga tgatttgacg tacaagctcg gtgatatcat ccgtgcgaac   1860
ggcaatgtca agcaggcaca acaggaagg                                    1889

<210> SEQ ID NO 2
<211> LENGTH: 1943
<212> TYPE: DNA
<213> ORGANISM: Acidomelania panicicola

<400> SEQUENCE: 2
gtgtctacat actcttgttg ctttggcagg ccgtggcctc ccactgtggg ctcagcctgc     60
atgtgcctgc cagaggacca aactctgaat gttactgatg tctgagtact atataatagt    120
taaaactttc aacaacggat ctcttggttc tggcatcgat gaagaacgca gcgaaatgcg    180
ataagtaatg tgaattgcag aattcagtga atcatcgaat ctttgaacgc acattgcacc    240
cggtggtatt ccgccgggta tgcctgttcg agcgtcatta caaccactca agcctgtctt    300
ggtgttgggg attgcgaatc tcgcagcccct agagtccagt agcgtcacct ttaggtccta    360
agcgtagtaa tttctcctcg ctacagaacc tgccggtgga tagtataaat ccagttaagt    420
ctggtatccc gcggttgacc tcggatcaag tagggatacc cgctgaactt aagcatatca    480
ataagcggag gaaagaaac caacagggat tactttagta acggcgagtg aagcggtaac    540
tgctcaaatt tgaaagctgc aacaggccg cgttgtaatt tgtagaagat gctttgggtg    600
tcggcccagt ctaagttcct tggaacagga cgtcatagag ggtgagaatc ccgtatgtga    660
ttggtgccgt cccccgtgta aagctctttc gacgagtcga gttgtttggg aatgcagctc    720
aaaatgggtg gtaaatttca tctaaagcta aatattggcc agagaccgat agcgcacaag    780
tagagtgatc gaaagatgaa aagcactttg gaaagagagt taaacagtac gtgaaattgt    840
tgaaagggaa gcgcttgcaa tcagacttgc aggcggttga tcatccgagg ttctccccgg    900
tgcactcgat cgtcttcagg ccagcatcgg tttcagtggt gggataaagg ctgtgagaac    960
gtggctcttc ggagtgttat agctcacggt gcaatgccgc ctactgggac cgaggaccgc   1020
gcttcggcta ggatgctggc gtaatggttg taagcgaccc gtcttgaaac acggaccaag   1080
gagtctaaca tctatgcgag tgtttgggtg tcaaacccat acgcgtaatg aaagtgaacg   1140
gaggtgagac cccattaggg cgcatcatcg accgatcctg atgtcttcgg atggatttga   1200
gtaagagcat agctgttggg acccgaaaga tggtgaacta tgcgtgaata gggtgaagcc   1260
```

| | |
|---|---|
| agaggaaact ctggtggagg ctcgcagcgg ttctgacgtg caaatcgatc gtcaaatttg | 1320 |
| cgtatagggg cgaaagacta atcggttaga cagggtcagt tcacccgtat agggtggtgg | 1380 |
| catctcttgc atcttgtgct gacatgaata tctcagagta accgcaata caaggcagct | 1440 |
| gtttctattc gggacccaaa gcgtagattc gacaccattt ggcgactttg caagcccaag | 1500 |
| atgatctgcg acagtgatgt tcctaatgac gacgaattcg gaggtgatcc aaaggaggct | 1560 |
| gtgaagcgtt cgcatggagg atgtggaaat acgcaacctg aggtgcgcca gcaagctttg | 1620 |
| cagctttggg gaacatggaa gatgccaaaa gatgaagaga atgagggtgg caacactgag | 1680 |
| aagcgacaaa ttactccaga gatggctctc aatgtcttcc ggtccatgtc ttccgatgag | 1740 |
| attcgcgatc tcggtttgag caacgactat gcgcgtcctg actggttgat catcactgtt | 1800 |
| cttccagttc cacctcctcc cgttcgcccc agtatttcta tggatggtac aagcacagga | 1860 |
| atgcgcggag aggatgattt gacctacaag ctaggtgata tcattcgtgc caacggcaat | 1920 |
| gtcaagcagg cacagcaaga agg | 1943 |

<210> SEQ ID NO 3
<211> LENGTH: 1941
<212> TYPE: DNA
<213> ORGANISM: Acephala applanata

<400> SEQUENCE: 3

| | |
|---|---|
| gtgtctacat actcttgttg ctttggcagg ccgtggcctc ccactgtggg ctcagcctgc | 60 |
| atgtgcctgc cagaggacca aactctgaat gttagtgatg tctgagtact atataatagt | 120 |
| taaaacttc aacaacggat ctcttggttc tggcatcgat gaagaacgca gcgaaatgcg | 180 |
| ataagtaatg tgaattgcag aattcagtga atcatcgaat ctttgaacgc acattgcacc | 240 |
| cggtggcatt ccgccgggta tgcctgttcg agcgtcatta taaccactca agcctgtctt | 300 |
| ggtgttgggg attgcgaatc tcgcagccct agagtccagt agcgtcacct gtgggtccta | 360 |
| agcgtagtaa tttctcctcg ctacagagcc tgctcgtgga tagtgtaaat ccagttcggt | 420 |
| ctggtatccc gcggttgacc tcggatcaag tagggatacc cgctgaactt aagcatatca | 480 |
| ataagcggag gaaagaaac caacaggat tactagtaac ggcgagtgaa gcggtaactg | 540 |
| ctcaaatttg aaagctgcca acaggccgcg ttgtaatttg tagaagatgc tttgggtgtc | 600 |
| ggcccagtct aagttccttg gaacaggacg tcatagaggg tgagaatccc gtatgtgatt | 660 |
| ggtgccgtcc cccgtgtaaa gctctttcga cgagtcgagt tgtttgggaa tgcagctcaa | 720 |
| aatgggtggt aaatttcatc taaagctaaa tattggccag agaccgatag cgcacaagta | 780 |
| gagtgatcga agatgaaaa gcactttgga aagagagtta acagtacgt gaaattgttg | 840 |
| aaagggaagc gcttgcaatc agacttgcag gcggttgatc atccgaggtt ctccccggtg | 900 |
| cactcgatcg tcttcaggcc agcatcggtt tcagtggtgg gataaaggct gtgagaacgt | 960 |
| ggctcttcgg agtgttatag ctcacggtgc aatgccgcct actgggaccg aggaccgcgc | 1020 |
| ttcggctagg atgctggcgt aatggttgta agcgacccgt cttgaaacac ggaccaagga | 1080 |
| gtctaacatc tatgcgagtg tttggtgtc aaacccatac gcgtaatgaa agtgaacgga | 1140 |
| ggtgagaccc cattagggcg catcatcgac cgatcctgat gtcttcggat ggatttgagt | 1200 |
| aagagcatag ctgttgggac ccgaaagatg gtgaactatg cgtgaatagg gtgaagccag | 1260 |
| aggaaactct ggtggaggct cgcagcggtt ctgacgtgca atcgatcgt caaatttgcg | 1320 |
| tatagggggcg aaagactaat cggttagaca gggtcagttc acccgtatag gtggtggca | 1380 |

```
tctcttgcat cttgtgctga catgagtatc tcagagtaac ccgcaataca aggcagctgt    1440
ttctattcgg gatccaaagc gtagattcga caccatttgg cgactttgca agcccaagat    1500
gatctgcgac agtgatgttc ctaatgacga cgaattcgga ggtgatccaa aggaggctgt    1560
gaagcgttcc catggaggat gtggaaatac gcaacctgag gtgcgccagc aagccttgca    1620
gctttgggga acatggaaaa tgccaaagga tgaagagaat gagagtggca cactgagaa     1680 gcgacaaatt actccagaga tggctctcaa tgtcttccgg tccatgtctt ccgatgagat    1740
tcgcgatctc ggtttgagca acgactatgc gcgtcctgac tggttgatca tcactgttct    1800
tccagttcca cctcctcctg ttcgccccag tatttctatg gatggtacaa gcacaggaat    1860
gcgcggagag gatgatttga cctacaagct gggtgatatc attcgcgcca acggcaatgt    1920
caagcaggca cagcaagaag g                                              1941

<210> SEQ ID NO 4
<211> LENGTH: 1911
<212> TYPE: DNA
<213> ORGANISM: Acidoradicia panicicola

<400> SEQUENCE: 4
gtgtctatct actcttgttg ctttggcagg ccgtggcctc caccgcgggc tctgcctgcg      60
tgtgcctgcc agaggaccaa actctgaatt ttagtgatgt ctgagtacta tataatagtt    120
aaaactttca acaacggatc tcttggttct ggcatcgatg aagaacgcag cgaaatgcga    180
taagtaatgt gaattgcaga attcagtgaa tcatcgaatc tttgaacgca cattgcgccc    240
ggtggtattc cgccgggcat gcctgttcga gcgtcattat aaccactcaa gcctagcttg    300
gtattggggt tcgcggtccc gcggcccta aaatcagtgg cggtgccggt gggctctaag     360
cgtagtaaat ctcctcgcta tagggtcccc ccggttgccc gcggttgacc tcggatcagg    420
tagggatacc cgctgaactt aagcatatca ataagcggag gaaagaaac caacagggat     480 tactcagtaa cggcgagtga agcggtaaca gctcaaattg aaagctgcca acaggccgcg    540
ttgtaatttg tagaagatgc tttggggta ggcctagtct aagttccttg gaacaggacg     600
tcatagaggg tgagaatccc gtatgtgatt agtgcctgct cccgtgtaaa gctctttcga    660
cgagtcgagt tgtttgggaa tgcagctcaa aatgggtggt atatttcatc taaagctaaa    720
tattggccag agaccgatag cgcacaagta gagtgatcga agatgaaaa gcactttgga     780 aagagagtta aacagtacgt gaaattgttg aaagggaagc gcttgcaacc agacttgcag    840
gcggtcgatc atccgaggtt ctccccggtg cactcgatcg tcttcaggcc agcatcggtt    900
ttggtggcgg gataaaggct ctaggaatgt ggctcttcgg agtgttatag cctagggtgc    960
aatgccgcct accgggaccg aggaccgcgc ttcggctagg atgctggcgt aatggttgta    1020
agcggcccgt cttgaaacac ggaccaagga gtctaacatc tatgcgagtg tttgggtgtc    1080
aaacccatac gcgtaatgaa agtgaacgga ggtgagagcc ctttagggcg catcatcgac    1140
cgatcctgat gtcttcggat ggatttgagt aagagcatag ctgttgggac ccgaaagatg    1200
gtgaactatg cgtgaatagg gtgaagccag aggaaactct ggtggaggct cgcagcggtt    1260
ctgacgtgca aatcgatcgt caaatttgcg tataggggcg aaagactaat cggctagaca    1320
gggtcagttc gcccgaaaag ggtggcggat ctacttgttc tttgtgctga catgagtttc    1380
tcagagtaat ccggcataca aggcagccgt ttcgattcga gacccgaagc gtaagttcga    1440
taccatatgg cgactttgca agcccaagat gatctgcgac agcgatgtcc ctaacgacga    1500
tgaatttggt ggtgatccaa aggaagctgt taaacgttct catggaggtt gtggcaatac    1560
```

```
tcaacccgag gttcgccaac aagctttaca gctctgggga acatggaaga tgcccaagga    1620
tgaagaaaac gagggtgcga ctcaagaaaa gagacagatt actccaaaga tggctctgaa    1680
tgtcttccgc agcatgtcct cggctgagat tcgcgatttg ggcttgagca atgactatgc    1740
acgccctgac tggcttatca ttactgtcct tcctgttcct cccccgcctg ttcgaccgag    1800
tatctccatg gatggtacaa gcacaggaat gcgcggagag gatgatttga catacaagct    1860
tggtgatatt attcgtgcaa acggaaacgt taagcaagcc caacaagagg g              1911
```

<210> SEQ ID NO 5
<211> LENGTH: 1857
<212> TYPE: DNA
<213> ORGANISM: Acidoradicia panicicola

<400> SEQUENCE: 5

```
gtgtctatct actcttgttg ctttggcagg ccgtggcctc caccgcgggc tctgcctgcg      60
tgtgcctgcc agaggaccaa actctgaatt ttagtgatgt ctgagtacta tataatagtt     120
aaaactttca acaacggatc tcttggttct ggcatcgatg aagaacgcag cgaaatgcga     180
taagtaatgt gaattgcaga attcagtgaa tcatcgaatc tttgaacgca cattgcgccc     240
ggtggtattc cgccgggcat gcctgttcga gcgtcattat aaccactcaa gcctagcttg     300
gtattggggt tcgcggtccc gcggccccta aaatcagtgg cggtgccggt gggctctaag     360
cgtagtaaat ctcctcgcta tagggtcccc ccggttgccc gcggttgacc tcggatcagg     420
tagggatacc cgctgaactt aagcatatca ataagcggag gaaagaaaac caacagggat     480
tacctcagta acggcgagtg aagcggtaac agctcaaatt tgaaagctgc caacaggccg     540
cgttgtaatt tgtagaagat gctttggggg tcggcctagt ctaagttcct tggaacagga     600
cgtcatagag ggtgagaatc ccgtatgtga ttagtgccgg ctcccgtgta aagctctttc     660
gacgagtcga gttgtttggg aatgcagctc aaaatgggtg gtatatttca tctaaagcta     720
aatattggcc agagaccgat agcgcacaag tagagtgatc gaaagatgaa aagcactttg     780
gaaagagagt taaacagtac gtgaaattgt tgaaagggaa gcgcttgcaa ccagacttgc     840
aggcggtcga tcatccgagg ttctccccgg tgcactcgat cgtcttcagg ccagcatcgg     900
ttttggtggc gggataaagg ctctaggaat gtggctcttc ggagtgttat agcctagggt     960
gcaatgccgc ctaccgggac cgaggaccgc gcttcggcta ggatgctggc gtaatggttg    1020
taagcggccc gtcttgaaac acggaccaag gagtctaaca tctatgcgag tgtttggtg     1080 tcaaacccat acgcgtaatg aaagtgaacg gaggtgagag ccctttaggg cgcatcatcg    1140
accgatcctg atgtcttcgg atggatttga gtaagagcat agctgttggg acccgaaaga    1200
tggtgaacta tgcgtgaata gggtgaagcc agaggaaact ctggtggagg ctcgcagcgg    1260
ttctgacgtg caaatcgatc gtcaaatttg cgtataggg  cgaaagacta atcggacatg    1320
agtttctcag agcaatccgg catacaaggc agccgtttca attcgagacc cgaagcgtag    1380
gttcgatacg atatggcgac tttgcaagcc caagatgatc tgcgacagcg atgtccctaa    1440
tgatgatgaa tttggtggtg atccaaaaga agctgttaaa cgttctcatg gaggttgtgg    1500
caatactcaa cccgaggttc gccagcaagc tttacagctc tggggaacat ggaagatgcc    1560
caaggatgaa gaaaacgagg gtgcgactca agaaaagaga cagattactc cagagatggc    1620
tctgaacgtc ttccgcagca gtcctcggc tgagattcgc gatttgggct tgagcaatga    1680
ctatgcacgc cctgactggc ttatcattac tgtccttccc gttcctcccc cacctgttcg    1740
```

| accaagtatt tccatggatg gtacaagcac aggaatgcgc ggagaggatg atttgacata | 1800 |
| caagcttggt gatattatcc gtgcaaatgg tttcattaag caagcccaac aagaggg | 1857 |

<210> SEQ ID NO 6
<211> LENGTH: 1669
<212> TYPE: DNA
<213> ORGANISM: Acidoradicia panicicola

<400> SEQUENCE: 6

| gtgtctatct actcttgttg cttttggcagg ccgtggcctc accgcgggc tctgcctgcg | 60 |
| tgtgcctgcc agaggaccaa actctgaatt ttagtgatgt ctgagtacta tataatagtt | 120 |
| aaaactttca acaacggatc tcttggttct ggcatcgatg aagaacgcag cgaaatgcga | 180 |
| taagtaatgt gaattgcaga attcagtgaa tcatcgaatc tttgaacgca cattgcgccc | 240 |
| ggtggtattc cgccgggcat gcctgttcga gcgtcattat aaccactcaa gcctggcttg | 300 |
| gtattgggac tcgcggttcc gcggcccta aaatcagtgg cggtgccggt gggctctaag | 360 |
| cgtagtaaat ctcctcgcta tagggtcct ccggttgcct gctgtaaagc tctttcgacg | 420 |
| agtcgagttg tttgggaatg cagctcaaaa tgggtggtat atttcatcta aagctaaata | 480 |
| ttggccagag accgatagcg cacaagtaga gtgatcgaaa gatgaaaagc actttggaaa | 540 |
| gagagttaaa cagtacgtga aattgttgaa agggaagcgc ttgcaaccag acttgcaggc | 600 |
| ggtcgatcat ccgaggttct ccccggtgca ctcgatcgtc ttcaggccag catcggtttt | 660 |
| ggtggcggga taaaggctct aggaatgtgg ctcttcggag tgttatagcc tagggtgcaa | 720 |
| tgccgcctac cgggaccgag gaccgcgctt cggctaggat gctggcgtaa tggttgtaag | 780 |
| cggcccgtct tgaaacacgg accaaggagt ctaacatcta tgcgagtgtt tgggtgtcaa | 840 |
| acccatacgc gtaatgaaag tgaacggagg tgagagccct ttagggcgca tcatcgaccg | 900 |
| atcctgatgt cttcggatgg atttgagtaa gagcatagct gttgggaccc gaaagatggt | 960 |
| gaactatgcg tgaatagggt gaagccagag gaaactctgg tggaggctcg cagcggttct | 1020 |
| gacgtgcaaa tcgatcgtca aatttgcgta taggggcgaa agactaatcg gctagacagg | 1080 |
| gtcagttcgc ccgaaaaggg tggcggatct acttgttctt tgtgctgaca tgagtttctc | 1140 |
| agagcaatcc ggcatacaag gcagccgttt caattcgaga cccgaagcgt aggttcgata | 1200 |
| cgatatggcg actttgcaag cccaagatga tctgcgacag cgatgtccct aatgatgatg | 1260 |
| aatttggtgg tgatccaaag gaagctgtta acgttctca tggaggttgt ggcaatactc | 1320 |
| aacccgaggt tcgccagcaa gctttacagc tctggggaac atggaagatg cccaaggatg | 1380 |
| aagaaaacga gggtgcgact caagaaaaga gacagattac tccagagatg gctttgaatg | 1440 |
| tcttccgcag catgtcctcg gctgagattc gcgatttggg cttgagcaat gactatgcac | 1500 |
| gccctgattg gcttatcatt actgtccttc ccgttcctcc cccacctgtt cgaccaagta | 1560 |
| tttccatgga tggtacaagc acaggaatgc gcggagagga tgatttgaca tacaagcttg | 1620 |
| gtgatattat ccgtgcaaac ggcaacgtta agcaagccca acaagaggg | 1669 |

<210> SEQ ID NO 7
<211> LENGTH: 1448
<212> TYPE: DNA
<213> ORGANISM: Acidoradicia taeda

<400> SEQUENCE: 7

| gtgtctattt actcttgttg cttttggcagg ccgtggcctc accgtgggc tctgtctacg | 60 |
| cgtgtctgcc agaggaccaa actctgaatt ttagtgatgt ctgagtacta tacaatagtt | 120 |

```
aaaactttca acaacggatc tcttggttct ggcatcgatg aagaacgcag cgaaatgcga      180
taagtaatgt gaattgcaga attcagtgaa tcatcgaatc tttgaacgca cattgcgccc      240
ggtggtattc cgccgggcat gcctgttcga gcgtcattat aaccactcaa gcctggcttg      300
gtattggggt acgcggcttc gcggctccta aaatcagtgg cggtgccggt gggctctaag      360
cgtagtaaat ctcctcgcta tagggttcct ctggttgctt gcggtgcact cgatcgtctt      420
caggccagca tcggtttcgg tggcgggata aaggctctag gaatgtggct cttcggagtg      480
ttatagccta gggtgcaatg ccgcctaccg ggaccgagga ccgcgcttcg gctaggatgc      540
tggcgtaatg gttgtaagcg gcccgtcttg aaacacggac caaggagtct aacatctatg      600
cgagtgtttg ggtgtcaaac ccatacgcgt aatgaaagtg aacggaggtg agagcccttt      660
agggcgcatc atcgaccgat cctgatgtct tcggatggat tgagtaaga gcatagctgt       720 tgggacccga aagatggtga actatgcgtg aatagggtga agccagagga aactctggtg      780
gaggctcgca gcggttctga cgtgcaaatc gatcgtcaaa tttgcgtata ggggcgaaag      840
actaatcggc tagacagggt cagttcgccc gaatagggtg gcagatctac ttgttctttg      900
tgctgacatg agtatctcag agtaatccgg cgtacaaggc agctgtttcg attcgggacc      960
cgaagcgtag gttcgatacg atatggcgac tttgcaagcc caagatgatc tgcgacagcg     1020
atgtccctaa cgacgatgaa tttggtggtg atccaaagga agctgtcaag cgttctcatg     1080
gaggttgtgg taatactcag cccgaggttc gtcagcaggc tctacagctc tggggtacat     1140
ggaagatgcc aaaggatgaa gaaatgagg ggtcaagtca agaaaagaga caaatcactc      1200
cagagatggc tttaaatgtc ttccgaagca tgtcctcggc tgagattcgc gacctgggcc     1260
tgagcaacga ctacgctcgt cccgactggc tcatcattac agtccttcct gttcctcctc     1320
cgcccgttcg ccctagtatt tctatggatg gcacaagcac gggaatgcgt ggagaagatg     1380
atttgaccta caagcttggt gatataattc gtgcctacgg caacgttatg caaagcacaa     1440
caagaatg                                                             1448

<210> SEQ ID NO 8
<211> LENGTH: 1493
<212> TYPE: DNA
<213> ORGANISM: Acidoradicia taeda

<400> SEQUENCE: 8
gtgtctattt actcttgttg cttgggcagg ccgtggcctc caccgtgggc tctgtctacg       60
cgtgtctgcc agaggaccaa actctgaatt ttagtgatgt ctgagtacta tacaatagtt      120
aaaactttca acaacggatc tcttggttct ggcatcgatg aagaacgcag cgaaatgcga      180
taagtaatgt gaattgcaga attcagtgaa tcatcgaatc tttgaacgca cattgcgccc      240
ggtggtattc cgccgggcat gcctgttcga gcgtcattat aaccactcaa gcctggcttg      300
gtattggggt acgcggcttc gcggctccta aaatcagtgg cggtgccggt gggctctaag      360
cgtagtaaat ctcctcgcta tagggttcct ctggttgctt gcgcttgcaa ccagacttgc      420
aggcggtcga tcatccgagg ttctccccgg tgcactcgat cgtcttcagg ccagcatcgg      480
tttcggtggc gggataaagg ctctaggaat gtggctcttc ggagtgttat agcctagggt      540
gcaatgccgc ctaccgggac cgaggaccgc gcttcggcta ggatgctggc gtaatggttg      600
taagcggccc gtcttgaaac acggaccaag gagtctaaca tctatgcgag tgtttgggtg      660
tcaaacccat acgcgtaatg aaagtgaacg gaggtgagag ccctttaggg cgcatcatcg      720
```

```
accgatcctg atgtcttcgg atggatttga gtaagagcat agctgttggg acccgaaaga      780
tggtgaacta tgcgtgaata gggtgaagcc agaggaaact ctggtggagg ctcgcagcgg      840
ttctgacgtg caaatcgatc gtcaaatttg cgtataggg  cgaaagacta atcggctaga      900
cagggtcagt tcgcccgaat agggtggcag atctacttgt tctttgtgct gacatgagta      960
tctcagagta atccggcgta caaggcagct gtttcgattc gggacccgaa gcgtaggttc     1020
gatacgatat ggcgactttg caagcccaag atgatctgcg acagcgatgt ccctaacgac     1080
gatgaatttg gtggtgatcc aaaggaagct gtcaagcgtt ctcatggagg ttgtggtaat     1140
actcagcccg aggttcgtca gcaggctcta cagctctggg gtacatggaa gatgccaaag     1200
gatgaagaaa atgaggggtc aagtcaagaa aagagacaaa tcactccaga gatggctcta     1260
aatgtcttcc gaagcatgtc ctcggctgag attcgcgacc tgggcctgag caacgactac     1320
gctcgtcccg actggctcat cattacagtc cttcctgttc ctcctccgcc cgttcgccct     1380
agtatttcta tggatggcac aagcacggga atgcgtggag aagatgattt gacctacaag     1440
cttggtgata taattcgtgc aaacggcaac gttaagcaag cacaacaaga agg           1493

<210> SEQ ID NO 9
<211> LENGTH: 1493
<212> TYPE: DNA
<213> ORGANISM: Acidoradicia taeda

<400> SEQUENCE: 9
gtgtctattt actcttgttg ctttggcagg ccgtggcctc caccgtgggc tctgtctacg       60
cgtgtctgcc agaggaccaa actctgaatt ttagtgatgt ctgagtacta tacaatagtt      120
aaaactttca caacggatc  tcttggttct ggcatcgatg aagaacgcag cgaaatgcga      180
taagtaatgt gaattgcaga attcagtgaa tcatcgaatc tttgaacgca cattgcgccc      240
ggtggtattc cgccgggcat gcctgttcga gcgtcattat aaccactcaa gcctggcttg      300
gtattggggt acgcggcttc gcggctccta aaatcagtgg cggtgccggt gggctctaag      360
cgtagtaaat ctcctcgcta tagggttcct ctggttgctt gcgcttgcaa ccagacttgc      420
aggcggtcga tcatccgagg ttctccccgg tgcactcgat cgtcttcagg ccagcatcgg      480
tttcggtggc gggataaagg ctctaggaat gtggctcttc ggagtgttat agcctagggt      540
gcaatgccgc ctaccgggac cgaggaccgc gcttcggcta ggatgctggc gtaatggttg      600
taagcggccc gtcttgaaac acggaccaag gagtctaaca tctatgcgag tgtttgggtg      660
tcaaacccat acgcgtaatg aaagtgaacg gaggtgagag ccctttaggg cgcatcatcg      720
accgatcctg atgtcttcgg atggatttga gtaagagcat agctgttggg acccgaaaga      780
tggtgaacta tgcgtgaata gggtgaagcc agaggaaact ctggtggagg ctcgcagcgg      840
ttctgacgtg caaatcgatc gtcaaatttg cgtataggg  cgaaagacta atcggctaga      900
cagggtcagt tcgcccgaat agggtggcag atctacttgt tctttgtgct gacatgagta      960
tctcagagta atccggcgta caaggcagct gtttcgattc gggacccgaa gcgtaggttc     1020
gatacgatat ggcgactttg caagcccaag atgatctgcg acagcgatgt ccctaacgac     1080
gatgaatttg gtggtgatcc aaaggaagct gtcaagcgtt ctcatggagg ttgtggtaat     1140
actcagcccg aggttcgtca gcaggctcta cagctctggg gtacatggaa gatgccaaag     1200
gatgaagaaa atgaggggtc aagtcaagaa aagagacaaa tcactccaga gatggctcta     1260
aatgtcttcc gaagcatgtc ctcggctgag attcgcgacc tgggcctgag caacgactac     1320
gctcgtcccg actggctcat cattacagtc cttcctgttc ctcctccgcc cgttcgccct     1380
```

```
agtatttcta tggatggcac aagcacggga atgcgtggag aagatgattt gacctacaag    1440
cttggtgata taattcgtgc aaacggcaac gttaagcaag cacaacaaga agg            1493

<210> SEQ ID NO 10
<211> LENGTH: 2027
<212> TYPE: DNA
<213> ORGANISM: Cudoniella clavus
<220> FEATURE:
<221> NAME/KEY: misc_feature
<222> LOCATION: (573)..(573)
<223> OTHER INFORMATION: n is a, c, g, or t
<220> FEATURE:
<221> NAME/KEY: misc_feature
<222> LOCATION: (1831)..(1831)
<223> OTHER INFORMATION: n is a, c, g, or t

<400> SEQUENCE: 10
aaaagtcgta acaaggtttc cgtaggtgaa cctgcggaag gatcattaca gtgttccctg      60
ccctcacggg tagaaacgcc acccttgtat atattatctt gttgctttgg cgggccgcct    120
ttaggcactg gcttcggctg gctcgcgccc gccagagaac cccaaactct aaatgttagt    180
gtcgtctgag tactatctaa tagttaaaac tttcaacaac ggatctcttg gttctggcat    240
cgatgaagaa cgcagcgaaa tgcgataagt aatgtgaatt gcagaattca gtgaatcatc    300
gaatctttga acgcacattg cgccccttgg tattccgggg gcatgcctg ttcgagcgtc     360 atttaaacca atccagcatg ctgggtcttg gccttcgcc tctgggcggg cctcaaaatt     420
agtggcggtg ccacctggct ctacgcgtag taattcttct cgcgatggag tcccaggtgg    480
aagcttgcca acaaccccaa attctttaa aggttgacct cggatcaggt agggataccc      540
gcctaagcat atcaataagc ggaggaaaag aanccaacag ggattacctc agtaacggcg    600
agtgaagcgg taacagctca aatttgaaat ctggctcttt cagggtccga gttgtaattt    660
gtagaagatg cttcgggtgt ggctccggtc taagttcctt ggaacaggac gtcatagagg    720
gtgagaatcc cgtatgtgac tggttgcctt cgcccatgtg aagctctttc gacgagtcga    780
gttgtttggg aatgcagctc taaatgggtg gtaaatttca tctaaagcta aatattggcc    840
agagaccgat agcgcacaag tagagtgatc gaaagatgaa aagcactttg gaaagagagt    900
taaacagtac gtgaaattgt tgaaagggaa gcgcttgcaa ccagacttgc acgtcgtcga    960
tcatcctcag ttctctgggg tgcactcggc ggtgttcagg ccagcatcgg tttcggtggt   1020
gggataaagg ccttgggaat gtggctcctc tcggggagtg ttatagccct cggtgcaatg   1080
ccgcctactg ggaccgagga ccgcgcttcg gctaggatgc tggcgtaatg gttgtaagcg   1140
acccgtcttg aaacacggac caaggagtct aacatctatg cgagtgtttg ggtgttaaac   1200
ccatacgcgt aatgaaagtg aacggagtg agaacccttt agggtgcatc atcgaccgat    1260
cctgatgtct tcggatggat ttgagtaaga gcatagctgt tgggacccga aagatggtga   1320
actatgccta aatagggtga agccagagga aactctggtg gaggctcgca gcggttctga   1380
cgtgcaaatc gatcgtcaaa tttgggtata ggggcgaaag actaatcgac tagacagggt   1440
cagttggccc gcatagcgtg gcatgtcttt tgtgcctttg tgctaacaga atgatttcag   1500
agcaatccag cgtacaaggc agctgtttct atccgagatc caaagcgtag atttgataca   1560
atatggcgac tgtgcaagcc gaagatgatt tgcgagggtg atgtgcaggc gaatgaggaa   1620
gaatttgatc ccaaccaaaa agaaccgaag ccgtcgcacg gagggtgtgg taattctcag   1680
cctgaagtgc gtcagactgc tttgcaacta tggggaacat ggaaagtgcc taaggacgaa   1740
```

```
gataacgaga gtcagtcgcc ggaaaagagg cagattactc ccgaaatggc tctggctgtc    1800
ttccgaagca tttccacgga agaaatcttc naccttggcc tgagtaatga ttatgcgcgt    1860
cccgaatgga tgatcataac ggttctccca gttcctccac cacctgttcg acccagtatt    1920
tcaatggatg gcactggtca gggcatgcgc ggagaggacg atttgacata taagttggga    1980
gatatcatcc gggcaaacgg caatgtgcgg caagctcagc aggaagg                  2027
```

<210> SEQ ID NO 11
<211> LENGTH: 1818
<212> TYPE: DNA
<213> ORGANISM: Dermea acerina
<220> FEATURE:
<221> NAME/KEY: misc_feature
<222> LOCATION: (446)..(446)
<223> OTHER INFORMATION: n is a, c, g, or t

<400> SEQUENCE: 11

```
gtgtcgttat accttcgttg ctttggtggg ccgctgggct tcggcctggc tcctggctcc      60
ggctagggag tgcccgccag aggaccttaa aacctgaagt tagtgtcgtc tgagtactat     120
acaatagtta aaactttcaa caacggatct cttggttctg gcatcgatga agaacgcagc     180
gaaatgcgat aagtaatgtg aattgcagaa ttcagtgaat catcgaatct ttgaacgcac     240
attgcgcccc ttggtattcc ggggggcatg cctgttcgag cgtcattaca accctcaagc     300
tctgcttggt attgggcgtc accgggttcg gtgtgcctta aaatcagtgg cggcgccgtc     360
tggctctaag cgtagtacat actctcgcta tggacgcctg cggatgcttt gcgaaatctg     420
ggtcttttag gctccgagtt gtaatntgta gaagatgctt cgggtgcggc tccggtctaa     480
gttccttgga acaggacgtc atagagggtg agaatcccgt atgtgatcgg gggcttgcgc     540
ccatgtgaag ctctttcgac gagtcgagtt gtttgggaat gcagctcaaa atgggtggta     600
tatttcatct aaagctaaat attggccaga gaccgatagc gcacaagtag agtgatcgaa     660
agatgaaaag cactttggaa agagagttaa acagtacgtg aaattgttga agggaagcg     720 cttgcaacca gacttgggcg gggttgatca tctagggttc tccctagtgc actcgacctc     780
gcacaggcca gcatcggttc cggtggttgg ataaaggcct tgggaatgta gcttctttcg     840
gggagtgtta tagccctcgg tgcaatgcag cctactggga ccgaggaccg cgcttcggct     900
aggatgctgg cgtaatggtt gtaagcgacc cgtcttgaaa cacggaccaa ggagtctaac     960
atctatgcga gtgtttgggt gtcaaaccca tacgcgtaat gaaagtgaac ggaggtgaga    1020
acccttaagg gtgcatcatc gaccgatcct gatgtcttcg gatggatttg agtaagagca    1080
tagctgttgg gacccgaaag atggtgaact atgcctgaat agggtgaagc cagaggaaac    1140
tctggtggag gctcgcagcg gttctgacgt gcaaatcgat cgtcaaattt gggtataggg    1200
gcgaaagact aatcggctag acagggtcag ttctcccacg tagcgtgggg agcatgattg    1260
tttctgtgtg ctaacgtcaa tatctcagag taatccagcg tacaaagcag ccgtttcgat    1320
tcgagacccg aagcgtaggt tcgatacgat ctggcgactt tgcaagccca agatgatctg    1380
tgatagcgat ttgactgccg ccgatgatga tttcaatgca gacccgaagg aagccgcaaa    1440
gcgctcgcac ggtggatgtg gaaatactca gcctgaggtg cgccagtcgg ccttgcagct    1500
gtggggtaca tggaaggttc caaaggatga agacaatgat ggtgctactg ccgaaaagaa    1560
gcagatcact gcagagatgg ccctgaatgt cttccgaagc atttccactt ctgagatcca    1620
agaccttggc ttgagtactg actatgcgcg acctgaatgg atgatcatta cggttcttcc    1680
agttcctcct ccacctgttc gaccgagtat ttcgatggac ggcactgggc aaggcatgcg    1740
```

| aggagaggat gatttgacat acaagcttgg cgatatcatt cgtgcgaatg caacgttcg | 1800 |
| acaggcccag caagaagg | 1818 |

<210> SEQ ID NO 12
<211> LENGTH: 1947
<212> TYPE: DNA
<213> ORGANISM: Hyaloscypha aureliella

<400> SEQUENCE: 12

| gtgcctggtc taagatatag tcggtcccgg cccgaaaggg ccggggaaca gcgtccgtag | 60 |
| gtgaacctgc ggaaggatca ttacagagtt catgccctca cggtagatc tcccacccctt | 120 |
| gaataccttta cctttgtctg ctttggcggg ccacgtccgc gtgccggctc cggctggttg | 180 |
| cgcccgccag aggacccaaa ctcttttgtt tagtgatgtc tgagtactat ataatagtta | 240 |
| aaactttcaa caacggatct cttggttctg catcgatga agaacgcagc gaaatgcgat | 300 |
| aagtaatgtg aattgcagaa ttcagtgaat catcgaatct ttgaacgcac attgcgcccc | 360 |
| ttggtattcc gaggggcatg cctgttcgag cgtcattatg accactcaag cctggcttgg | 420 |
| tgttggggtc cgcggtcccg cggcccttaa aatcagtggc ggcgccatct ggctctcagc | 480 |
| gtagtaatac tcctcgctac agggtcccac ggcgagtgaa gcggcaacag ctcaaatttg | 540 |
| aaatctggct cctgcggggc ccgagttgta atttgtagaa gatgctttga gcgtggctcc | 600 |
| ggtctaagtt ccttggaaca ggacgtcata gagggtgaga atcccgtatg tgactgggtg | 660 |
| cctccgttcg tgtaaagctc tttcgacgag tcgagttgtt tgggaatgca gctcaaaatg | 720 |
| ggtggtaaat ttcatctaaa gctaaatatt ggccagagac cgatagcgca caagtagagt | 780 |
| gatcgaaaga tgaaaagcac tttggaaaga gagttaaaca gtacgtgaaa ttgttgaaag | 840 |
| ggaagcgctt gcaaccagac ttgcccgctg ctgatcatcc gaggttctcc ccggtgcact | 900 |
| cggcagcgat caggccagca tcggttctgg tgggcggata aaggccttgg gaatgtagct | 960 |
| tccttcgggg agtgttatag ccctcggtgc aatgcgccct accgggaccg aggaccgcgc | 1020 |
| ttcggctagg atgctggcgt aatggttgta agcgacccgt cttgaaacac ggaccaagga | 1080 |
| gtctaacatc tatgcgagtg tttgggtgtt aaacccatac gcgtaatgaa agtgaacgga | 1140 |
| ggtgagaacc cttaagggtg catcatcgac cgatcctgat gtcttcggat ggatttgagt | 1200 |
| aagagcatag ctgttgggac ccgaaagatg gtgaactatg cctgaatagg gtgaagccag | 1260 |
| aggaaactct ggtggaggct cgcagcggtt ctgacgtgca aatcgatcgt caaatttggg | 1320 |
| tataggggcg aaagactaat cgacttgaca gagtcagtgt gcctgaactt gagggccgag | 1380 |
| tttcttgtgt gcctttatgc taacttcatg attgcagaac aatccggcgt acaaagctgc | 1440 |
| tgtgagcatt cgagacccga aacgtcggtt cgatgcgata tggcgacttt gcaaaccgaa | 1500 |
| attgatctgc gacagtgatt tgagtgcagg ggacgagggc ttcgacgctg acccaaagga | 1560 |
| acttgcgaaa cgctcgcatg gaggatgtgg aaataaacaa ccagaagtgc gccagagcgc | 1620 |
| ccttcagctc accggcactt ttaagccttc gaaggaagaa ctcagcgagg gcatgcagcc | 1680 |
| agaaaagaag ttaatcaccc cagaggcagc tctgcacatc ttccgaagca tttcctccga | 1740 |
| cgagattcgc gacttaggcc tgagcaatga ttatgcgcgc ccggaatgga tgatcatcac | 1800 |
| agtccttccc gtgcctcctc ctcctgttcg gcccagtatt tctatggatg gcactggtca | 1860 |
| aggtatgcga ggagaggatg atttgacata caaacttggt gacatcatcc gtgcgaatgg | 1920 |
| aaacgttcga caggcgcatc aagaggg | 1947 |

<210> SEQ ID NO 13
<211> LENGTH: 1857
<212> TYPE: DNA
<213> ORGANISM: Lachnum virgineum

<400> SEQUENCE: 13

| | | | | | |
|---|---|---|---|---|---|
| gtatcattat | agaatgttgc | tttggcgggc | tgcgtgccta | gcacgcctcg | attcgcgtcg | 60 |
| agcgcgcccg | ccagaggacc | cctaaactst | gaatgttagt | gtcgtctgag | tactattaaa | 120 |
| tagttaaaac | tttcaacaac | ggatctcttg | gttctggcat | cgatgaagaa | cgcagcgaaa | 180 |
| tgcgataagt | aatgtgaatt | gcagaattca | gtgaatcatc | gaatctttga | acgcacattg | 240 |
| cgccccttgg | tattccgggg | ggcatgcctg | ttcgagcgtc | atttatacca | atctarcctg | 300 |
| gctaggtgtt | gggcctcgcc | agttggcggg | ccttaaaact | agtggcggtg | ctcttcagct | 360 |
| ctacgcgtag | taattttctc | gctataggct | ctggggagat | gcttgcccac | agggattacc | 420 |
| tcagtaacgg | cgagtgaagc | ggtaacagct | caaatttgaa | atctggctct | tttagggtcc | 480 |
| gagttgtaat | ttgtagaaga | tgctttgggt | gtggccctgg | tctaagttcc | ttggaacagg | 540 |
| acgtcataga | gggtgagaat | cccgtatgtg | actaggtgcc | ttcgcccgtg | taaagctctt | 600 |
| tcgacgagtc | gagttgtttg | ggaatgcagc | tcaaaatggg | tggtaaattt | catctaaagc | 660 |
| taaatattgg | ccagagaccg | atagcgcaca | agtagagtga | tcgaaagatg | aaaagcactt | 720 |
| tggaaagaga | gttaaacagt | acgtgaaatt | gttgaaaggg | aagcgcttgc | aaccagactt | 780 |
| agttgctgcc | gatcatccag | ggttctccct | ggtgcactcg | gtagtatcta | ggccagcatc | 840 |
| ggtttgggtg | gtgggataaa | ggccttggga | atgtagcttc | tttcggggag | tgttatagcc | 900 |
| ctcggtgcaa | tgccgcctac | ccggaccgag | gaccgcgctt | cggctaggat | gctggcgtaa | 960 |
| tggttgtaag | ccacccgtct | tgaaacacag | accaaggagt | ctaacatcta | tgcgagtatt | 1020 |
| tgggtgttaa | acccatatgc | gtaatgaaag | tgaacggagg | tgagaaccct | taagggtgca | 1080 |
| tcatcgaccg | atcctgatgt | cttcggatgg | atttgagtaa | gagcatagct | gttgggaccc | 1140 |
| gaaagatggt | gaactatgcc | taaatagggt | gaagccagag | gaaactctgg | tggaggctcg | 1200 |
| cagcggttct | gacgtgcaaa | tcgatcgtca | aatttgggta | tagggggcgaa | agactaatcg | 1260 |
| gcttgacagg | gtcagttcac | cgtaaaaggt | gttggcttcg | cttgttcttt | ttgctgacag | 1320 |
| aatatctcag | ggtaatcccc | agtacaaggc | agctgtttct | attcgtgatc | caaagcgtag | 1380 |
| attcgataca | atctggcgac | tttgcaagcc | caagatgatc | tgcgatagcg | atgtccctaa | 1440 |
| tgaagatgaa | ttcggtggtg | atccaaagga | agctgtgaag | cgttcgcatg | gaggatgtgg | 1500 |
| aaatacacaa | cctgaggtcc | gccaacaggc | attgcagctc | tggggaacat | ggaagatgcc | 1560 |
| aaaggatgag | gagaacgagg | gtggcaactc | ggagaagaga | caaattacac | cagagatggc | 1620 |
| tctcaatgtc | ttcagatcca | tgtcttctga | agaaattcgc | gacctcggtc | tcagcaacga | 1680 |
| ttatgcacgt | cctgactggt | tgattattac | agttcttcca | gttccgcctc | ctcctgttcg | 1740 |
| acccagtatt | tccgtggacg | gcacgagcac | aggtatgcgc | ggagaggatg | atttgacata | 1800 |
| caagcttggt | gatatcattc | gtgccaacgg | caatgtgaag | caggctcaac | aagaagg | 1857 |

<210> SEQ ID NO 14
<211> LENGTH: 1628
<212> TYPE: DNA
<213> ORGANISM: Loramyces macrosporus
<220> FEATURE:
<221> NAME/KEY: misc_feature
<222> LOCATION: (476)..(476)
<223> OTHER INFORMATION: n is a, c, g, or t
<220> FEATURE:
<221> NAME/KEY: misc_feature
<222> LOCATION: (597)..(598)
<223> OTHER INFORMATION: n is a, c, g, or t

<400> SEQUENCE: 14

```
gtgtctatat actcttgttg ctttggcagg ccgtggtctc gaccctgtgg gctttgcctg      60
catgtgcctg ccagaggacc aaactctgaa ttttagtgat gtctgagtac tatataatag     120
ttaaaacttt caacaacgga tctcttggtt ctggcatcga tgaagaacgc agcgaaatgc     180
gataagtaat gtgaattgca gaattcagtg aatcatcgaa tctttgaacg cacattgcgc     240
ccggtggtat tccgccgggc atgcctgttc gagcgtctct atcaacctac acgctccgcg     300
tggaattggg gcctgcggtc acctgcagcc ctagaaccca acagcgatac cgagtggtcc     360
tcagcgtagt acataccccg ctacaggcct cctctggtgt tctgctggtc tatatcatct     420
aaagctacat attggccaga ggccgatagc gcacaagtag agtgatcgaa agatgnaaag     480
cactttggaa agagagttaa acagtacgtg aaattgttga aagggaagcg cttgcaatca     540
gacttgcagg cggttgatca tccggggttt tccccggtgc actcgatcgt cttcagnnca     600
gcatcagttc tcgtggtggg ataaaggctg tgagaatgtg gctcttcgga gtgttatagc     660
tcacggtgca atgctgccta cggggactga ggaccgcgct tcggctagga tgctggcgta     720
atggttgtaa gcgacccgtc ttgaaacacg gaccaaggag tctaacatct atgcgagtgt     780
ttgggtgtca aacccatacg cgtaatgaaa gtgaacggag gtgagaaccc tttagggcgc     840
atcatcgacc gatcctgatg tcttcggatg gatttgagta agagcatagc tgttgggacc     900
cgaaagatgg tgaactatgc gtgaataggg tgaagccaga ggaaactctg gtggaggctc     960
gcagcggttc tgacgtgcaa atcgatcgtc aaatttgcgt ataggggcga aagactaatc    1020
gccttgacag agttagtcag cccagaaggc gtgacgtttc ttgttcctca tttatgctaa    1080
cgtaatggcc atcagaccaa tcctcagtat aaggcggctc tttctattcg tgatccaaag    1140
cgtagattcg atacgatctg gcggctctgc aaacctaaga tgatttgcga gattgatagc    1200
acaccggaag atctagattt cgaaggaaag ccaacggatg ccgggaaagt ccgaagtcat    1260
ggtggatgcg gaaatattca accggaagtt cgccagaccg cgcttcaact ttggggcact    1320
tggaaggtac caaaggatga ggataatgag gcacaacaac ctgagaagaa gcagatctca    1380
cctgagatgg cattgcaggt cttccgtagc atctcaaatg aggagattca cgatcttggt    1440
ctgaacaatg attatgctcg gccagagtgg atgattatca ccgttcttcc cgtacctcca    1500
ccacctgtcc gaccaagtat ttcgatggac ggcactggac agggcatgcg aggagaggat    1560
gatttgactt ataagcttgg cgatatcatc cgcgcgaatg gtaacgtccg tcaagcacag    1620
caggaagg                                                              1628
```

<210> SEQ ID NO 15
<211> LENGTH: 1831
<212> TYPE: DNA
<213> ORGANISM: Mollisia cinerea

<400> SEQUENCE: 15

```
gtgtctacat actcttgttg ctttggcagg ccgtggtctc cactgtgggc tctgcctaca      60
tgtgcctgcc agaggaccaa aatctgaatt ttagtgatgt ctgagtacta tataatagtt     120
aaaactttca acaacggatc tcttggttct ggcatcgatg aagaacgcag cgaaatgcga     180
taagtaatgt gaattgcaga attcagtgaa tcatcgaatc tttgaacgca cattgcgccc     240
```

-continued

```
tgtggtattc cgcagggcat gcctgttcga gcgtcattat aaccactcaa gcctggcttg      300
gtattggagt ttgcggttcc gcagctccta aaatcagtgg cggtgccggt gtggctctac      360
gcgtagtaat tcttctcgcg atggagttcc cctggttgct tgctaacggc gagtgaagcg      420
gtaacagctc aaatttgaaa gctaccaaca ggtcgcattg taatttgtag aagatgcttt      480
gggtgttgac ctagtctaag ttccttggaa caggacgtca tagagggtga gaatcccgta      540
tgtgattagt gtcagccccc gtgtaaagct ctttcgacga gtcgagttgt ttgggaatgc      600
agctcaaaat gggtggtaaa tttcatctaa agctaaatat tggccagaga ccgatagcgc      660
acaagtagag tgatcgaaag atgaaaagca ctttggaaag agagttaaac agtacgtgaa      720
attgttgaaa gggaagcgct tgcaatcaga cttgcaggca gtcgatcatc cgaggttctc      780
cccggtgcac tcgattgtct tcaggccagc atcggtttcg gtggtgggat aaaggctgtg      840
ggaatgtggc tcttcggagt gttatagccc acggtgcaat gccgcctacc gggaccgagg      900
accgcgcttc ggctaggatg ctggcgtaat ggttgtaagc gacccgtctt gaaacacgga      960
ccaaggagtc taacatctat gcgagtgttt gggtgtcaaa cccatacgcg taatgaaagt     1020
gaacggaggt gagaacccct tagggtgcat catcgaccga tcctgatgtc ttcggatgga     1080
tttgagtaag agcatagctg ttgggacccg aaagatggtg aactatgcgt gaatagggtg     1140
aagccagagg aaactctggt ggaggctcgc agcggttctg acgtgcaaat cgatcgtcaa     1200
atttgcgtat aggggcgaaa gactaatcgg ctagacaggg tcagttcgcc cgaagagggt     1260
ggcagatcta cttgttcttt gtgctgacat gagtatctca gagtaatccg gcatatgcag     1320
cagctacaag tattcgcgac ccaaagcgta ggttcgatac gatatggcga ctctgcaaac     1380
caaaaatgat ctgcgatagc gatgtcccaa atgaagatga attcggaggt gatcctaagg     1440
aagctgtcaa gcgctcacat ggaggttgtg gaaacactca gcccgaagtg cgtcaacaat     1500
ctctccaact ttggggtaca tggaagatgc caaaggatga ggagaacgag ggcggtgcaa     1560
cgcaggagaa gaaacaaatt actccagaga tggctctcaa tgtcttcaaa agcatgtcca     1620
ccaaggagat ctacgatctt ggcttgaaca acgactacgc tcgtcctgac tggttgatta     1680
tcactgttct tccagttcca cctcccccag tccgaccaag tatctccatg gatggcacaa     1740
gtaccggcat gcgtggagag gatgatttga catacaagct tggtgatatc attcgtgcaa     1800
atggaaacgt taagcaggca caacaggaag g                                    1831
```

<210> SEQ ID NO 16
<211> LENGTH: 1895
<212> TYPE: DNA
<213> ORGANISM: Monilinia laxa
<220> FEATURE:
<221> NAME/KEY: misc_feature
<222> LOCATION: (956)..(957)
<223> OTHER INFORMATION: n is a, c, g, or t
<220> FEATURE:
<221> NAME/KEY: misc_feature
<222> LOCATION: (963)..(963)
<223> OTHER INFORMATION: n is a, c, g, or t
<220> FEATURE:
<221> NAME/KEY: misc_feature
<222> LOCATION: (978)..(978)
<223> OTHER INFORMATION: n is a, c, g, or t

<400> SEQUENCE: 16

```
gtggaagtaa aagtcgtaac aaggtttccg taggtgaacc tgcggaagga tcattacaga       60
gttcatgccc gaaagggtag acctcccacc cttgtgtatt attactttgt tgctttggcg      120
agctgccttc gggccttgta tgctcgccag agaataatca aactcttttt attaatgtcg      180
```

```
tctgagtact atataatagt taaaactttc aacaacggat ctcttggttc tggcatcgat    240
gaagaacgca gcgaaatgcg ataagtaatg tgaattgcag aattcagtga atcatcgaat    300
ctttgaacgc acattgcgcc ccttggtatt ccggggggca tgcctgttcg agcgtcattt    360
caaccctcaa gcacagcttg gtattgagtc tatgtcagca atggcaggct ctaaaatcag    420
tggcggcgcc gctgggtcct gaagggatta cctcagtaac ggcgagtgaa gcggtaaaag    480
ctcaaatttg aaatctggct cttttagagt ccgagttgta atttgtagaa gatgcttcgg    540
gtgtggttcc ggtctaagtt ccttggaaca ggacgtcata gagggtgaga atcccgtatg    600
tgactggata cctatgctca tgtgaagctc tttcgacgag tcagttgtt tgggaatgca    660 gctcaaaatg ggtggtatat ttcatctaaa gctaaatatt ggccagagac cgatagcgca    720
caagtagagt gatcgaaaga tgaaaagcac tttggaaaga gagttaaaca gtacgtgaaa    780
ttgttgaaag ggaagcgctt gcaatcagac ttgcacttgg tgttcatcgg ggtttctacc    840
ccgtgtactt catcaagttc aggccagcat cagtttgggt ggttagataa aggcttagag    900
aatgtggccc tcttcggggg gtgttatagc tctaggtgca atgtagccta cctggnntga    960
ggnccgcgct tcggctanga tgctggcgta atggttgtaa gcgacccgtc ttgaaacacg   1020
gaccaaggag tgtacctaat atgcgagtgt ttgggtgtta acccatacgc gtaatgaaag   1080
tgaacggagg tgagagccct taagggtgca tcatcgaccg atcctgatgt cttcggatgg   1140
atttgagtaa gagcatattg ggtgcgaccc gaaagatggt gatctatacg tgaatagggt   1200
gaagccagag gaaactctgg tggaggctcg cagcggttct gacgtgcaaa tcgatcgtca   1260
aatttgcgta taggggcgaa agactaatcg actagacagg gttagtttgc aaccaacttg   1320
aggtggtttg tttcatgtgc cttgatgcta acaccaaagt atcagagtaa tccagcttac   1380
aaggcagccg tttccatccg tgatcctaag cgcagattcg aagcaatatg gaaactctgc   1440
aagtccaaga tgatttgtga tagtgacgtc caggcgaacg aggaggaatt caatggagat   1500
ccaaaggaag ctgcaaagcg atcgcatgga ggatgcggca atactcaacc tgaagtccgt   1560
caaactgctc tggccctctg gggtacgtgg aagccgccca aggatgaaga cggagaggct   1620
gtgcaacctg acaagagaca aatcactccg gagatggctc ttaacgtctt tcgcagcatg   1680
accactgcag aaatccagga tgttggattg aacgcagatt atgctcgccc agaatggatg   1740
attattaccg ttctaccagt accaccgcct cccgttcgac caagtatttc catggatggt   1800
actggtcagg gtatgcgagg agaggatgat ttgacataca agttgggtga tatcattcgt   1860
gccaatggta acgttcgtca agcacaacaa gaagg                              1895

<210> SEQ ID NO 17
<211> LENGTH: 1830
<212> TYPE: DNA
<213> ORGANISM: Phialocephala fortinii

<400> SEQUENCE: 17
gtgtttacat actattgttg ctttggcggg ccgtggcctc cactgcgggc tctgctcgtg     60
tgtgcccgcc agagaaccaa actctgaatg ttagtgatgt ctgagtacta tctaatagtt    120
aaaactttca acaacggatc tcttggttct ggcatcgatg aagaacgcag cgaaatgcga    180
taagtaatgt gaattgcaga attcagtgaa tcatcgaatc tttgaacgca cattgcgccc    240
tgtggtattc cgcagggcat gcctgttcga gcgtcattta accactcacg cctagcgtgg    300
tattggggca cgcggtctcc gcggccctca aaatgagtgg cggcgccggt gggctctaag    360
```

```
cgtagtacat actcccgcta tagagttccc ccggtggctc gcgtaacggc gagtgaagcg     420
gtaacagctc aaatttgaaa gctgccaaca ggccgcgttg taatttgtag aagctgcttt     480
gggtgtcggc ccggtctaag ttccttggaa caggacgtca tagagggtga aatcccgta     540 tgtgatcggt gccgttgccc gtgtaaagcg ctttcgacga gtcgagttgt ttgggaatgc     600
agctcaaaat gggtggtaaa tttcatctaa agctaaatat tggccagaga ccgatagcgc     660
acaagtagag tgatcgaaag atgaaaagca ctttggaaag agagttaaac agtacgtgaa     720
attgttgaaa gggaagcgct tgcaaccaga cttgcgggcg gtcgatcatc cgaggttctc     780
cccggtgcac tcgatcgttc tcaggccagc atcggtttcc ggggtgggat aaaggcggtg     840
ggaatgtggc tcttcggagt gttatagccc accgtgcaat gccgccactg gggaccgagg     900
accgcgcttc ggctaggatg ctggcgtaat ggttgtaagc gacccgtctt gaaacacgga     960
ccaaggagtc taacatctat gcgagtgttt gggtgtcaaa cccatacgcg taatgaaagt    1020
gaacggaggt aagagccctt tagggtgcat tatcgaccga tcctgatgtc ttcggatgga    1080
tttgagtaag agcatagctg ttgggacccg aaagatggtg aactatgcgt gaataggggtg   1140 aagccagagg aaactctggt ggaggctcgc agcggttctg acgtgcaaat cgatcgtcaa    1200
atttgcgtat aggggcgaaa gactaatcgg ctagacagag tcagttcgcc cgatgagggt    1260
ggcagatcta cttgttcttg tgctgacatg agtatctcag agtaatccgg ccttcaaagc    1320
agctgtttcc attcgagacc cgaagcgtag gttcgatacg atttggcgac tttgcaagcc    1380
caagatgatc tgcgatagcg acgtttctgc ggacgatcag gaattcggtg gcgatccaag    1440
ggaagctgtg aagcgctctc atggaggttg tggaaatact cagcccgagg tgcgccagca    1500
ggctctgcag ctttggggta catggaagat gcctaaggac gaggagaacg agggaaacca    1560
atccgagaag agacaaatca ctccagagat ggctctgaac gtcttccgaa gcatgtctac    1620
tgctgagatt cgcgaccttg ggttgagcaa cgattatgcc cgtcccgact ggctgatcat    1680
cacagtcctt ccagttcctc ctccgccggt tcgaccaagt atttctatgg atggcacaag    1740
cactggaatg cgtggagaag atgatttgac atacaagctc ggtgatatca ttcgtgcgaa    1800
tggaaatgtc aagcaggcac aacaggaagg                                    1830
```

<210> SEQ ID NO 18
<211> LENGTH: 1835
<212> TYPE: DNA
<213> ORGANISM: Vibrissea truncorum

<400> SEQUENCE: 18

```
gtgtttacat actcttgttg ctttggcagg ccgtggcctc cactgcgggc tctgctcgta     60
cgtgcccgcc agaggaccaa actctgaatg ttagtgatgt ctgagtacta tataatagtt    120
aaaactttca acaacggatc tcttggttct ggcatcgatg aagaacgcag cgaaatgcga    180
taagtaatgt gaattgcaga attcagtgaa tcatcgaatc tttgaacgca cattgcgccc    240
ggtggtattc cgccgggcat gcctgttcga gcgtcattat aaccaatcac gcctggcgtg    300
gtgttggggc acacggctcc gtggccctca aaatcagtgg cgatgccggt tggctctaag    360
cgtagtaact tctctcgcta tagatgtctg ctggttgctc gccctcagta acggcgagtg    420
aagcggtaac agctcaaatt tgaaagctgc caacaggccg cattgtaatt tgtagaggat    480
gctttggggg ttggcccggt ctaagttcct tggaacagga cgtcatagag ggtgagaatc    540
ccgtatgtgc ccggtgcccg ccccgtgta aagctccttc aacgagtcga gttgtttggg    600
aatgcagctc aaaatgggtg gtatatttca tctaaagcta aatattggcc agagaccgat    660
```

-continued

```
agcgcacaag tagagtgatc gaaagatgaa aagcactttg gaaagagagt taaacagtac      720
gtgaaattgt tgaaagggaa gcgcttgcaa tcagacttgc aggcggtcga tcatccgggg      780
ttctcctcgg tgcactcggc cgtcttcagg ccagcatcag tttcggtggt gggataaagg      840
ccttgggaat gtagcttctt cgggagtgtt atagccctcg gtgcaatgcc gcctaccggg      900
actgaggacc gcgcttcggc taggatgctg gcgtaatggt tgtaagcgac ccgtcttgaa      960
acacggacca aggagtctaa catctatgcg agtgtttggg tgtcaaaccc atacgcggaa     1020
tgaaagtgaa cggaggtaag aacccttag ggcgcattat cgaccgatcc tgatgtcttc     1080
ggatggattt gagtaagagc atagctgttg ggacccgaaa gatggtgaac tatgcgtgaa     1140
tagggtgaag ccagaggaaa ctctggtgga ggctcgcagc ggttctgacg tgcaaatcga     1200
tcgtcaaatt tgcgtatagg ggcgaaagac taatcgatta gacagggttt gtttgcctgt     1260
tgaaatggga atctaacagt tcatttgtgc tgacacggat gaaaatagaa taatcctgca     1320
ttcaaggccg ctgttaatat tcgagaccca aagcgaaaat tcgatacgat atggcgactc     1380
tgcaagccga agcttgtttg cgacagtgac atcaatcccg acgatccaga gttcaacagc     1440
gatcccaagg aagcagcaaa gcgttctcat ggtggatgtg gcaatactca acccgaggtg     1500
cgccaacagg ctttacaact ttggggtacc tggaagatgc cgaaggatga ggagaacgat     1560
ggtggatctg agaagagaca aatcactcca gagatggctc tgaacgttct tcgaagcatg     1620
tctacttctg acattcggga tctgggactc agcgtcgatt atgctcgtcc tgagtggttg     1680
atcatcacag ttctgccagt tcctccacca cccgtccgac ccagtatttc catggatggc     1740
acaagcactg gtatgcgcgg agaggatgat ttgacctata agcttggtga tattatccgt     1800
gcaaatggca atgtgaagca ggcacaacag gaagg                                1835
```